(12) United States Patent
Dairoku et al.

(10) Patent No.: US 7,473,739 B2
(45) Date of Patent: Jan. 6, 2009

(54) PARTICULATE WATER ABSORBENT AGENT AND PRODUCTION METHOD THEREOF, AND WATER ABSORBENT ARTICLE

(75) Inventors: Yorimichi Dairoku, Himeji (JP); Yoshifumi Adachi, Himeji (JP); Kozo Nogi, Kakogawa (JP); Hiroki Inoue, Kyoto (JP); Katsuyuki Wada, Himeji (JP); Yoshio Irie, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 272 days.

(21) Appl. No.: 11/049,995

(22) Filed: Feb. 4, 2005

(65) Prior Publication Data

US 2005/0209352 A1 Sep. 22, 2005

(30) Foreign Application Priority Data

| Feb. 5, 2004 | (JP) | ................ 2004-029590 |
| Mar. 30, 2004 | (JP) | ................ 2004-100002 |
| Sep. 6, 2004 | (JP) | ................ 2004-258284 |

(51) Int. Cl.
*C08F 8/32* (2006.01)

(52) U.S. Cl. .............. 525/327.6; 525/327.7; 525/328.2; 525/328.4; 525/329.9; 525/330.1

(58) Field of Classification Search .............. 525/327.6, 525/327.7, 328.2, 328.4, 329.9, 330.1
See application file for complete search history.

(56) References Cited

U.S. PATENT DOCUMENTS

| 4,093,776 | A | 6/1978 | Aoki et al. |
| 4,286,082 | A | 8/1981 | Tsubakimoto et al. |
| 4,367,323 | A | 1/1983 | Kitamura et al. |
| 4,446,261 | A | 5/1984 | Yamasaki et al. |
| 4,526,937 | A | 7/1985 | Hsu |
| 4,625,001 | A | 11/1986 | Tsubakimoto et al. |
| 4,666,983 | A | 5/1987 | Tsubakimoto et al. |
| 4,683,274 | A | 7/1987 | Nakamura et al. |
| 4,734,478 | A | 3/1988 | Tsubakimoto et al. |
| 4,873,299 | A | 10/1989 | Nowakowsky et al. |
| 4,948,818 | A | 8/1990 | Carmody et al. |
| 4,973,632 | A | 11/1990 | Nagasuna et al. |
| 4,985,518 | A | 1/1991 | Alexander et al. |
| 5,061,259 | A | 10/1991 | Goldman et al. |
| 5,124,416 | A | 6/1992 | Haruna et al. |
| 5,145,906 | A | 9/1992 | Chambers et al. |
| 5,228,814 | A | 7/1993 | Suwijn |
| 5,229,488 | A | 7/1993 | Nagasuna et al. |
| 5,244,735 | A | 9/1993 | Kimura et al. |
| 5,250,640 | A | 10/1993 | Irie et al. |
| 5,264,495 | A | 11/1993 | Irie et al. |
| 5,288,814 | A | 2/1994 | Long et al. |
| 5,380,808 | A | 1/1995 | Sumiya et al. |
| 5,385,983 | A | 1/1995 | Graham |
| 5,409,771 | A | 4/1995 | Dahmen et al. |
| 5,422,405 | A | 6/1995 | Dairoku et al. |
| 5,453,323 | A | 9/1995 | Chambers et al. |
| 5,597,873 | A | 1/1997 | Chambers et al. |
| 5,633,316 | A | 5/1997 | Gartner et al. |
| 5,728,742 | A | 3/1998 | Staples et al. |
| 5,744,564 | A * | 4/1998 | Stanley et al. ............ 526/317.1 |
| 5,981,070 | A | 11/1999 | Ishizaki et al. |
| 5,987,070 | A | 11/1999 | Fimoff et al. |
| 6,071,976 | A | 6/2000 | Dairoku et al. |
| 6,107,358 | A | 8/2000 | Harada et al. |
| RE37,021 | E | 1/2001 | Aida |
| 6,174,978 | B1 | 1/2001 | Hatsuda et al. |
| 6,207,772 | B1 | 3/2001 | Hatsuda et al. |
| 6,228,930 | B1 | 5/2001 | Dairoku et al. |
| 6,241,928 | B1 | 6/2001 | Hatsuda et al. |
| 6,254,990 | B1 | 7/2001 | Ishizaki et al. |
| 6,562,879 | B1 | 5/2003 | Hatsuda et al. |
| 2003/0153887 | A1 * | 8/2003 | Nawata et al. ............ 604/372 |
| 2004/0106745 | A1 | 6/2004 | Nakashima et al. |

FOREIGN PATENT DOCUMENTS

| CA | 2426802 A1 | 4/2003 |
| EP | 0001706 A1 | 5/1979 |
| EP | 0349240 A2 | 1/1990 |

(Continued)

*Primary Examiner*—Bernard Lipman
(74) *Attorney, Agent, or Firm*—Harness, Dickey & Pierce, P.L.C.

(57) ABSTRACT

A particulate water absorbing agent of the present invention includes a water absorbent resin, having a cross-linking structure, whose surface has been cross-linked by adding a surface treatment agent, wherein: (i) a mass average particle diameter (D50) ranges from 200 to 600 μm and 95 to 100 wt % of a particulate water absorbing agent whose particle diameter ranges from less than 850 μm to not less than 150 μm is contained with respect to 100 wt % of whole the particulate water absorbing agent, and (ii) a logarithmic standard deviation (σζ) of particle size distribution ranges from 0.25 to 0.45, and (iii) a compressibility rate defined by a following equation ranges from 0 to 18%, and (iv) a surface tension of a supernatant liquid obtained in 4 minutes after dispersing 0.5 g of the particulate water absorbing agent in 50 ml of physiological saline whose temperature is 20° C. is 55 mN/m or more, the compressibility rate (%)=$(P-A)/P \times 100$ where P represents a tapped bulk density of the particulate water absorbing agent and A represents a loose bulk density of the particulate water absorbing agent.

4 Claims, 5 Drawing Sheets

FOREIGN PATENT DOCUMENTS

| | | |
|---|---|---|
| EP | 0605150 A1 | 7/1994 |
| EP | 0811636 A1 | 12/1997 |
| EP | 0922717 A1 | 6/1999 |
| EP | 0955086 A2 | 11/1999 |
| EP | 1510229 A1 | 3/2005 |
| JP | 53-46389 A | 4/1978 |
| JP | 55-133413 A | 10/1980 |
| JP | 57-94011 A | 6/1982 |
| JP | 57-158209 A | 9/1982 |
| JP | 58-180233 A | 10/1983 |
| JP | 59-80459 A | 5/1984 |
| JP | 60-55002 A | 3/1985 |
| JP | 60-71623 A | 4/1985 |
| JP | 61-16903 A | 1/1986 |
| JP | 61-58658 A | 3/1986 |
| JP | 61-87702 A | 5/1986 |
| JP | 62-227904 A | 10/1987 |
| JP | 63-105064 A | 5/1988 |
| JP | 01-126310 | 5/1989 |
| JP | 1-126310 A | 5/1989 |
| JP | 2-49002 A | 2/1990 |
| JP | 2-191604 A | 7/1990 |
| JP | 03-028203 | 2/1991 |
| JP | 3-28203 A | 2/1991 |
| JP | 3-95204 A | 4/1991 |
| JP | 4-175319 A | 6/1992 |
| JP | 4-227705 A | 8/1992 |
| JP | 5-156034 | 6/1993 |
| JP | 6-39485 B2 | 5/1994 |
| JP | 06-199969 | 7/1994 |
| JP | 6-199969 A | 7/1994 |
| JP | 7-8883 B2 | 2/1995 |
| JP | 7-224204 A | 8/1995 |
| JP | 7-242709 A | 9/1995 |
| JP | 8-143782 A | 6/1996 |
| JP | 9-136966 A | 5/1997 |
| JP | 10-114801 | 5/1998 |
| JP | 2881739 B2 | 2/1999 |
| JP | 01-126310 | 5/1999 |
| JP | 2000-290381 | 10/2000 |
| JP | 2000-302876 A | 10/2000 |
| JP | 2002-35580 | 2/2002 |
| JP | 3283570 B2 | 3/2002 |
| JP | 2003-82250 A | 3/2003 |
| JP | 2004-121400 A | 4/2004 |
| JP | 2004-512165 A | 4/2004 |
| JP | 2004-261796 A | 9/2004 |
| WO | WO 2004/069293 A1 | 8/2004 |
| WO | WO 2004/069915 A2 | 8/2004 |
| WO | WO 2004/069936 A1 | 8/2004 |
| WO | WO 2004/113452 A1 | 12/2004 |

* cited by examiner

PARTICULATE WATER ABSORBENT AGENT AND PRODUCTION METHOD THEREOF, AND WATER ABSORBENT ARTICLE

FIELD OF THE INVENTION

The present invention relates to (i) a particulate water absorbing agent containing a water absorbent resin as a main component, (ii) a production method thereof, and (iii) a water absorbent article. More specifically, the present invention relates to a particulate water absorbing agent and a water absorbent article, being superior in fluidity at the time of dry or moisture absorption and in a powder property such as bulk density stability without losing its water absorbent performance, each of which has a stable water absorbent property, said particulate water absorbing agent and said water absorbent article less allowing absorbed liquid to return and having a superior absorbent property in case where the particulate water absorbing agent is used in an absorbent core of a sanitary material such as a disposable diaper, a sanitary napkin, an incontinence pad, and the like.

BACKGROUND OF THE INVENTION

Recently, a water absorbent resin is widely used as a main construction material of sanitary materials (absorbent articles) such as disposable diapers, sanitary napkins, incontinence pads and the like, in order to absorb body fluids (e.g. urine, blood, and the like). Well-known examples of the water absorbent resin are (i) cross-linked partially neutralized polyacrylic acid; (ii) a hydrolyzed starch-acrylonitrile graft polymer; (iii) a neutralized starch-acrylic graft polymer; (iv) a saponified vinyl acetate-acrylic ester copolymer; (v) cross-linked carboxymethylcellulose; (vi) hydrolyzed acrylonitrile copolymer or hydrolyzed acrylamide copolymer, or cross-linked acrylonitrile copolymer or cross-linked acrylamide copolymer; (vii) a cross-linked cationic monomer, (viii) a cross-linked isobutylene-maleic acid copolymer; (ix) a cross-linked polymer of 2-acrylamide-2-methylpropanesulfonic acid and acrylic acid; (x) and the like. There has conventionally been needs for a water absorbent resin having the following water absorbent properties: (i) a high absorbency for a aqueous liquid such as a body fluid, (ii) an excellent absorption rate, (iii) excellent liquid permeability, and (iv) excellent gel strength of a swollen gel, and (v) an excellent absorptive capacity when water is absorbed from a base material containing a aqueous liquid, (vi) and the like.

Each of these water absorbent resins has an even cross-linking structure in the polymer, and is water-insoluble. Generally, in order to attain the foregoing water absorbent properties, surfaces of particles of the water absorbent resin are further cross-linked by using a cross-linking agent or the like, thereby causing the particles to have a cross-linking density gradient. Thus, (i) a water-absorption rate of the water absorbent resin is improved, (ii) generation of fish eye is prevented, (iii) gel strength is improved, (iv) an absorbency of the water absorbent resin under pressure is improved, (v) gel blocking is prevented, and (vi) liquid permeability is improved.

For example, surface cross-linking processes for causing a vicinity of particle surfaces of the water absorbent resin to have a cross-linking density gradient are described in European Patent No. 0349240, European Patent No. 0605150, Japanese Publication for Unexamined Patent Application, Tokukaihei 7-242709, Japanese Publication for Unexamined Patent Application, Tokukaihei 7-224304, U.S. Pat. Nos. 5,409,771, 5,597,873, 5,385,983, and the like (hereinafter, referred to as Prior Art 1).

In addition to the foregoing methods recited, a water absorbent including a water absorbent resin and metal soap in order to improve liquid permeability, is described in Japanese Publication for Unexamined Patent Application, Tokukaisho 61-58658. Moreover, there are needs for such a water absorbent resin which not only has the foregoing water absorbent properties, but also has the following advantages: The water absorbent resin has excellent powder fluidity in a dry state and excellent powder fluidity in a moisture absorption state at the time of production and transportation of the water absorbent resin, at the time of production of an absorbent core by processing the water absorbent resin and a fiber base material or the like, and at the time of moisture absorption, so that the water absorbent resin rarely adheres to a device or the like. As an attempt to produce water absorbent resin having excellent fluidity at the time of moisture absorption, a water absorbent in which an inorganic substance such as amorphous silicon dioxide, kaoline, or the like is added, is proposed. Specifically, for example, art related to a water absorbent including powder of an inorganic substance and powder of a water absorbent resin is disclosed in U.S. Pat. No. 4,734,478, Japanese Publication for Unexamined Patent Application, Tokukaisho 59-80458, and U.S. Pat. No. 5,453,323. In addition to the technique in which an inorganic substance is added, a water absorbent agent in which stearic acid and powder of an inorganic substance are added as additives is described in Japanese Publication for Unexamined Patent Application, Tokukaisho 63-105064 (hereinafter, referred to as Prior Art 2).

Further, a water absorbent agent in which quaternary ammonium salt is added as additives is described in U.S. Pat. No. 5,728,742. Moreover, a particulate water absorbing agent in which denatured polysiloxane, polyethyleneglycol, polypropyleneglycol, or the like are added is disclosed in Japanese Publication for Unexamined Patent Application, Tokukaihei 9-136966 and European Patent No. 0001706. Further, a particulate water absorbing agent containing a polymer dispersant is disclosed in Japanese Publication for Unexamined Patent Application, Tokukaihei 8-143782 (hereinafter, referred to as Prior Art 3).

Moreover, in order to prevent generation of the fish eye and gel blocking, a particulate water absorbing agent obtained by treating a water absorbent resin with a surfactant is disclosed in Japanese Examined Patent Publication, Tokukohei 6-39485 (Published on May 25, 1995), Japanese Patent No. 3283570 (Registered on Mar. 1, 2003), Japanese Publication for Unexamined Patent Application, Tokukai 2003-82250 (Published on Mar. 19, 2003) (hereinafter, referred to as Prior Art 4). Further, an attempt to improve the bulk density is proposed. For example, Japanese Publication for Unexamined Patent Application, Tokukai 2000-302876 (Published on Oct. 31, 2000) recites such arrangement that: indefinite-shape crushed water absorbent resin powder, having large bulk density, whose absorbency against pressure is favorable, is obtained by cross-linking surfaces of cross-linked polymer particles that have been ground (hereinafter, referred to as Prior Art 5).

However, each of the foregoing methods raises such problems that: it is impossible to obtain sufficient fluidity in a dry state and sufficient powder fluidity at the time of moisture absorption; the absorbency against pressure significantly drops; a surface tension of absorbed liquid such as urine drops in case where the water absorbent resin comes in contact with the absorbed liquid. For example, in the Prior Art 1, the fluidity in the dry state and the fluidity at the time of moisture absorption are insufficient, and the water absorbent resin is hard to treat. Further, in the Prior Art 2, by adding an inorganic substance, it is possible to improve the fluidity at the time of moisture absorption, but the fluidity and the absorbency in the dry state significantly drop, so that the water absorbent resin is hard to treat. As a result, an absorbent article using the same cannot sufficiently exhibit water absorbent properties. Particularly, in the technique recited in Tokukaisho 61-58658, generally 1 to 10 wt %, preferably 5 to 80 wt % of metal soap is added to the water absorbent resin. In case where such a large quantity of metal soap is added, its properties such as a hydrophobic property, a water-repellent property, and a surface-activating property have bad influence on the absorbent properties of the water absorbent resin. Further, the Prior Art 3 raises such problems that: the fluidity at the time of moisture absorption is insufficient; a surface tension of absorbed liquid such as urine drops in case where the water absorbent resin is in contact with the absorbed liquid. When the water absorbent resin is used in a disposable diaper for example, the water absorbent property of the water absorbent article drops (increase in its re-wet amount (an amount of absorbed liquid which has returned from the absorbent core) or a similar problem occurs). In this way, the water absorbent properties are not sufficient.

Further, in the Prior Art 4, an amount of the surfactant used in the water absorbent resin is large. This is not economical. Further, in case where the particulate water absorbing agent is in contact with absorbed liquid such as urine, a surface tension of the absorbed liquid drops. As a result, such arrangement has bad influence on the water absorbent properties of the particulate water absorbing agent (increase in its re-wet amount or a similar problem occurs) in case where the particulate water absorbing agent is used in a disposable diaper for example.

Further, as to the indefinite-shape crushed water absorbent resin powder in the Prior Art 5, its bulk density is high and its absorbency against pressure is favorable. In order to achieve these properties, the surface of the cross-linked polymer is ground, so that the number of steps required in producing power increases. Further, it is necessary to remove fine powder which has occurred in grinding the surface of the cross-linked polymer. Thus, cost and troubles taken in the production increase.

The present invention was made in view of these problems, and an object of the present invention is easily realize a particulate water absorbing agent having such properties that: (i) the fluidity at the time of moisture absorption and the powder fluidity in the dry state are favorable, so that it is easy to treat the water absorbent resin at the time of transport, which causes the water absorbent resin to less adhere to a production device; (ii) an absorbency against pressure is high; (iii) the water absorbent resin has a superior water absorbent property which prevents a surface tension of absorbed liquid such as urine from dropping in case where the water absorbent resin is in contact with the absorbed liquid; and (iv) the fluidity and the bulk density of the water absorbent resin are stably increased without losing the water absorbent property.

SUMMARY OF THE INVENTION

The inventors of the present invention focused on such condition that: if it is possible to realize (i) superior fluidity, (ii) a high water absorbent performance, (iii) minimization of drop in a surface tension of absorbed liquid such as urine in case where a particulate water absorbent agent (hereinafter, referred to as a particulate water absorbing agent) is in contact with the absorbed liquid, it is easy to produce a water absorbent article such as a diaper having the particulate water absorbing agent, and it is possible to provide a superior water absorbent article whose re-wet amount is small in case where the particulate water absorbing agent is provided in the water absorbent article. As a result of diligent study based on this condition, the inventors found that: it is possible to achieve the foregoing object by using (i) a water absorbent resin, having specific particle size distribution, whose surface is cross-linked, and (ii) a powder lubricant or a surfactant. As a result, they completed the present invention.

That is, a particulate water absorbing agent resin of the present invention includes a water absorbent resin, having a cross-linking structure, whose surface has been cross-linked by adding a surface treatment agent, wherein: (i) a mass average particle diameter (D50) ranges from 200 to 600 μm and 95 to 100 wt % of a particulate water absorbing agent whose particle diameter ranges from less than 850 μm to not less than 150 μm is contained with respect to 100 wt % of whole the particulate water absorbing agent, and (ii) a logarithmic standard deviation ($\sigma\zeta$) of particle size distribution ranges from 0.25 to 0.45, and (iii) a compressibility rate defined by a following equation ranges from 0 to 18%, and (iv) a surface tension of a supernatant liquid obtained in 4 minutes after dispersing 0.5 g of the particulate water absorbing agent in 50 ml of physiological saline whose temperature is 20° C. is 55 mN/m or more, the compressibility rate (%)=$(P-A)/P\times100$ where P represents a tapped (packed) bulk density of the particulate water absorbing agent and A represents a loose bulk density of the particulate water absorbing agent.

Further, it is preferable to arrange the particulate water absorbing agent of the present invention so that an insertion work indicative of a work in case of inserting an insertion member down to a 20 mm depth of a particle layer of the particulate water absorbing agent is 0 g weight×mm or more and 75,000 g weight×mm or less.

A specific example of the particulate water absorbing agent of the present invention is a particulate water absorbing agent further including a surfactant or a powder lubricant.

Further, it is preferable to arrange the particulate water absorbing agent of the present invention so that an absorbency against pressure of 2.03 kPa is 20 g/g or more.

It is preferable to arrange the particulate water absorbing agent of the present invention so that an absorbency against pressure of 4.83 kPa is 17 g/g or more.

Further, it is preferable to arrange the particulate water absorbing agent of the present invention so that a saline flow conductivity (SFC) of the particulate water absorbing agent is $20(10^{-7}\cdot cm^3\cdot s\cdot g^{-1})$ or more.

According to the foregoing arrangement, it is possible to provide a particulate water absorbing agent in which: a friction between powder particles in a dry state is small, and blocking or caking in a moisture absorption state can be prevented, and adhesion to a device or the like hardly occurs, and its powder fluidity is high. Thus, it is possible to avoid (i) halt of a production device which is caused by an excessive load and (ii) clogging of the particulate water absorbing agent in a pipe used in transportation. Further, it is possible to alleviate process damages caused by mechanical impact and the like, and to reduce a powder stirring force, and to reduce energy required in pneumatic transportation. Further, the fluidity increases, so that it is possible to reduce a time taken to move the water absorbent from the container to the hopper or a time taken to fill the container with the particulate water absorbing agent moved from the hopper, thereby improving an efficiency in the operation.

Further, the friction between powder particles is small, and the bulk density increases, so that it is possible to increase an amount of the particulate water absorbing agent filled in a container having the same capacity. As a result, it is possible to reduce the transportation (shipping) cost and it is possible to increase an amount of the particulate water absorbing agent stored in a storage tank.

Further, an absorbent performance such as the absorbency against pressure is high, and the surface tension of the absorbed liquid such as urine hardly drops in case where the particulate water absorbing agent is in contact with the absorbed liquid, so that a re-wet amount of an absorbent article is small, thereby providing a superior absorbent article.

It is preferable that the powder lubricant is a macromolecule additive whose lateral chain has a hydrocarbon group containing seven or more carbons in its molecule and whose mass average particle diameter is 0.01 μm or more and 100 μm or less.

Further, it is preferable that an amount of the macromolecule additive ranges from 0.01 wt % or more to 10 wt % or less with respect to 100 wt % of the water absorbent resin.

Further, it is preferable that the macromolecule additive is obtained by (co)polymerizing 15 wt % or more and 100 wt % or less of a monomer whose lateral chain has a hydrocarbon group containing seven or more carbons in its molecule with respect to a (co)polymer serving as a macromolecule additive.

Further, it is preferable that the macromolecule additive in a solution phase or in a suspension liquid phase is added to the surface of the water absorbent resin.

Further, it is preferable that the macromolecule additive is added to a surface of the water absorbent resin as powder whose mass average particle diameter is 0.1 μm or more and 100 μor less.

According to the foregoing arrangement, a friction between powder particles is small even in the moisture absorption state, so that it is possible to provide a particulate water absorbing agent showing high fluidity even in the moisture absorption state.

Further, it is preferable that an amount of the surfactant added ranges from 0.0005 weight parts or more to 0.012 weight parts or less with respect to 100 weight parts of the water absorbent resin.

Further, it is preferable that the surfactant is a nonionic surfactant whose HLB ranges from 8 to 18.

According to the foregoing arrangement, by using the surfactant whose additional amount and HLB are in the foregoing ranges, it is possible to reduce a friction between powder particles and it is possible to prevent a surface tension of absorbed liquid from dropping, so that it is possible to prevent an absorbent property of the particulate water absorbing agent from dropping.

Further, in order to solve the foregoing problem, a particulate water absorbing agent of the present invention includes a water absorbent resin and a powder lubricant (excluding metal soap), wherein 0.0001 wt % to 0.1 wt % of the lubricant is contained with respect to the water absorbent resin.

According to the foregoing arrangement, likewise, the particulate water absorbing agent of the present invention increases the fluidity and the bulk density and does not drop the water absorbent property.

It is preferable to arrange the particulate water absorbing agent of the present invention so that the loose bulk density is 0.7 g/ml or more.

It is preferable to arrange the particulate water absorbing agent of the present invention so that the powder lubricant is added to a water absorbent resin powder.

Further, it is preferable to arrange the particulate water absorbing agent of the present invention so that the water absorbent resin has at least one shape selected from a group of an indefinite-shape crushed particle, a granulated indefinite-shape crushed particle, a granulated spherical particle, and a granulated elliptical particle, or has a shape obtained by mixing the indefinite-shape crushed particle, the granulated indefinite-shape crushed particle, the granulated spherical particle, and the granulated elliptical particle with each other.

Further, in order to solve the foregoing problem, an absorbent article of the present invention includes the aforementioned particulate water absorbing agent.

In order to solve the foregoing problem, a method of the present invention for producing a particulate water absorbing agent includes the step of adding a surface treatment agent, containing (A) a surface cross-linking agent and (B) a surfactant or a powder lubricant as essential components, to a water absorbent resin, having a cross-linking structure, so as to cross-link a surface of the water absorbent resin, wherein: an amount of the surfactant or the powder lubricant added ranges from 0.0005 weight parts or more to 0.012 weight parts or less with respect to 100 weight parts of the water absorbent resin, and a surface tension of a supernatant liquid obtained in 4 minutes after dispersing 0.5 g of the particulate water absorbing agent in 50 ml of physiological saline whose temperature is 20° C. is 55 mN/m or more.

Further, it is preferable that: (i) a mass average particle diameter (D50) ranges from 200 to 600 μm, and (ii) a logarithmic standard deviation (σζ) of particle size distribution ranges from 0.25 to 0.45.

Further, it is preferable that: a compressibility rate defined by a following equation ranges from 0 to 18%, the compressibility rate (%)=$(P-A)/P \times 100$ where P represents a tapped bulk density of the particulate water absorbing agent and A represents a loose bulk density of the particulate water absorbing agent.

For a fuller understanding of the nature and advantages of the invention, reference should be made to the ensuing detailed description taken in conjunction with the accompanying drawings.

BRIEF DESCRIPTION OF THE DRAWINGS

FIG. 7(a) is a cross sectional view thereof, and FIG. 7(b) is a plan view thereof.

DESCRIPTION OF THE EMBODIMENTS

Figure 1:
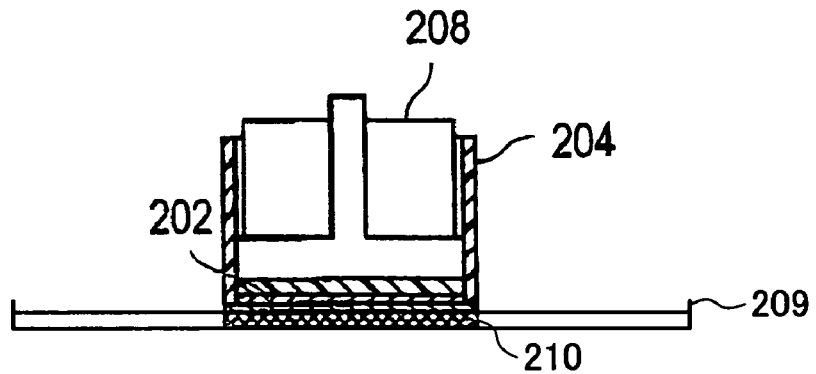
FIG. 1 is a cross sectional view schematically showing an arrangement of a device for measuring an absorbency against pressure in an Example of the present invention.

Detailed description is made below as to a water absorbent resin, a particulate water absorbing agent, and a water absorbent article using the same according to the present invention. While the invention is susceptible to various modifications and alternative forms, specific embodiments thereof will be described below by way of example. It should be understood, however, that it is not intended to limit the invention to the particular forms disclosed, but on the contrary, the invention is to cover all modifications, equivalents, and alternatives falling within the scope of the invention as defined in the appended claims.

The present invention is described as the following Embodiments 1 to 3. A particulate water absorbing agent of the present invention, preferably, includes a water absorbent resin and a powder lubricant or a surfactant. However, the particulate water absorbing agent is limited to this. The particulate water absorbing agent is obtained: by adding a macromolecule additive, one of powder lubricants, whose lateral chain has a hydrocarbon group containing seven or more carbons in its molecule (Embodiment 1); by adding a surface treatment agent essentially containing (A) a surface cross-linking agent and (B) a surfactant, and heating thus obtained resultant so as to carry out surface cross-linking treatment (Embodiment 2); and by adding a powder lubricant (Embodiment 3).

The following description will specifically explain a water absorbent resin, a macromolecule additive, a surfactant, a powder lubricant, a particulate water absorbing agent, and a water absorbent article.

The particulate water absorbing agent of the present invention is used to absorb water, various kinds of aqueous solution, and aqueous solution such as urine and blood, and contains generally 70 wt % (mass %) or more to 100 wt % or less, more preferably 80 wt % or more to 100 wt % or less, most preferably 90 wt % or more to 100 wt % or less of a pure resin component of a water absorbent resin, with respect to a solid component of the water absorbent resin, as a main component out of all the components contained in the particulate water absorbing agent. The particulate water absorbing agent includes a water absorbent resin and a macromolecule additive whose lateral chain has a hydrocarbon group containing seven or more carbons, and may further include a compound (hereinafter, referred to as other component) other than the water absorbent resin and the macromolecule additive.

The following description will detail (i) a water absorbent resin contained in the particulate water absorbing agent of the present invention, (ii) a macromolecule additive, (iii) the particulate water absorbing agent, (iv) a parameter at which it is possible to exhibit the excellent absorbent properties and fluidity as powder, and (v) an absorbent article using the particulate water absorbing agent. Note that, in the present specification, "mass" and "weight" are synonymously used.

(I) Water Absorbent Resin

In order to achieve the foregoing object, the present invention essentially uses a water absorbent resin obtained by carrying out cross-linking polymerization with respect to an acid group and/or a salt-containing unsaturated monomer (any water absorbent resin may be used as long as the water absorbent resin is subjected to the cross-linking polymerization, and it is possible to use a water absorbent resin obtained by carrying out a cross-linking reaction based on a cross-linking agent or self cross-linking at the time of polymerization after polymerizing an acid group and/or a salt-containing unsaturated monomer.

The water absorbent resin of the present invention is a cross-linked polymer that has a water-swelling property and water insolubility and thus can form a hydrogel. For example, the water-swelling property is such a property that: by immersing the water absorbent resin into ion-exchange water, a substance having the property absorbs an amount of aqueous liquid greater than its own weight by a factor of at least 5 or more, preferably by a factor of 50 to 1000. Further, the water insolubility is such a property that: in a water absorbent resin having the property, preferably 30 wt % or less (lower limit is 0 wt %), more preferably 25 wt % or less, furthermore preferably 20 wt % or less, particularly preferably 15 wt % or less, and most preferably 10 wt % of a non-cross-linked water soluble component (water soluble macromolecule) is contained. How to measure the water-swelling property and water insolubility are specifically defined in Examples described later.

Further, the cross-linking polymer is a polymer having a cross-linking structure (hereinafter, referred to as internally cross-linking structure) in polymer obtained by polymerizing an unsaturated monomer for the sake of better absorbent properties. Moreover, the water absorbent resin may be subjected to such a surface cross-linking treatment that: surfaces of particles of the water absorbent resin are cross-linked, or may be free from the surface cross-linking treatment. In order to obtain the excellent absorbent properties, it is preferable to perform the surface cross-linking treatment.

Examples of the water absorbent resin are one kind or two or more kinds of: partially neutralized polyacrylic acid polymer; hydrolyzed starch-acrylonitrile graft polymer; starch-acrylic acid graft polymer or neutralized starch-acrylic acid graft polymer; cross-linked carboxymethylcellulose; saponified vinyl acetate-acrylic acid ester copolymer; hydrolyzed acrylonitrile copolymer or hydrolyzed acrylamide copolymer, or cross-linked acrylonitrile copolymer or cross-linked acrylamide copolymer; denaturated carboxyl-group-containing cross-linked polyvinyl alcohol; a cross-linked cationic monomer; a cross-linked polymer of 2-acrylamide-2-methylpropanesulfonic acid and acrylic acid; cross-linked isobutylene-maleic anhydride copolymer; and the like. It is preferable to use partially neutralized polyacrylic acid polymer obtained by polymerizing and cross-linking a monomer containing acrylic acid and/or its salt (neutralized acrylic acid) as a main component.

The water absorbent resin constituted of the cross-linking polymer is obtained by polymerizing and cross-linking an unsaturated monomer, and is subjected to the surface cross-linking treatment as required. The following description will explain an unsaturated monomer, a cross-linking monomer, a polymerization initiator, and a production method of the water absorbent resin that are used to produce the water absorbent resin.

<Unsaturated Monomer>

As the unsaturated monomer used to obtain the water absorbent resin contained in the particulate water absorbing agent of the present invention, it is preferable to use a monomer by which it is possible to obtain a desired cross-linking polymer.

For example, in case where the cross-linking polymer is a partly neutralized polyacrylic polymer, it is preferable to use acrylic acid and/or its salt (neutralized acrylic acid) as main components. And, (i) acrylic acid and/or its salt, and (ii) another monomer may be used in combination as copolymer components. Thus, it is possible to give not only the water absorbent properties but also special properties such as an antibacterial property and a deodorant property to the water absorbent resin obtained as a final product, and it is possible to obtain the water absorbent resin at lower cost.

As a copolymer component, examples of the aforementioned another unsaturated monomer include water-soluble or hydrophobic unsaturated monomers, and the like, such as β-acryloyl oxypropionic acid, methacrylic acid, maleic acid (or maleic anhydride), fumaric acid, crotonic acid, itaconic acid, vinyl sulfonic acid, 2-(meth)acrylamide-2-methylpropanesulfonate, (meth)acryloxyalkane sulfonic acids and its alkaline metal salts, its ammonium salts, alkylaminic acid, N-vinyl-2-pyridone, N-viniyl acetamide, (meth)acrylamide, N-isopropyl(meth)acrylamide, N,N-dimethyl(meth)acrylamide, 2-hydroxyethyl(meth)acrylate, methoxypolyethylene glycol(meth)acrylate, polyethylene glycol(meth)acrylate, isobutylene, lauryl(meth)acrylate, and the like. These monomers may be used either independently or in a suitable combination of two or more kinds. As the monomer of the present invention, each of the foregoing monomers may be used as a copolymer component.

Note that, in case of using an unsaturated monomer having an acid group as the unsaturated monomer and another unsaturated monomer, its salt may be an alkaline metal salt, an alkaline earth metal salt, or an ammonium salt. It is preferable to use an alkaline metal salt. Meanwhile a sodium salt or a potassium salt is preferable above all because (i) the sodium salt and potassium salt are easily obtained industrially, (ii) the sodium salt and potassium salt are harmless, and (iii) use of the sodium. salt and/or potassium salt gives better property to the water absorbent resin obtained.

In case where the aforementioned another unsaturated monomer is additionally used, the monomer other than acrylic acid (salt) is preferably 0 to 30 mol %, more preferably 0 to 10 mol %, and most preferably 0 to 5 mol %, with respect to a total number of moles of all the unsaturated monomers used to obtain the water absorbent resin. In other words, it is preferable that a total number of moles of acrylic acid and its salt that are used as main components is 70 to 100 mol %, preferably 90 to 100 mol %, more preferably 95 to 100 mol % with respect to a total number of moles of all the unsaturated monomers used to obtain the water absorbent resin.

Further, it is preferable that the acid-group-containing unsaturated monomer such as an acrylic acid is around neutral in terms of a property and pH, and it is preferable that the acid group is neutralized. A neutralizing ratio of the acid group (mol % of neutralized acid groups in all the acid groups) is generally 20 to 100 mol %, preferably 30 to 95 mol %, more preferably 40 to 80 mol %. The acid group may be neutralized by a monomer, or a polymer, or a combination thereof.

<Cross-Linking Monomer (Internal Cross-Linking Agent)>

The water absorbent resin of the present invention is a cross-linking polymer having an internally cross-linking structure. When the water absorbent resin has water-insolubility and a water-swelling property, it is regarded as having an internally cross-linking structure. Thus, the internally cross-linking structure of the water absorbent resin may be obtained by causing an unsaturated monomer to be self-cross-linked without using a cross-linking monomer. However, it is more preferable that the water absorbent resin is obtained by copolymerizing or reacting the unsaturated monomer with the cross-linking monomer. Here, the cross-linking monomer which functions as an internal cross-linking agent has two or more polymerizable unsaturated groups contained or has two or more reactive groups in its molecule.

Examples of such an internal cross-linking agent includes N,N'-methylenebis(meth)acrylamide, (poly)ethyleneglycoldi(meth)acrylate, (poly)propyleneglycoldi(meth)acrylate, trimethylolpropanetri(meth)acrylate, glycerin tri(meth)acrylate, glycerin acrylatemethacrylate, ethyleneoxide denatured trimethylolpropanetri(meth)acrylate, pentaerythritolhexa(meth)acrylate, triallyl cyanurate, triallyl isocyanurate, triallyl phosphate, triallyl amine, poly(meth)allyloxyalkane, (poly) ethyleneglycoldiglycidylether, glyceroldiglycidylether, ethylene glycol, polyethylene glycol, propylene glycol, glycerine, pentaerythritol, ethylenediamine, ethylene carbonate, propylene carbonate, polyethyleneimine, and glycidyl(meth) acrylate, and the like.

These internal cross-linking agents may be used either independently or in a suitable combination of two or more kinds. The internal cross-linking agent may be added to the reaction system either at once or in separate doses. When using one or more internal cross-linking agents, it is preferable that a cross-linking monomer including not less than two polymerizable unsaturated groups is always used for the polymerization, taking into account the absorption characteristics or other properties of the product water absorbent.

For desirable properties of the water absorbent resin, the amount of internal cross-linking agent used is preferably 0.001 to 2 mol %, more preferably 0.005 to 0.5 mol %, further preferably 0.01 to 0.2 mol %, and particularly preferably 0.03 to 0.15 mol %, all with respect to a total number of moles of all the unsaturated monomers used to obtain the water absorbent resin (excluding the cross-linking agent). In case where the amount of the internal cross-linking agent to be added is less than 0.001 mol %, or in case where the amount is more than 2 mol %, there is a possibility that a sufficient absorbent property cannot be attained, so that this is not preferable.

When the internal cross-linking agent is used to form a cross-linked structure inside the water absorbent resin, the internal cross-linking agent is added to the reaction system before, during, or after the polymerization of the unsaturated monomer, or after the neutralization of the unsaturated monomer or the polymer.

<Polymerization Initiator>

The water absorbent resin of the present invention is obtained by using a polymerization initiator in polymerizing the unsaturated monomer. As the polymerization initiator, for example, a radical polymerization initiator such as potassium persulfate, ammonium persulfate, sodium persulfate, potassium peracetic, sodium peracetic, potassium percarbonate, sodium percarbonate, t-butylhydroperoxide, hydrogen peroxide, and 2,2'-azobis(2-amidino-propane)dihydrochloride, or a photopolymerization initiator such as 2-hydroxy-2-methyl-1-phenyl-propane-1-one may be used.

It is preferable that an amount of the polymerization initiator is usually in a range of 0.001 mol % to 2 mol %, and preferably in a range of 0.01 mol % to 0.1 mol % with respect to the total number of moles of all the unsaturated monomers used to obtain the water absorbent resin, in terms of properties. If the polymerization initiator is less than 0.001 mol %, an amount of monomer not reacted and left over (residual monomer) is increased. On the other hand, if the amount of the polymerization initiator is more than 2 mol %, it becomes difficult to control the polymerization. Thus, neither of the amount of the polymerization initiator less than 0.001 mol % nor the amount more than 2 mol % is preferable.

<Polymerization Method>

For the polymerization of the monomer (unsaturated monomer, another unsaturated monomer, and cross-linking polymer) to obtain the water absorbent resin of the present invention, aqueous solution polymerization, reversed suspension polymerization, bulk polymerization or precipitation polymerization may be performed. However, in consideration of the performance of the water absorbent resin, controllability of polymerization, and absorption characteristics of a swelling gel, more preferable methods of polymerization are aqueous polymerization and reversed suspension polymerization, using an aqueous solution of the monomer.

When an aqueous solution of the monomer is used, the concentration of the monomer in the aqueous solution (hereinafter, "monomer aqueous solution") is determined in accordance with a temperature of the solution and a type of the monomer and hence is not limited to any particular value. However, the concentration is usually within 10 to 80 wt %, preferably 10 to 70 wt %, and more preferably 20 to 60 wt %. Further, in case of performing the aqueous solution polymerization, a solvent other than water may be additionally used as required, and a kind of the solvent additionally used is not particularly limited.

The polymerization of the monomer is initiated by using the aforementioned polymerization initiator. Besides the polymerization initiator, an activating energy ray, such as ultraviolet ray, an electron ray, and a γ ray, may be used solely or in combination with the polymerization initiator. Note that, which temperature the polymerization is initiated is selected as required depending on which kind of polymerization initiator is used. However, it is preferable that the polymerization is initiated at a temperature in a range of 15° C. to 130° C., and it is more preferable that the polymerization is initiated at a temperature in a range of 20° C. to 120° C. If the polymerization is initiated at temperature out of the ranges, there is a possibility that the amount of residual monomer is increased or self-cross-linkage excessively takes place thereby causing the water absorbent resin to have a low water absorbent property.

Note that, the reverse phase suspension polymerization is a polymerization method that is carried out by suspending the monomer aqueous solution in a hydrophobic organic solvent. For example, the reverse phase suspension polymerization is described in documents such as U.S. Pat. Nos. 4,093,776, 4,367,323, 4,446,261, 4,683,274, and 5,244,735, for example.

Further, the aqueous solution polymerization is a polymerization method in which the polymerization is carried out by using the monomer aqueous solution without using a dispersion solvent. For example, the aqueous solution polymerization is described in documents such as U.S. Pat. Nos. 4,625,001, 4,873,299, 4,286,082, 4,973,632, 4,985,518, 5,124,416, 5,250,640, 5,264,495, 5,145,906, and 5,380,808, and documents such as European Patent No. 0,811,636, No. 0,955,086, and No. 0,922,717. Also the monomers and the polymerization initiators recited in U.S. Patents and European Patents can be applied to the present invention.

<Drying>

In general, the polymer obtained by polymerizing a monomer in accordance with the foregoing polymerization method is a cross-linked polymer in a form of a water-containing gel-form cross-linked polymer. If necessary, the water-containing gel-form cross-linked polymer is dried or pulverized. In case of performing water soluble polymerization, it is general that the cross-linked polymer is pulverized before or after drying the water-containing gel-form cross-linked polymer.

Further, various drying methods that can be adopted here are drying by heating, hot air drying, drying under reduced pressure, infrared drying, microwave drying, drying by azeotropy with a hydrophobic organic solvent, high humidity drying in which a high temperature steam is used, and the like drying methods, attaining the target moisture content. In this manner, the drying is not particularly limited. In case where the hot-air drying is adopted in the drying, the hot-air drying is carried out usually with hot air whose temperature is in a range of 60° C. to 250° C., preferably in a range of 100° C. to 220° C., and more preferably in a range of 120° C. to 200° C. How long the drying is carried out (drying time) depends on how much surface area and moisture content the polymer has and which type of a dryer is used, so that the drying time is so set, as required, that the polymer will have a target moisture content after drying, for example, the drying time is set to be within a range from one minute to 5 hours as required.

The moisture content of the water absorbent resin that can be obtained by the drying is not particularly limited (as the term is used herein, the "moisture content" is defined by the amount of water contained in the water absorbent resin as measured by the proportion of the lost weight after drying in the mass of the water absorbent resin before drying when 1 g of the water absorbent resin is dried for 3 hours at 180° C.). However, for better property of the particulate water absorbing agent of the present invention which contains the water absorbent resin as a main component, it is preferable to control the moisture content so that the polymer is in a powder form and flowable even at room temperatures. That is, the particulate water absorbing agent has a moisture content generally in a range of 0 to 30 wt %, more preferably in a range of 0.2 to 30 wt %, further preferably in a range of 0 to 20 wt %, still further preferably in a range of 0 to 15 wt %, especially preferably in a range of 0.3 to 15 wt %, most preferably in a range of 0.5 to 10 wt %. Thus, it is preferable to obtain the water absorbent resin by drying the water-containing gel-form cross-linked polymer so as to obtain the particulate water absorbing agent having the moisture content in the foregoing range. When the moisture content is high, the fluidity drops, which may result not only in production trouble but also in such disadvantages: the water absorbent resin cannot pulverized; and it is impossible to achieve a specific particle size distribution.

Note that, in case where the polymerization is carried out by the reverse phase suspension polymerization, the water-containing gel-form cross-linked polymer obtained after polymerization reaction may be dried without pulverization as follows. That is, the water-containing gel-form cross-linked polymer is dispersed in an organic solvent of a hydrocarbon such as hexane and the like, and azeotropically dried so that the water-containing gel-form cross-linked polymer has a moisture content of 40 wt % or less (lower limit is 0 wt %, preferably, 5 wt %), and preferably 30 wt % or less. After that, the water-containing gel-form cross-linked polymer is separated by decantation or volatilization, thereby drying the water absorbent resin as required. Further, in the water absorbent resin of the present invention, a macromolecule additive described later can be added and mixed during or after the polymerization. In case of adding and mixing the macromolecule additive after the polymerization, the macromolecule additive can be added and mixed before or after the polymerization, or after pulverizing the water absorbent resin.

<Surface Cross-linking Treatment (Referred to Also as Surface Cross-linking)>

The water absorbent resin used in the particulate water absorbing agent of the present invention can be obtained by performing the cross-linking polymerization and the drying and by performing the pulverization as required, and it is preferable to perform a step of cross-linking (secondary cross-linking) a surface of the water absorbent resin so as to enhance the cross-linking density in a vicinity of a surface of the water absorbent resin. Hereinafter, both the water absorbent resin which has been subjected to the surface cross-linking treatment and the water absorbent resin which has not been subjected to the surface cross-linking treatment are referred to as a water absorbent resin.

There are various kinds of surface cross-linking agents for cross-linking the surface. For attaining better properties of the obtained water absorbent resin, it is general to use the following cross-linking agents: (a) multivalent alcohol compounds, (b) epoxy compounds, (c) multivalent amine compounds, (d) products of compressibility rate of the multivalent amine compounds with haloepoxy compounds, (e) oxazoline compounds, (f) mono, di, or poly oxazolidine compounds, (g) multivalent metal salts, (h) alkylene carbonate compounds, (i) and the like.

More specifically, it is preferable to use the surface cross-linking agents listed up in U.S. Pat. Nos. 6,228,930, 6,071,976, and 6,254,990, for example. That is, the surface cross-linking agent may be (a) multivalent alcohol compounds such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,3-butanediol, 1,5-pentanediol, 1,6-hexanediol, 1,2-cyclohexanedimethanol, sorbitol, and the like; (b) epoxy compounds such as ethylene glycol diglycidyl ether, glycidol, and the like; (c) multivalent amine compounds such as ethylenediamine, diethylenetriamine, triethylenetetramine, tetraethylenepentamine, pentaethylenehexamine, polyethyleneimine, polyamidepolyamine and the like; (d) haloepoxy compounds such as epichlorohydrin, epibromohydrin, α-methylepichlorohydrin, and the like; (e) products of compressibility rate of the multivalent amine compounds with the haloepoxy compounds; (f) oxazolidione compounds such as 2-oxazolidione and the like; (g) alkylenecarbonate compounds such as ethylene carbonate and the like; (h) and the like. However, the surface cross-linking agent is not limited to them. These surface cross-linking agents may be used independently or in a suitable combination of two or more kinds. For attaining better properties of the water absorbent resin, it is preferable to use at least one of the multivalent alcohols among the cross-linking agent. It is preferable that the multivalent alcohols to be used have two to ten carbons in its molecule, and preferably three to eight carbons in its molecule.

An amount of the surface cross-linking agent depends on which type of the surface cross-linking agent is used, or how the compounds used are combined with each other. However, the amount of the surface cross-linking agent is preferably in a range of 0.001 parts to 10 parts by weight, and more preferably in a range of 0.01 parts to 5 parts by weight, with respect to 100 parts by weight (mass) of the water absorbent resin.

In performing the surface cross-linking treatment, it is preferable to use water in combination with the surface cross-linking agent. In this case, an amount of the water to be used depends on how much moisture content of the water absorbent precursor to be used has. In general, with respect to 100 parts by weight of the water absorbent resin precursor, the amount of the water to be used is in a range of 0.5 parts to 20 parts by weight, and preferably 0.5 parts to 10 parts by weight.

It is possible to use a hydrophilic organic solvent other than water, and it is possible to use a mixed solvent of water and hydrophilic organic solvent. An amount of the hydrophilic organic solvent or the mixed solvent to be used is in a range of 0 part to 10 pars by weight, preferably in a range of 0 part to 5 parts by weight, and more preferably in a range of 0 part to 3 parts by weight with respect to 100 parts by weight of the water absorbent resin precursor.

Various methods can be adopted in adding the surface cross-linking agent, but the following mixing method is preferable: in advance, the surface cross-linking agent is mixed with water and/or the hydrophilic organic solvent as required, and the mixture is dropped to the water absorbent resin. And the following method is more preferable: in advance, the surface cross-linking agent is mixed with water and/or the hydrophilic organic solvent as required, and the mixture is sprayed to the water absorbent resin. An average diameter of liquid droplets to be sprayed is preferably 0.1 to 300 μm, and more preferably 1 to 200 μm.

As to a mixing device for use in mixing the water absorbent resin, the surface cross-linking agent, and water or the hydrophilic organic solvent, it is preferable that the mixing device has a large mixing power in order that these compounds are mixed evenly and thoroughly. Examples of mixing devices that can be preferably used as the mixing device are: a cylindrical mixer, double-wall conical mixer, a high-speed stirring mixer, a V-shaped mixer, a ribbon blender, a screw mixer, a double-arm kneader, a crush-type kneader, a rotary mixer, an air current mixer, a turbulizer, batch-type Lödige mixer, continuous Lödige mixer, and the like apparatuses.

Note that, in case of mixing the surface cross-linking agent, a macromolecule additive, whose lateral chain has a hydrocarbon radical containing seven or more carbons in its molecule, is mixed or is made to coexist before the surface cross-linking, thereby obtaining the particulate water absorbing agent resin of the present invention. Note that, the macromolecule additive will be described later. Further, in case of mixing the surface cross-linking agent, water-insoluble fine powder may be made to coexist so as not to prevent the effect of the present invention.

After mixing the surface cross-linking agent with the water absorbent resin precursor, it is preferable that the water absorbent resin is subjected to a heat treatment. Conditions of the heat treatment are: a water absorbent resin or a heating medium used to perform the heat treatment preferably has a temperature in a range of 100° C. to 250° C., and more preferably in a range of 150° C. to 250° C.; and a heating time in the heat treatment is preferably in a range of one minute to two hours. Examples of appropriate combinations of the heating temperature and heating time are: (a) 180° C. for 0.1 to 1.5 hours, and (b) 200° C. for 0.1 to one hours.

Note that, in case where the water absorbent resin is prepared by the reverse phase suspension polymerization, it is possible to obtain a water absorbent resin, whose surface has been cross-linked, by dispersing the surface cross-linking agent in a hydrophobic organic solvent used in the reversed suspension polymerization, for example, in such a manner that the water-containing gel-form cross-linked polymer has a moisture content of not more than 50 wt %, preferably not more than 40 wt %, and more preferably not more than 30 wt %, during and/or after the azeotropical drying.

Further, another example of the surface cross-linking treatment of the present invention is as follows: after adding a treatment liquid containing a radical polymerization compound to the water absorbent resin, active energy is emitted thereto, so as to carry out the surface treatment. For example, such a technique is recited in Japanese Publication for Unexamined Patent Application, Tokugan 2003-303306 (publication date: Aug. 27, 2003). The surface treatment can be carried out by adding the surfactant to the treatment liquid recited in this publication and by emitting active energy thereto.

Further, another example of the surface cross-linking treatment of the present invention is as follows: after adding an aqueous solution containing peroxide radical initiator to the water absorbent resin, thus obtained resultant is heated, so as to carry out the surface treatment. For example, such a technique is recited in Japanese Publication for Unexamined Patent Application, Tokukohei 7-8883 (publication date: Feb. 1, 1995).

As described above, it is preferable that the water absorbent resin of the present invention that is subjected to the surface cross-linking treatment as required is adjusted to have a specific particle diameter (particle size) for higher fluidity at the time of moisture absorption and a higher bulk density.

Note that, the particle diameter of the water absorbent resin is applicable also to the particulate water absorbing agent described later, so that specific description thereof is omitted here. Further, the particle diameter of the water absorbent resin or the particulate water absorbing agent may be adjusted by further granulation performed by adding and mixing insoluble fine particles and a hydrophilic solvent, preferably water, depending on its purpose and necessity.

The particulate water absorbing agent of the present invention, described later, preferably includes: the water absorbent resin obtained in the foregoing manner; and a powder lubricant or a surfactant. Embodiment 1 describes a case where the powder lubricant is a macromolecule additive whose lateral chain has a hydrocarbon group containing seven or more carbons in its molecule.

(II) Powder Lubricant and Surfactant

Embodiment 1

<Macromolecule Additive>

1. Composition of the Macromolecule Additive

The macromolecule additive which can be used in the present invention is a macromolecule compound obtained by (co)polymerizing a monomer whose lateral chain has a hydrocarbon group containing seven or more carbons in its molecule, or is a macromolecule compound obtained by introducing a hydrocarbon group, containing seven or more carbons in its molecule, into a lateral chain of a macromolecule compound having a reactive group.

The hydrocarbon group has a hydrocarbon unit, constituted of carbon and hydrogen, which has seven or more carbons in its molecule. It does not matter whether its structure is a straight chain, or a branched chain, or a cyclic chain. It does not matter whether the structure is in a saturated state or in an unsaturated state. Particularly, when an unsaturated hydrocarbon unit such as an undecylenyl group or the like is used, it is possible to give further effects such as addition of an antibacterial property.

The monomer whose lateral chain has the hydrocarbon group is a monomer in which a hydrocarbon group hangs from a main chain of a macromolecule compound when polymerized. Note that, in the present invention, a branch occurring in the polymerization is not regarded as the lateral chain. That is, a branch in polyolefin of a copolymer based on a high-pressure polyolefin (polyethylene, polypropylene, and the like) synthesis process are not regarded as the lateral chain. Examples of the copolymer include: an ethylene-acrylic acid copolymer; an ethylene-maleic anhydride copolymer; an ethylene-vinyl acetate copolymer; a propylene-acrylic acid copolymer; a propylene-maleic anhydride copolymer; propylene-vinyl acetate copolymer; and the like.

In these compounds, a polymer structure is not exactly controlled, so that a large quantity of additive is required in improving the fluidity at the time of moisture absorption, This is not economically preferable.

The number of carbons contained in the lateral chain of the hydrocarbon group is preferably 7 or more, more preferably 8 or more, still more preferably 10 or more, particularly preferably 12 or more, and most preferably 14 or more. Further, an upper limit of a length of the hydrocarbon group is not particularly limited, but is preferably 50 or less, more preferably 40 or less, most preferably 30 or less.

Further, the monomer used as the macromolecule additive of the present invention has a lateral chain having a hydrocarbon group containing seven or more carbons in its molecule, and may be such that its lateral chain has a polyoxyethylene group, a polyoxypropylene group, or the like. Thus, the monomer whose lateral chain has a hydrocarbon group containing seven or more carbons in its molecule may be water-soluble or water-insoluble.

The water-soluble monomer (hydrophilic monomer) of the present invention is a monomer whose solubility in 100 g of water at 20° C. is 1 g or more, preferably 5 g or more, more preferably 10 g or more, most preferably 20 g or more.

The water-insoluble monomer of the present invention is a monomer whose solubility in 100 g of water at 20° C. is less than 1 g (lower limit is 0 g), preferably 0.5 g or less, more preferably 0.1 g or less.

An example of the monomer whose lateral chain has a hydrocarbon group containing seven or more carbons in its molecule is an ester or amide monomer obtained by reacting an alcohol or an amine having a branched chain or a cyclic chain of a hydrocarbon group containing seven or more carbons in its molecule with an ethylene unsaturated monomer containing a carboxyl group. Typical examples of such monomer include: (meth)acrylic esters such as 2-ethyl-hexyl (meth)acrylate, lauryl(meth)acrylate, stearyl(meth)acrylate, isostearyl(meth)acrylate, palmityl(meth)acrylate, myristyl (meth)acrylate, capryl(meth)acrylate, cetyl(meth)acrylate, isobonyl(meth)acrylate, undecylenyl(meth)acrylate, and oleyl(meth)acrylate; and alkylation(meth)acrylamides such as 2-ethyl-hexyl(meth)acrylamide, lauryl(meth)acrylamide, stearyl(meth)acrylamide, isostearyl(meth)acrylamide, palmityl(meth)acrylamide, myristyl(meth)acrylamide, capryl(meth)acrylamide, cetyl(meth)acrylamide, isobonyl (meth)acrylamide, undecylenyl(meth)acrylamide, and oleyl (meth)acrylamide. Further, a similar ester or amide monomer obtained by reacting maleic acid, fumaric acid, crotonic acid, itaconic acid is included.

Further, the monomer may be an ester monomer obtained by reacting carboxylic acid whose straight chain or a branched chain or a cyclic chain has a hydrocarbon group containing seven or more carbons in its molecule with an ethylene unsaturated monomer having a hydroxyl group. Typical examples of such monomer include vinyl esters such as caprylic vinyl, capric vinyl, lauric vinyl, myristate vinyl, palmitic vinyl, stearic vinyl, isostearic vinyl, undecylate vinyl, behenic vinyl, naphthenic vinyl, linoleic vinyl, linolenic vinyl, and the like. Further, a similar ester monomer obtained by reacting hydroxy(meth)acrylate or polyethyleneglycol(meth)acrylate and the like is included. Particularly, a compound having an unsaturated hydrocarbon group portion as a hydrocarbon group containing seven or more carbons in its molecule has an antibacterial property. Examples thereof are undecylenoxy polyethylene glycol(meth)acrylate and the like. This is particularly favorably used.

Further, the monomer may be an amide monomer obtained by reacting a carboxylic acid whose straight chain or a branched chain or a cyclic chain has a hydrocarbon group containing seven or more carbons in its molecule with an ethylene unsaturated monomer containing an amino group. Typical examples of such monomer include vinyl amides such as caprylic acid-N-vinyl amide, capric acid-N-vinyl amide, lauric acid-N-vinyl amide, myristic acid-N-vinyl amide, palmitic acid-N-vinyl amide, stearic acid-N-vinyl amide, isostearic acid-N-vinyl amide, palmitic acid-N-vinyl amide, undecylenic acid-N-vinyl amide, behenic acid-N-vinyl amide, naphthenic acid-N-vinyl amide, linoleic acid-N-vinyl amide, and linolenic acid-N-vinyl amide.

Further, the monomer may be (i) a halide whose straight chain or a branched chain or a cyclic chain containing a hydrocarbon group containing seven or more carbons in its molecule, (ii) a quaternary salt monomer obtained by reacting an alcohol or a carboxylic acid with an ethylene unsaturated monomer containing an amino group, (iii) a neutralized salt, or (iv) an amine. Typical examples of such monomer are (a) a quaternary salt having heptyl, octyl, 2-ethyl hexyl, nonyl, lauryl, palmityl, stearyl, isostearyl, undecylenyl, behenyl, naphthyl, oleyl, cetyl, isobonyl groups, and the like, (b) a neutralized salt having heptyl, octyl, 2-ethyl hexyl, nonyl, lauryl, palmityl, stearyl, isostearyl, undecylenyl, behenyl, naphthyl, oleyl, cetyl, isobonyl groups, and the like, and (c) an amine having heptyl, octyl, 2-ethyl hexyl, nonyl, lauryl, palmityl, stearyl, isostearyl, undecylenyl, behenyl, naphthyl, oleyl, cetyl, isobonyl groups, and the like (e.g., dialkylamino alkyl(meth)acrylate, dialkylamino alkyl(meth)acrylamide, vinyl amine, arylamine, and ethylene imine).

Further, the monomer may be an ester monomer obtained by reacting an alcohol whose straight chain or branched chain or cyclic chain having a hydrocarbon group containing seven or more carbons in its molecule with an ethylene unsaturated monomer containing a sulfonic acid group and a phosphate group. Examples thereof include: heptyl ester, octyl ester, 2-ethylhexyl ester, nonyl ester, lauryl ester, palmityl, ester, stearyl ester, isostearyl ester, undecylenyl ester, behenyl ester, naphthyl ester, oleyl ester, isobonyl ester, cetyl ester, and the like, that are obtained by reacting vinyl sulfonic acid; heptyl ester, octyl ester, 2-ethylhexyl ester, nonyl ester, lauryl ester, palmityl, ester, stearyl ester, isostearyl ester, undecylenyl ester, behenyl ester, naphthyl ester, oleyl ester, isobonyl ester, cetyl ester, and the like, that are obtained by reacting styrene sulfonic acid; heptyl ester, octyl ester, 2-ethylhexyl ester, nonyl ester, lauryl ester, palmityl, ester, stearyl ester, isostearyl ester, undecylenyl ester, behenyl ester, naphthyl ester, oleyl ester, isobonyl ester, cetyl ester, and the like, that are obtained by reacting 2-(meth)acrylamide-2-methylpropanesulfonic acid; heptyl ester, octyl ester, 2-ethylhexyl ester, nonyl ester, lauryl ester, palmityl, ester, stearyl ester, isostearyl ester, undecylenyl ester, behenyl ester, naphthyl ester, oleyl ester, isobonyl ester, cetyl ester, and the like, that are obtained by reacting (meth)acryloxyalkane sulfonic acid; and the like.

Further, the monomer may be α-olefin whose lateral chain has a straight-chain or branched-chain or cyclic-chain hydrocarbon group containing seven or more carbons in its molecule. Examples thereof are 1-nonene, 1-decene, 1-octadecene, and the like. These monomer may be solely used or may be used in combination of two or more kinds.

As in the case of (co)polymerization, examples of the macromolecule additive include also a macromolecule compound whose lateral chain has a hydrocarbon group, containing seven or more carbons in its molecule, which is obtained by subsequently reacting a hydrocarbon group containing seven or more carbons in its molecule with a carboxyl group, an amino group, a hydroxyl group, a sulfonic acid group, a phosphate group, and the like of a macromolecule compound.

That is, it is possible to obtain a macromolecule additive whose lateral chain has a hydrocarbon group containing seven or more carbons in its molecule by reacting an alcohol, a carboxylic acid, an amino group, a hydroxyl group, a sulfonic acid, an amine, and the like, each having a hydrocarbon group containing seven or more carbons in its molecule, with a macromolecule compound having reactive groups such as a carboxyl group, an amino group, a hydroxyl group, a sulfonic acid group, a phosphate group.

In case where the lateral chain of the macromolecule additive has no hydrocarbon group containing seven or more carbons in its molecule, it is impossible to sufficiently secure the fluidity of the particulate water absorbing agent, obtained by adding the macromolecule additive to the water absorbent resin, at the time of moisture absorption, and also the fluidity in the dry state drops, so that there occur such problems that: it becomes hard to treat the particulate water absorbing agent; a surface tension of the absorbed liquid drops which results in a larger re-wet amount when the particulate water absorbing agent is used in a disposable diaper, an absorbent core, and the like.

In case of obtaining the macromolecule additive by carrying out the (co)polymerization, the (co)polymerization is carried out under such condition that an amount of the monomer whose lateral chain has a hydrocarbon group containing seven or more carbons in its molecule is preferably 15 wt % or more and 100 wt % or less, more preferably 20 wt % or more and 85 wt % or less, still more preferably 20 wt % or more and 70 wt % or less, with respect to the (co)polymer which is the macromolecule additive.

In case of obtaining the macromolecule additive by subsequently introducing a hydrocarbon group containing seven or more carbons in its molecule into a macromolecule compound having a reactive group, as in the case of the copolymerization, an amount of the monomer is preferably 15 wt % or more and 100 wt % or less, more preferably 20 wt % or more and 85 wt % or more, still more preferably 20 wt % or more and 70 wt % or less, with respect to the (co)polymer which is the macromolecule additive, in terms of a recurring unit (monomer unit). The phrase "in terms of a recurring unit (monomer unit)" means that the amount of the monomer is calculated as follows: in case where a stearyl alcohol is reacted with a polyacrylic acid for example so as to obtain the macromolecule additive whose lateral chain has a stearyl group, thus obtained resultant is regarded as a copolymer of an acrylic acid and stearyl acrylate, and the amount is calculated at a ratio (mass) of the monomer (stearylate), containing a stearyl group, with respect to a polymer which is the macromolecule additive.

When the amount of the monomer whose lateral chain has a hydrocarbon group containing seven or more carbons in its molecule is out of the foregoing range, an additional amount is likely to be larger in improving (i) the fluidity of the particulate water absorbing agent, obtained by adding the macromolecule additive to the water absorbent resin, at the time of moisture absorption and (ii) the fluidity in the dry state. Such arrangement is not economically preferable.

As long as the lateral chain of the macromolecule additive has a hydrocarbon group containing seven or more carbons in its molecule, any monomer can be used.

Specifically, a monomer whose lateral chain has a hydrocarbon group containing less than seven carbons or a water-soluble monomer may be used. Examples of such monomer include: (meth)acrylic acid, maleic acid (maleic anhydride), fumaric acid, crotonic acid, itaconic acid, vinyl sulfonic acid, 2-(meth)acrylamide-2-methylpropane sulfonic acid, (meth) acryloxyalkane sulfonic acid; esters obtained by reacting the foregoing acids; amide, N-vinyl-2-pyrrolidone, N-vinyl acetamide, (meth)acrylamide, N-isopropyl(meth)acrylamide, N,N-dimethyl(meth)acrylamide, 2-hydroxyethyl (meth)acrylate, methoxypolyethyleneglycol(meth)acrylate, polyethyleneglycol(meth)acrylate, isobutylene, and the like. These monomers may be used independently or in a suitable combination of two or more kinds as required.

In order to control hydrophilic/hydrophobic properties of a surface of the particulate water absorbing agent, it is preferable to use a macromolecule additive obtained by (co)polymerizing not only the monomer whose lateral chain has a hydrocarbon group containing seven or more carbons in its molecule but also a water-soluble monomer. As the water-soluble monomer, it is preferable to use (meth)acrylic acid, (meth)acrylamide, N-vinyl-2-pyrrolidone, 2-hydroxyethyl (meth)acrylate, methoxypolyethyleneglycol(meth)acrylate, polyethyleneglycol(meth)acrylate.

It is preferable that the macromolecule additive is obtained by copolymerizing both the water-insoluble monomer (hydrophobic) and the water-soluble monomer (hydrophilic), and a mass ratio of the water-insoluble monomer and the water-soluble monomer preferably ranges from 15:85 to 85:15, more preferably ranges from 20:80 to 80:20, still more preferably ranges from 20:80 to 70:30, most preferably ranges from 20:80 to 60:40.

The macromolecule additive obtained by copolymerizing the water-soluble and water-insoluble monomers to a macromolecule chain is added to the water absorbent resin in this manner, so that it is possible to control the degree of the hydrophilic/hydrophobic property of the particulate water absorbing agent, thereby securing the fluidity at the time of moisture absorption without lowering the water absorbent rate. Further, the macromolecule additive is copolymerized with the water-soluble monomer so as to give the hydrophilic property to the macromolecule additive, so that the macromolecule additive itself has a water-swelling property or a water-soluble property. Thus, it is possible to exhibit an antibacterial property more strongly in case where an undecylenoxy group or an amine quaternary salt which is the unsaturated hydrocarbon group is introduced.

Further, in case of using a monomer having a carboxyl group, a monomer having a sulfonic acid group, a monomer having a phosphate group, and a monomer having an amino group as a hydrophilic monomer of the macromolecule additive added to the water absorbent resin, the monomer may be in a form of a neutralized salt (alkaline metal salt, alkaline earth metal, transition metal salt, ammonium salt, halide salt, organic acid salt, diphosphate, sulfosalt, and the like). It is preferable to use a monovalent or multivalent metal salt, and examples thereof include sodium, potassium, iron, magnesium, silver, zinc, copper, tin, and the like. Particularly, a multivalent (more than bivalent) metal salt, for example, a metal ion salt such as iron, magnesium, silver, zinc, copper, tin, and the like, can give an antibacterial property and a deodorant effect, so that these metal ion salts are particularly preferable. A ratio at which the metal salt is neutralized is preferably 75 mol % or less (lower limit is 0 mol %), more preferably 50 mol % or less, still more preferably 25 mol %, most preferably 10 mol % or less, with respect to a molar number of all the carboxyl groups, sulfonic acid groups, and amino groups in the macromolecule additive. In case where the macromolecule additive in a powder state or a suspension liquid state is added to the water absorbent resin, not only the foregoing monomer but also a cross-linking monomer (referred to also as a cross-linking agent) having two or more polymerizable unsaturated groups and two or more reactive groups in its molecule may be copolymerized or reacted with each other. Specific examples of the cross-linking agent include N,N'-methylenebis(meth)acrylamide, (poly)ethyleneglycoldi(meth)acrylate, (poly)propyleneglycoldi(meth)acrylate, trimethylolpropanetri(meth)acrylate, glycerintri (meth)acrylate, glycerinacrylatemethacrylate, ethyleneoxide denaturated trimethylolpropanetri(meth)acrylate, pentaerythritolhexa(meth)acrylate, triallyl cyanurate, triallyl isocyanurate, triallyl phosphate, triallyl amine, poly(meth)allyloxyalkane, (poly)ethyleneglycol diglycidyl ether, glycerol diglycidyl ether, ethylene glycol, polyethylene glycol, propylene glycol, glycerin, pentaerythritol, ethylenediamine, ethylenecarbonate, propylenecarbonate, polyethyleneimine, glycidyl(meth)acrylate, and the like.

These cross-linking agents may be used independently or in a suitable combination of two or more kinds as required. Further, these cross-linking agents may be collectively added to a reaction system, or may be separately added to the reaction system. It is possible to adjust the solubility of the macromolecule additive in neutral water to be soluble or insoluble on the basis of whether such cross-linking agent is contained or not or on the basis of an amount of the cross-linking agent. An amount of the cross-linking agent used is preferably 0.001 to 10 mol %, more preferably 0.005 to 5 mol %, still more preferably 0.01 to 1 mol %, with respect to the foregoing monomer (excluding an internal cross-linking agent).

A fusing point, a glass transition point, or a softening point of the macromolecule additive is preferably 40 to 250° C. or lower, more preferably 50 to 200° C., still more preferably 60 to 150° C. In case of using the macromolecule additive whose fusing point etc. is lower than 40° C., the fluidity of the particulate water absorbing agent, obtained by adding the macromolecule additive to the water absorbent resin, in the dry state or at the time of moisture absorption drops, so that it becomes hard to treat the resultant. Thus, such arrangement is not preferable. The fusing point, the glass transition point, or the softening point is adjusted in the foregoing range, so that it is possible to maintain the powder fluidity at a room temperature and the fluidity at the time of moisture absorption. In addition, after a base material such as nonwoven cloth, pulp, or the like is mixed with the particulate water absorbing agent, the macromolecule additive is heated so that its temperature exceeds its fusing point, glass transition point, or softening point, so that the base material and the particulate water absorbing agent can be thermally fused and fixed to each other. When the fusing point, the glass transition point, or the softening point of the macromolecule additive is higher than 250° C., the base material and the particulate water absorbing agent are so likely to thermally deteriorate, so that such arrangement is not preferable.

Further, as to a molecular mass of the macromolecule additive, its weight average molecular mass is generally 1,000 or more and 1,000,000 or less, preferably 5,000 or more and 1,000,000 or less, more preferably 10,000 or more and 1,000,000 or less, most preferably 50,000 or more and 1,000,000 or less. In case where the molecular mass of the macromolecule additive is out of the foregoing range, the fluidity of the particulate water absorbing agent, obtained by adding the macromolecule additive to the water absorbent resin, in the dry state and at the time of absorption may be deteriorated.

A form of the macromolecule additive in case where the macromolecule additive is added to the water absorbent resin may be a liquid state, a suspension state, or a powder state.

In case where the macromolecule additive in the powder state (fine particles) is added to the water absorbent resin, a particle diameter and a particle shape of the macromolecule additive are not particularly limited. Generally, it is preferable that: the particle diameter of the macromolecule additive is smaller than a weight (mass) average particle diameter of the water absorbent resin, and a particle diameter of 90 wt % or more (upper limit is 100 wt %) of the whole macromolecule additive powder ranges from 0.01 to 100 μm. The particle diameter of 90 wt % or more of the whole macromolecule additive powder more preferably ranges from 0.01 to 75 μm, still more preferably ranges from 5 to 75 μm, most preferably ranges from 5 to 50 μm.

Further, an average particle diameter (D50) of the macromolecule additive powder is preferably 0.01 μor more and 100 μm or less, more preferably 0.01 μm or more and 75 μm or less, most preferably 0.01 μm or more and 50 μor less. The particle diameter distribution and the average particle diameter can be easily measured in accordance with conventional measurement methods such as a Coulter counter method, a laser diffraction dispersion method, and the like. Further, thus obtained particles may be formed as granulated fine particles or primary particles (single particles).

When the particle diameter of the macromolecule additive particles (fine particles) is out of the foregoing range, the fluidity of the particulate water absorbing agent obtained by adding the macromolecule additive to the water absorbent resin is not improved in the dry state and at the time of moisture absorption, and the water absorbent property of the particulate water absorbing agent drops, so that such arrangement is not preferable.

<Synthesis Method of Macromolecule Additive>

The macromolecule additive is obtained by a method in which a monomer whose lateral chain has a hydrocarbon group containing seven or more carbons in its molecule is (co)polymerized, or a method in which a hydrocarbon group containing seven or more carbons in its molecule is introduced into a lateral chain of a macromolecule compound having reactive groups such as a carboxyl group, an amino group, a hydroxyl group, a sulfonic acid group, a phosphate group, and the like. It is preferable to adopt the method in which a monomer whose lateral chain has a hydrocarbon group containing seven or more carbons in its molecule is (co)polymerized.

As a synthesis method of the macromolecule additive in case of adding the macromolecule additive in the solution state to the water absorbent resin, any method may be adopted as long as the polymerization is carried out in a solvent which allows the foregoing monomer mixture to be solved. Examples of preferable solvent include methanol, ethanol, isopropyl alcohol, tetrahydro furan, diethyl ether, dichloromethane, acetic ether, toluene, hexane, dimethylformamide, dimethylsulfoxide, benzene, cyclohexane, water, and the like.

In the polymerization reaction, radical polymerization in which an uncombined radical is generated by light and heat is favorably used, and it is possible to additionally use a chain transfer agent such as thioglycolic acid ester, alkylmercaptan, and the like.

As a radical polymerization initiator, it is possible to use: a radical polymerization initiator such as potassium persulfate, ammonium persulfate, sodium persulfate, benzoyl peroxide, hydrogen peroxide, capryl peroxide, 2,2'-azobisisobutyronitrile, sodium peracetic, potassium percarbonate, sodium percarbonate, t-butylhydroperoxide, and 2,2'-azobis(2-amidinopropane)dichlorodihydrochloride; and a photo polymerization initiator such as 2-hydroxy-2-methyl-1-phenyl-propane-1-one, and the like. In terms of a property, an amount of the polymerization initiator is generally 0.001 to 2 mol %, preferably 0.01 to 1 mol % (with respect to the whole monomer). When the amount of the polymerization initiator is less than 0.001 mol %, a large amount of residual monomer remains unreacted. When the amount of the polymerization initiator exceeds 2 mol %, it is difficult to control the polymerization, so that such arrangement is not preferable.

The polymerization reaction temperature is adjusted preferably within a range of 0 to 125° C., and the reaction is carried out preferably for 10 minutes to 5 hours.

The concentration of the monomer in the reaction solution in case of the polymerization reaction preferably ranges from 1 to 50 wt %, more preferably ranges from 5 to 30 wt %, most preferably ranges from 10 to 25 wt %.

As the synthesis method of the macromolecule additive in case of adding the macromolecule additive in the powder state and the suspension liquid state to the water absorbent resin, it is possible to adopt a method in which thus obtained resultant is pulverized, a method in which emulsification polymerization or suspension polymerization is carried out, a method in which deposition polymerization (referred to also as dispersion polymerization) is carried out, or the like.

In the suspension polymerization and the emulsification polymerization, it is often that a surfactant is used as a dispersant, so that this may drops a surface tension of the absorbed liquid in case where the particulate water absorbing agent obtained by adding the additive to the water absorbent resin comes in contact with the absorbed liquid. Thus, it is necessary to pay attention so as not to bring about such condition. The most preferable production method of powder is the deposition polymerization.

The deposition polymerization is recited in Japanese Publication for Unexamined Patent Application, Tokukaihei 6-199969, Japanese Publication for Unexamined Patent Application, Tokukaihei 3-95204, Japanese Publication for Unexamined Patent Application, Tokukaisho 60-71623, or Radical Polymerization Handbook, page 264 (published by NTS INC. in 1999). In this polymerization method, a monomer is soluble in a solvent, but the monomer becomes insoluble in the solvent when the polymerization causes the monomer to be a macromolecule monomer, so that the monomer is deposited as fine particles, and it is possible to easily obtain the fine particles merely by removing the solvent. According to the deposition polymerization, it is possible to obtain the fine particles without using the surfactant. Thus, when the particulate water absorbing agent is obtained by adding the fine particles obtained by the deposition polymerization to the water absorbent resin, the particulate water absorbing agent hardly drops the surface tension of the absorbed liquid, so that the deposition polymerization is particularly preferable.

A type of the solvent used in the deposition polymerization varies depending on a type of the monomer, so that it is difficult to specify the solvent. However, the monomer is soluble, so that it is necessary to select a solvent which does not allow the macromolecule monomer generated by the polymerization to be solved. Typical examples of the solvent used in the deposition polymerization include: hexane, pentane; cycloalkane containing 5 to 10 carbons in its molecule, e.g., cyclohexane, benzene, or alkylation benzene; toluene, xylene, alkylcarboxylate whose alkyl group contains 1 to 6 carbons and carboxylate part contains 2 to 6 carbons, e.g., acetic ether, methyl acetate; haloalkane containing 1 to 2 carbons and two or more halogen groups, e.g., dichloroethane; and the like.

As the deposition polymerization initiator, it is possible to use: a radical polymerization initiator such as potassium persulfate, ammonium persulfate, sodium persulfate, benzoyl peroxide, hydrogen peroxide, capryl peroxide, 2,2'-azobisisobutyronitrile, sodium peracetic, potassium percarbonate, sodium percarbonate, t-butylhydroperoxide, and 2,2'-azobis(2-amidinopropane)dichlorodihydrochloride; and a photo polymerization initiator such as 2-hydroxy-2-methyl-1-phenyl-propane-1-one, and the like. In terms of a property, an amount of the polymerization initiator is generally 0.001 to 2 mol %, preferably 0.01 to 1 mol % (with respect to the whole monomer). When the amount of the polymerization initiator is less than 0.001 mol %, a large amount of residual monomer remains unreacted. When the amount of the polymerization initiator exceeds 2 mol %, it is difficult to control the polymerization, so that such arrangement is not preferable.

The concentration of the monomer in the reaction solution in case of the deposition polymerization reaction preferably ranges from 1 to 50 wt %, more preferably ranges from 5 to 30 wt %, most preferably ranges from 10 to 25 wt %. In case of carrying out the deposition polymerization with the high concentration, it is preferable that: 0.5 to 1.0 wt % of polyoxyethylene containing 2000 to 20000 molecules, specifically, 0.5 to 1.0 wt % of a copolymer or the like of ethylene oxide and propylene oxide coexists with the monomer, thereby carrying out the polymerization.

In the polymerization reaction, the deposition polymerization is carried out in any manner as long as a combined radical is generated by light or heat or redox, and the polymerization reaction temperature is adjusted preferably within a range of 0 to 125° C., and the reaction is carried out preferably for 10 minutes to 5 hours.

The deposite obtained by the polymerization may be added to the water absorbent resin without any modification, but the deposite is dried after removing an extra solvent in case of temporarily batching off the deposite as powder. It is necessary to adjust a drying temperature to be less than the fusing point, the glass transition point, or the softening point so that thus generated fine particles are not combined into a single substance. The optimal drying temperature varies depending on a type of the monomer used, so that it is difficult to specify the type of the monomer. However, the drying temperature preferably ranges from 30° C. to 200° C., more preferably ranges from 40° C. to 150° C., most preferably ranges from 50° C. to 100° C. Further, it is preferable that the drying treatment is carried out under reduced pressure. The drying treatment is carried out preferably at 100 mmHg or less, more preferably at 50 mmHg or less, most preferably at 10 mmHg or less.

After the drying treatment, pulverization treatment is carried out as required and a particle diameter of the pulverized substances is adjusted to an optimal particle diameter of the macromolecule additive powder (fine particles) in case where the macromolecule additive is an agglomerate substance.

The macromolecule additive, used in the present invention, whose lateral chain has a hydrocarbon group containing seven or more carbons in its molecule, may be in a liquid state, a suspension state, or a powder state.

In case where the macromolecule additive in a liquid state or in a suspension state is added to the water absorbent resin, it is possible to adopt (i) a method in which: the macromolecule additive is dissolved or dispersed, in a slurry manner, in a surface cross-linking agent solution obtained by mixing the surfactant, water, and/or the hydrophilic organic solvent, that are used in the aforementioned surface cross-linking treatment, so as to be mixed with the water absorbent resin, and (ii) a method in which: the macromolecule additive is dissolved or dispersed, in a slurry manner, in water and/or the hydrophilic organic solvent, so as to be mixed with the water absorbent resin.

As described above, in case of mixing the macromolecule additive in the solution state or in the suspension state with the water absorbent resin, an optimal amount of the solvent constituted of water and/or the hydrophilic organic solvent varies depending on a type and a particle diameter (particle size) of the water absorbent resin. However, in case where water is used as the solvent, the amount of the solvent added is 10 weight parts or less, preferably 1 to 5 weight parts, with respect to 100 weight parts of a solid component of the water absorbent resin. Further, in case where a hydrophilic solvent is used as the solvent, the amount of the solvent added is 10 weight parts or less, preferably 0.1 to 5 weight parts, with respect to 100 weight parts of a solid component of the water absorbent resin.

The concentration of the macromolecule additive dissolved or dispersed (suspended) in the foregoing solvent is set depending on a type and a viscosity of the macromolecule compound used, and is not particularly limited. However, the concentration of the macromolecule additive generally ranges from 0.001 to 30 wt %, preferably ranges from 0.01 to 10 wt %, with respect to a total amount of the macromolecule additive and the solvent.

In case of adding the macromolecule additive in the powder state to the water absorbent resin, it is possible to adopt a method in which the water absorbent resin and the powder macromolecule additive are directly mixed by dry-blending, and a method in which water is added after the direct mixing so as to fix the macromolecule additive to a surface of the water absorbent resin.

Also in case where the polymerization reaction is carried out directly in a surface of the water absorbent resin so that the macromolecule additive is formed so as to obtain the particulate water absorbing agent resin as in a method 5 described later, it is possible to adopt the same method as the method in which the macromolecule additive is added with solution. Further, as to the polymerization method, an uncombined radical is generated by light or heat. In order to realize this condition, the polymerization method of the macromolecule additive which was described in the foregoing Item (II) is adopted as required.

A powder temperature of the water absorbent resin in mixing the macromolecule additive with the water absorbent resin is a normal temperature. However, in order to obtain the stable water absorbent property and the stable fluidity of the particulate water absorbing agent at the time of moisture absorption, the macromolecule additive and the water absorbent resin are mixed with each other preferably at 5° C. to 100° C., more preferably at 20° C. to 80° C.

That is, in the particulate water absorbing agent of the present invention, an amount of the macromolecule additive varies depending on the desired fluidity at the time of moisture absorption and the desired water absorbent property. However, the amount of the additive used preferably within a range of 0 weight part or more to 30 weight parts or less, more preferably within a range of 0.01 weight part to 20 weight parts, still more preferably within a range of 0.01 weight part to 10 weight parts, particularly preferably within a range of 0.01 weight part to 5 weight parts, most preferably within a range of 0.01 weight part to 3 weight parts. In case where the amount of the additive used exceeds the foregoing range, the fluidity at the time of moisture absorption cannot be sufficiently improved irrespective of the amount of the additive used. This is not economical. Moreover, this may result in drop of the water absorbent property.

In the present invention, any ordinary mixer can be used to mix the water absorbent resin with the macromolecule additive. Examples include cylindrical mixers, screw mixers, screw extruders, turbulizers, nauta mixers, V-shaped mixers, ribbon blenders, double-arm kneaders, flow mixers, air current mixers, rotary disc mixers, roll mixers, and convolution mixers. The mixing rate is of any value.

Embodiment 2

<Surfactant>

In the present invention, a surfactant was used as an essential component of the surface treatment agent in performing the surface cross-linking treatment, so as to produce the particulate water absorbing agent. In the present invention, the surfactant is an agent having a hydrophilic property and an oleophilic property (hydrophobic property) in its molecule, and is strongly adsorbed to a surface of a substance due to a balance of the hydrophilic property and the oleophilic property, and reforms a surface property of the substance. Examples of the surfactant which can be used include an anionic surfactant, a nonionic surfactant, a cationic surfactant, and an amphoteric surfactant.

With respect to 100 weight parts of the water absorbent resin used, an amount of the surfactant ranges from 0.0005 to 0.012 weight parts, preferably from 0.00005 to 0.001 weight parts, more preferably from 0.001 to 0.0045 weight parts, particularly preferably from 0.0015 to 0.004 weight parts. That is, when the amount is less than 0.0005 weight parts, improvement of the fluidity and the bulk density may be insufficient. On the other hand, when the amount exceeds 0.012 weight parts, a surface tension of absorbed liquid drops. Further, it is impossible to obtain an effect corresponding to an amount of the added surfactant. Such arrangement is not economical.

Further, an HLB (hydrophilic-hydrophobic balance) of the surfactant used in the present invention is not particularly limited. However, the HLB ranges preferably from 8 to 18, more preferably from 9 to 17, still more preferably from 10 to 17. In case where the HLB is in the foregoing range, it is possible to more favorably improve the fluidity and the bulk density.

Examples of the anionic surfactant include: fatty acids (soap) such as a mixed fatty acid sodium soap, a partially cured bovine fatty acid sodium soap, a stearic acid sodium soap, an oleic acid potassium soap, and a castor oil potassium soap; an alkylsulfate ester salt such as lauric sodium sulfate, higher alcohol sodium sulfate, lauric sodium sulfate, and lauric triethanolamine sulfate; alkylbenzene sulfosalt such as sodium dodecylbenzenesulfonic acid; alkylnaphthalene sulfosalt such as sodium alkylnaphthalene sulfosalt; alkylsulfo succinate salt such as sodium dialkylsulfo succinate salt; alkyldiphenylether disulfosalt such as sodium alkyldiphenylether disulfosalt; alkyl phosphate such as potassium alkyl phosphate; polyoxyethylene alkyl (or alkylallyl) sulfate ester salt such as polyoxyethylene laurylether sodium sulfate, polyoxyethylene alkylether sodium sulfate, polyoxyethylene alkylether triethanolamine sulfate, and polyoxyethylene alkylphenylether sodium sulfate; a special-reaction-type anionic surfactant; a special-carboxylic-acid-type surfactant; condensed naphthalene sulfonic acid formalin such as sodium salt of condensed β-naphthalene sulfonic acid formalin, and sodium salt of condensed special aromatic sulfonic acid formalin; a special polycarboxylic acid type macromolecule surfactant; polyoxyethylene alkyl phosphoric acid ester; and the like.

Examples of the nonionic surfactant include: polyoxyethylene alkyl ether such as polyoxyethylene lauryl ether, polyoxyethylene cetyl ether, polyoxyethylene stearyl ether, polyoxyethylene oleyl ether, and polyoxyethylene higher alcohol ether; and polyoxyethylene alkylaryl ether such as polyoxyethylene nonylphenyl ether; a polyoxyethylene derivative; a sorbitan fatty acid ester such as sorbitan monolaurate, sorbitan monopalmitate, sorbitan monostearate, sorbitan tristearate, sorbitan monooleate, sorbitan trioleate, sorbitan sesquioleate, and sorbitan distearate; polyoxyethylene sorbitan fatty acid ester such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate; polyoxyethylene sorbitol fatty acid ester such as tetraoleic acid polyoxyethylene sorbit; glycerine fatty acid ester such as glycerol monostearate, glycerol monooleate, and self-emulsification glycerol monostearate; polyoxyethylene fatty acid ester such as polyethyleneglycol monolaurate, polyethyleneglycol monostearate, polyethyleneglycol distearate, and polyethyleneglycol monooleate; polyoxyethylene alkylamine; polyoxyethylene curing castor oil; alkylalkanolamide; and the like.

Examples of the cationic surfactant and the amphoteric surfactant include: alkylamine salt such as coconut amine acetate, and stearylamine acetate; quaternary ammonium salt such as lauryl trimethyl ammonium chloride, stearyl trimethyl ammonium chloride, cetyl trimethyl ammonium chloride, distearyl dimethyl ammonium chloride, and alkyl benzyl dimethyl ammonium chloride; alkyl betaine such as lauryl betaine, stearyl betaine, and lauryl carboxymethyl hydroxyethyle imidazolium betaine; and amine oxide such as lauryl dimethylamin oxide. It is possible to add an antibacterial property to a hydrophilic polymer obtained by using the cationic surfactant.

Further, as the surfactant, it is possible to use a fluorinated surfactant. Also by using the fluorinated surfactant, it is possible to add the antibacterial property. As the fluorinated surfactant used in the present invention, various kinds of surfactant can be used. The fluorinated surfactant is obtained by, for example, replacing hydrogen of an oleophilic group of a general surfactant with fluorine so as to generate a perfluoroalkyl group. Its surface-active property is much stronger.

When a hydrophilic group of the fluorinated surfactant is changed, it is often that a hydrophobic group has a fluorocarbon chain having the same structure though there are four types of surfactant: an anionic type, a nonionic type, a cationic type, and an amphoteric type. Further, a carbon chain which is a hydrophobic group may be a straight chain or a branched chain. Typical examples of the fluorinated surfactant are as follows.

Fluoroalkyl (C2 to C10) carboxylic acid, N-perfluoro octane sulfonyl glutamic acid disodium, 3-[fluoroalkyl (C6 to C11) oxy]-1-alkyl (C3 to C4) sodium sulfonic, 3-[ω-fluoroalkanol (C6 to C8)-N-ethylamino]-1-sodium propane sulfonic acid, N-[3-(perfluorooctane sulfonamido) propyle]-N, N-dimethyl-N-carboxymethylene ammonium betaine, fluoroalkyl (C11 to C20) carboxylic acid, perfluoroalkyl carboxylic acid (C7 to C13), perfluorooctane sulfonic acid diethanolamide, perfluoroalkyl (C4 to C12) sulfosalt (Li, K, Na), N-propyl-N-(2-hydroxyethyl) perfluorooctane sulfone amide, perfluoroalkyl (C6 to C10) sulfone amide propyltrimethyl ammonium salt, perfluoroalkyl (C6 to C10)-N-ethylsulfonyl glycine salt (K), phosphoric acid bis(N-perfluorooctylsulfonyl-N-ethylaminoethyl), monoperfluoroalkyl (C6 to C16) ethyl phosphoric acid ester, perfluoroalkyl quaternary ammonium iodide (commercial name: Fluorad FC-134, cationic fluorinated surfactant produced by Sumitomo 3M Ltd.), perfluoroalkylalcoxylate (commercial name: Fluorad FC-171, nonionic fluorinated surfactant produced by Sumitomo 3M Ltd.), and perfluoroalkyl sulfonic acid potassium salt (commercial name: Fluorad FC-95 and FC-98, anionic fluorinated surfactant produced by Sumitomo 3M Ltd.).

In this invention, it is possible to use also an organic metal surfactant. The organic metal surfactant used in the present invention has a molecule whose main chain or lateral chain has a metal such as Si, Ti, Sn, Zr, Ge, and the like. It is preferable to use a surfactant which has a molecule whose main chain has Si, and it is more preferable to use a siloxane surfactant.

A typical example of the organic metal surfactant is mentioned in "New Edition: Surfactant Handbook" written by Yoshida, Kondo, Ogaki, Yamanaka, published by Kogakutosho Ltd. (1966), page 34. As a metal contained in the organic metal surfactant, it is possible to use Sn, Zr, Ge, and the like instead of Si or Ti. The surfactant used in the present invention is not limited to the foregoing surfactants.

Among these surfactants, the nonionic surfactants are preferable in terms of safety. Among of them, sorbitan fatty acid ester, polyoxyethylene sorbitan fatty acid ester are particularly preferable.

Embodiment 3

<Powder Lubricant>

The lubricant is a substance, intervening between two faces sliding each other, which reduces a friction (resistance) therebetween. That is, when substances are in contact with each other, surface conditions of the substances cause the faces to more likely to or less likely to slide each other, or the resistance therebetween to be higher or smaller, and the lubricant reduces the resistance.

The lubricant used in the present invention reduces a friction (resistance) between water absorbent resins. By using the lubricant, it is possible to obtain the particulate water absorbing agent whose loose bulk density and flow rate have been increased. By increasing the flow rate, it is possible to reduce (i) a time taken to move the particulate water absorbing agent from the container to the hopper and (ii) a time taken to fill the container with the particulate water absorbing agent having been moved from the hopper, thereby improving an efficiency in the operation. These effects are obtained also in the aforementioned surfactants, and are great effects of a novel water absorbent of the present invention.

Further, the loose bulk density and the flow rate increase, so that it will be possible to decrease (i) a powder stirring force in producing the particulate water absorbing agent and (ii) energy required in pneumatic transportation. Further, the powder stirring force and the energy required in the pneumatic transportation are reduced, which prevents particles of the water absorbent resin from being broken down, so that it will be possible to suppress increase of fine particles which is caused by drop in the properties such as an absorbency against pressure.

The lubricant which can be used in the present invention is not particularly limited as long as the lubricant is a solid product. Examples thereof include a hydrocarbon lubricant, a fatty acid lubricant, a fatty acid amide lubricant, an ester lubricant, an alcohol lubricant, a metal soap lubricant, and the like. Among them, the metal soap lubricant is favorably used since the metal soap lubricant has functions not only as a lubricant but also as a stabilizer. Further, it is necessary that the lubricant of the present invention is in a solid phase at a normal temperature (25° C.) and a normal pressure (0.101 MPa).

As the hydrocarbon lubricant, it is possible to use low polymerization polyethylene. The low polymerization polyethylene is polyethylene whose molecular mass approximately ranges from 1500 to 2000.

The fatty acid lubricant is not particularly limited as long as this is fatty acid which functions as a lubricant. However, it is preferable to use fatty acid which contains 12 ($C_{12}$) carbons in its molecule. Specific examples thereof include lauric acid, myristic acid, palmitic acid, stearic acid, arachidonic acid, behenic acid, and the like. Among them, it is preferable to use stearic acid because of its easiness to obtain. Further, as the fatty acid lubricant, it is preferable to use fine particles, and it is preferable to use a purified product, containing no polymerized metal such as Fe, Ni, promoting deterioration of the water absorbent resin, whose iodine value and ester value are low.

The fatty acid amide lubricant is a compound, derived from fatty acid, which is represented by $RCONH_2$. Examples of the fatty acid amide include first amide ($R-CONH_2$), second amide ($(RCO)_2NH$), and third amide ($(RCO)_3N$). It is preferable to use the first amide. Specific examples thereof include stearylamide, palmitylamide, oleylamide, methylenebis stearoamide, ethylenebis stearoamide, and the like. Among them, methylenebis stearoamide and ethylenebis stearoamide are preferable since they are superior in compatibility, transparency, weather resistance, and nonadhesiveness.

As the ester lubricant, it is possible to use fatty acid multivalent alcohol ester, fatty acid polyglycol ester, and the like. As the fatty acid multivalent alcohol ester, it is preferable to use curing castor oil. Further, as the fatty acid polyglycol ester, it is preferable to use ethyleneglycol monostearate.

The alcohol lubricant is obtained by replacing hydrogen of the hydrocarbon lubricant or the fatty acid lubricant with a hydrogen group. The alcohol lubricant is not particularly limited as long as hydrogen of the hydrocarbon lubricant or the fatty acid lubricant is replaced with a hydrogen group. However, examples thereof include: fatty alcohol such as cetyl alcohol and stearyl alcohol having a hydrogen group in its molecule; glycol such as polyethyleneglycol having two hydrogen groups in its molecule; polyglycerol having three hydrogen groups in its molecule; and the like. Polyethyleneglycol or polyglycerol functions as a lubricant and prevents electrostatic charge.

The metal soap lubricant is made of fatty acid (organic acid), petroleum acid, and metal salt other than alkaline metal salt such as macromolecule acid.

Generally, the powder lubricant is powder, and its particle diameter is not particularly limited. However, it is general that the particle diameter is smaller than a weight (mass) average particle diameter of the water absorbent resin. The particle diameter of 90 wt % or more of powder is 100 μm or less, preferably 50 μm or less, more preferably 10 μm or less.

Note that, the foregoing lubricants may be used independently or in a suitable combination of two or more kinds. How the lubricant is added to the water absorbent resin is the same as in Embodiment 1, so that description thereof is omitted. The following will explain an amount of the lubricant added to the water absorbent resin.

In case of mixing the powder lubricant with the water absorbent by dispersing the powder lubricant in a slurry manner, the concentration of the lubricant in the slurry is appropriately determined in accordance with (i) kinds of the lubricant used and dispersion solvent and (ii) viscosity of the slurry, and this is not particularly limited. However, the concentration of the lubricant ranges generally from 0.001 to 0.1 wt %, preferably from 0.001 to 0.05 wt %. A powder temperature of the water absorbent resin in being mixed with the lubricant is generally not less than a room temperature. However, in order to stably obtain a water absorbent property, a flow rate, and a bulk density of the particulate water absorbing agent, the powder temperature is preferably 40° C. or higher, more preferably 50° C. or higher.

That is, in the particulate water absorbing agent of the present invention, the amount of the lubricant added is appropriately changed in accordance with a target bulk density and a target flow rate. However, the amount of the lubricant added preferably ranges from 0.0001 to 0.1 wt %, more preferably from 0.01 to 0.05 wt %, particularly preferably from 0.001 to 0.01 wt %. In case where the amount of the lubricant added is in the foregoing range, the amount is so small, so that a hydrophobic property and a water repellent property are not added. This allows the bulk density to be increased without dropping the water absorbent property. Further, it will be possible to prevent the water absorbent property from being dropped by a mechanical shock, and to reduce a powder stirring force in producing the particulate water absorbing agent, and to reduce energy required in pneumatic transportation of the particulate water absorbing agent. While, in case where the amount of the lubricant added exceeds the foregoing range, this is not economical and may result in drop of the water absorbent property.

(III) Particulate Water Absorbing Agent

<Production Method of Particulate Water Absorbing Agent>

The particulate water absorbing agent according to the present invention should only have to have the unique parameters, and preferably contains the aforementioned powder lubricant or surfactant and the aforementioned water absorbent resin, and is produced by a method which is not limited in any particular manner. The water absorbent may be produced, for example, by one of methods 1 to 6 below.

(Method 1)

A powder lubricant is dispersed in a monomer aqueous solution containing an internal cross-linking agent at the time of polymerization of the water absorbent resin. The product is dried, pulverized, and is subjected to a surface cross-linking treatment where necessary to prepare the particulate water absorbing agent resin.

(Method 2)

The powder lubricant or the surfactant is added and mixed with the water absorbent resin. A vicinity of a surface of the water absorbent resin is cross-linked to obtain the particulate water absorbing agent.

(Method 3)

A vicinity of a surface of the water absorbent resin is cross-linked with a surface cross-linking agent containing the powder lubricant or the surfactant to obtain the particulate water absorbing agent.

(Method 4)

A vicinity of a surface of the water absorbent resin is cross-linked where necessary to prepare a water absorbent resin whose surface is further cross-linked. Thereafter, the powder lubricant or the surfactant are mixed to obtain the particulate water absorbing agent.

(Method 5)

A monomer whose lateral chain has a hydrocarbon group containing seven or more carbons in its molecule and a polymerization initiator (and a surface cross-linking agent where necessary) are mixed with a vicinity of a surface of the water absorbent resin, and a polymerization reaction (and a cross-linking reaction where necessary) is carried out in the surface of the water absorbent resin, and the macromolecule additive is formed directly in the surface of the water absorbent resin to prepare the particulate water absorbing agent.

(Method 6)

The powder lubricant is added to the water absorbent resin, and the powder lubricant is heated while being stirred so as to fuse the powder lubricant. Thereafter, the fused powder lubricant is cooled to obtain the particulate water absorbing agent.

In the methods 1 to 6, a monomer aqueous solution may be added at the time of polymerization of the water absorbent resin as in the method 1, but it is preferable to add the additive to the water absorbent resin on the basis of the methods 2 to 4 and 6 in order to realize a condition under which the additive evenly adheres to the surface of the water absorbent resin.

<Other Components of Particulate Water Absorbing Agent>

To acquire various capabilities, the particulate water absorbing agent according to the present invention may contain substances other than those mentioned so far (water absorbent resin, macromolecule additive, internal cross-linking agent, polymerization initiator, surface cross-linking agent, etc.). These additional substances may be multivalent metal, inorganic powder, hydrophilic organic solvent such as water, to granulate the water absorbent resin. The addition of them may improve the liquid permeability and the fluidity of the particulate water absorbing agent.

Note that, the multivalent metal and the inorganic powder used are mentioned in International Applications WO2004/JP1007 (international filing date: Feb. 2, 2004), WO2004/JP1294 (international filing date: Feb. 6, 2004), WO2004/JP9242 (international filing date: Jun. 3, 2004), and the like.

Specifically, the inorganic powder are substances inert with respect to aqueous liquid, for example, various inorganic compound fine particles, clay mineral fine particles, and the like. It is preferable that: the inorganic powder has an appropriate hydrophilic property with respect to water, and it is insoluble or hardly soluble in water. Specific examples of the inorganic powder include metal oxides, such as silicon dioxide and titanium oxides; silicic acids (salts), such as natural zeolite and synthetic zeolite; kaolin; talc; clays; and bentonite. Preferred among them are silicon dioxide and silicic acids (salts), particularly silicon dioxide and silicic acids (salts) having an average particle diameter of 200 mm or less as measured using a Coulter counter. Further, examples of the multivalent metal used include aluminum salts such as aluminum sulfate, alum, and the like. The multivalent metal is added at quantities which differ depending on the combination of the water absorbent resin and/or the particulate water absorbing agent and inorganic powder. The multivalent metal content is from 0.001 to 10 parts by weight, preferably from 0 to 6 parts by weight, more preferably from 0.001 to 5 parts by weight, and still more preferably from 0.01 to 3 parts by weight, most preferably from 0.1 to 1 part by weight, in every 100 parts by weight of the water absorbent resin and/or the particulate water absorbing agent. Although depending on the desired water absorbent property and the desired particle size of the particulate water absorbing agent, the multivalent metal content beyond these ranges may be in excess of the shock absorptive capability provided by the macromolecule additive; it could be difficult to prevent degradation of shock force absorbing properties.

The inorganic powder may be mixed with the water absorbent resin and/or the particulate water absorbing agent by any method. An example is dry blending or wet blending whereby two kinds of powder are mixed together (the additive is dispersed or dissolved in the solvent). In case of using the inorganic powder, the dry blending is more desirable. Further, in case of using the multivalent metal, it is preferable to adopt wet mixing treatment.

Further, the method according to the present invention for producing the particulate water absorbing agent may further include a step of giving various functions, e.g., a step of adding a deodorant, antibacterial agent, perfume, foaming agent, pigment, dye, plasticizer, adhesive, surfactant, fertilizer, oxidizing agent, reducing agent, water, salt, chelating agent, bactericide, hydrophilic macro molecules, such as polyethylene glycol, and polyethyleneimine, hydrophobic macromolecule, such as paraffin, thermoplastic resins, such as polyethylene and polypropylene, and heat curing resins, such as a polyester resin and urea resin. The additives are added at quantities from 0 to 30 parts by weight, preferably from 0 to 10 parts by weight, more preferably 0 to 1 part by weight, to every 100 parts by weight of the water absorbent resin.

In the particulate water absorbing agent of the present invention, when small amounts of the surfactant and the powder lubricant are added, it is possible to prevent the absorbent property of the particulate water absorbing agent from dropping without dropping the surface tension of the absorbed liquid. The inventors of the present invention found that: there is an optimal value (peak) in variation of the powder fluidity with respect to an amount of the surfactant and the powder lubricant added, and an amount exceeding the peak results in a lower flow rate, and a bridge is formed when discharged from a lower portion of a hopper (container), so that the flow is prevented. Therefore, there is an important meaning in small amounts of the surfactant and the powder lubricant in terms not only of the drop in the surface tension but also of the powder property.

The following description will explain properties of the particulate water absorbing agent of the present embodiment.

<Particle Diameters of Particulate Water Absorbing Agent>

The particulate water absorbing agent according to the present invention is, where necessary, granulated using water-insoluble fine particles or a hydrophilic solvent and the like. Preferably, particles from less than 850 mm to not less than 150 mm account for not less than 90 wt % (upper limit is 100%) of the particulate water absorbing agent. More preferably, those particles account for not less than 95 wt % of the particulate water absorbing agent. Even more preferably, those particles account for not less than 98 wt % of the particulate water absorbing agent. A granulation, if at all, is preferably carried out so that the particulate water absorbing agent has these specific particle diameters.

Further, a mass average particle diameter of the particulate water absorbing agent preferably ranges from 200 to 600 µm, more preferably ranges from 250 to 600 µm, still more preferably ranges from 250 to 550 µm, particularly preferably ranges from 250 to 500 µm, most preferably ranges from 300 to 500 µm.

A logarithmic standard deviation ($\sigma\zeta$) indicative of a particle size distribution preferably ranges from 0.25 to 0.45, more preferably ranges from 0.25 to 0.42, still more preferably ranges from 0.25 to 0.40, most preferably ranges from 0.25 to 0.38.

In case where the amount of the particles whose particle diameter is less than 150 µm (fine particles) exceeds 10 wt %, this raises the following problems: diffusion of blood or urine in an absorbent core is inhibited at the time of moisture absorption; an area in contact with air increases when used as an absorbent core, so that the particulate water absorbing agent is more likely to be soluble; the fluidity at the time of moisture absorption is deteriorated; occurrence of dusts during operation in manufacturing sanitary materials such as a particulate water absorbing agent and a diaper deteriorates an operation environment; a wide particle size distribution results in segregation; and a similar problem. This is not preferable. Further, when the logarithmic standard deviation is less than 0.25, a bulk density may drop. Particularly, in the particulate water absorbing agent of the present invention which improves the powder fluidity, the segregation is conspicuous in a hopper or a bag, so that quality unevenness is likely to occur when provided in a diaper or the like. In case where the amount of the particles whose particle diameter is more than 850 µm is 10 wt % or more, a water absorbent ratio of the particulate water absorbing agent becomes low, and the absorbent core feels rough when used in an absorbent article. This results in uncomfortable feeling for the user, so that such arrangement is not preferable. By adjusting the particle size within a preferable range of the present invention, it is easy to obtain the particulate water absorbing agent, superior in the fluidity and the bulk density, whose absorbent property does not drop and which is free from any problem such as segregation or the like.

The particle diameter of the particulate water absorbing agent may be adjusted, according to its object and necessity, by adding/mixing insoluble fine particles, a hydrophilic solvent, preferably water thereto, and by further granulating the resultant.

The particle size may be adjusted by carrying out dispersion polymerization and dispersion drying treatment with respect to the resultant in the particle state like the reverse suspension polymerization. Generally, in case of aqueous solution polymerization particularly, the resultant is pulverized and classified after being dried, and is recycled by carrying out granulation or the like with respect to thus classified resultant where necessary, thereby adjusting the particle size to a specific particle size.

Further, in order to obtain the particulate water absorbing agent of the present invention, a loose bulk density (defined by JIS K-3362) of the water absorbent resin of the present invention is adjusted so as to preferably range from 0.45 to 0.85 g/ml, more preferably from 0.50 to 0.80 g/ml, still more preferably from 0.55 to 0.80 g/ml.

<Absorbency Against Pressure>

An absorbency against pressure (AAP1) of the particulate water absorbing agent of the present invention at a pressure (load) of 2.03 kPa is 20 g/g or more, preferably 22 g/g or more, more preferably 24 g/g or more, still more preferably 26 g/g or more, most preferably 28 g/g or more. Further, an upper limit of the absorbency against pressure is not particularly limited. As the absorbency against pressure is higher, it is more preferable. However, from an economic view point such as manufacturing cost or the like, the absorbency against pressure is generally 50 g/g or less, more preferably 45 g/g or less.

An absorbency against pressure (AAP2) of the particulate water absorbing agent of the present invention at a pressure (load) of 4.83 kPa is 17 g/g or more, preferably 18 g/g or more, more preferably 19 g/g or more, most preferably 20 g/g or more. Further, an upper limit of the absorbency against pressure is not particularly limited. However, from an economic view point such as manufacturing cost or the like, the absorbency against pressure is generally 50 g/g or less, more preferably 45 g/g or less.

Note that, the absorbency against pressure is evaluated here under the load of 2.03 kPa and 4.83 kPa, based on an assumption that the absorbent core or the absorbent article such as a diaper is used in receiving a load from an infant in a lying or sitting position. Note that, how the absorbency against pressure is measured will be explained in Examples.

<Fluidity Index at Time of Moisture Absorption>

The fluidity index at the time of moisture absorption (hereinafter, referred to merely as moisture absorption fluidity) is indicative of evaluation of a blocking property, a caking property, or a powder fluidity under such condition that the particulate water absorbing agent is left at 25° C. with a relative humidity of 90% RH. When a moisture absorption ratio ranges from about 1 to 25 wt %, the particulate water absorbing agent is free from any blocking or any caking, and exhibits a superior moisture absorption fluidity. In the particulate water absorbing agent, its moisture-absorption fluidity index in case where it is left at 25° C. with a relative humidity of 90% RH ranges from not less than 90 wt % to not more than 100 wt %, preferably from not less than 95 wt % to not more than 100 wt %, and more preferably not less than 98 wt % to not more than 100 wt %. It is possible to prevent (i) drop in the fluidity at the time of moisture absorption, (ii) unification of the particulate water absorbing agent particles, and (iii) blocking of the particulate water absorbing agent particles, when reserving the water absorbent resin or the particulate water absorbing agent or when manufacturing an absorbent article such as a diaper. Thus, it is possible to prevent a production device from being stopped by powder blocking which occurs in the production device. Note that, how the moisture-absorption fluidity index is measured will be detailed in Examples.

<Shape of Particulate Water Absorbing Agent>

General examples of the shape of the water absorbent include the primary particles shape, from spherical and ellipsoidal to partially flattened ellipsoidal, obtained by reverse phase suspension polymerization illustrated in U.S. Pat. No. 5,244,735, FIGS. 1, 2; the shape of a granulated product of the primary particles produced by agglomeration of spherical and/or ellipsoidal particles, like agglomerated beads illustrated in NON WOVENS WORLD, October-November 2000 Issue (published by Marketing Technology Service, Inc.), page 75, FIG. 1; and the indefinite shapes of a crushed product of a water-containing gel-like polymer obtained by polymerization of an aqueous monomer solution and the shapes of the granulated product of the crushed product, like crystals in U.S. Pat. No. 5,981,070, FIGS. 2, 3, 4 and NON WOVENS WORLD, October-November 2000 Issue, page 75, FIG. 1.

The particulate water absorbing agent according to the present invention is preferably of a shape other than the shape of spherical primary particles and the shape of ellipsoidal primary particles, more preferably of a shape of the granulated product of spherical or ellipsoidal particles, of an indefinite shape of a crushed product of a water-containing gel-like polymer obtained by polymerization of an aqueous monomer solution, or of a shape of the granulation product of the crushed product, and even more preferably of an indefinite shape or a shape of the granulation product.

The non-preference for spherical primary particles and/or ellipsoidal primary particles is because the shapes do not mix well with pulp and other fiber materials in, for example, the production of absorbent articles, and the particulate water absorbing agent is easy to fall from an absorbent core based on a mixture of the particulate water absorbing agent and a fiber material. Therefore, the use of the water absorbent in the form of spherical primary particles and/or ellipsoidal primary particles raises a problem that it becomes difficult to uniformly distribute the water absorbent in an absorbent core.

<Powder Fluidity in Dray State>

The macromolecule additive used in the particulate water absorbing agent obtained in the present invention has a high fusing point, a high glass transition point, or a high softening point, which is higher than a room temperature. Thus, at the room temperature, not only at the time of moisture absorption but also in such dry state that its moisture content is 0 to 20 wt %, more preferably 0 to 10 wt %, it is possible to achieve high powder flowability and high powder fluidity in a compacted state. As an index indicative of the powder flowability, a flow rate (450.2-02) defined by EADNA (European Disposables and Nonwovens Association) is used. The flowability is obtained by measuring a time taken for 100 g of the water absorbent resin or particulate water absorbing agent powder placed in a specified hopper to be entirely discharged under a room temperature condition (at 25° C. with a relative humidity of 50% RH). It is considered that: as the flowability is low, higher fluidity is obtained. A preferable range of the flowability is within 20 seconds, and a more preferable range is within 17 seconds, and a most preferable range is within 14 seconds.

Further, conventionally, in order to secure the fluidity under a moisture absorption condition, it is general to add an organic substance to the particulate water absorbing agent. When the organic substance is added to the particulate water absorbing agent, a frictional coefficient between the particles particularly in such a dry state that its moisture content ranges from 0 to 20 wt % becomes high (lubricity between the particles deteriorates). Thus, this increases a transport resistance in transporting the particulate water absorbing agent by means of an air transporter, a paddle-type transporter, or a screw-type transporter. As a result, blocking of the particulate water absorbing agent occurs in the production device or the transporter, and its property drops, and excessive load is exerted. Such conditions cause the device to be frequently stopped.

Particularly, an indefinite-shape particle (an indefinite-shape crushed product derived from a crushed water-containing gelatinous polymer and a granulation product thereof, a granulation product made of agglomerated globular or ellipsoidal particles obtained by reverse suspension polymerization) has a distorted shape, so that the frictional coefficient between particles increases which deteriorates the fluidity in a compacted state.

However, the particulate water absorbing agent of the present invention includes the water absorbent resin and the powder lubricant or the surfactant that were described above, so that its fluidity in a compacted state is extremely high even when the particulate water absorbing agent includes the indefinite-shape particles.

The inventors of the present invention found that: when the fluidity of the particulate water absorbing agent in a compacted state is evaluated and the evaluation shows that the particulate water absorbing agent has a predetermined fluidity, even the particulate water absorbing agent including indefinite-shape particles is easy to treat in the production device or the transporter, thereby preventing troubles such as blocking and the like.

That is, the fluidity in a compacted state is evaluated in this manner: A probe (metal rod), an insertion member, is vertically inserted to 20 mm deep in a particulate water absorbing agent in a compacted state. The powder fluidity is evaluated by an insertion work (probe insertion work by 20 mm insertion, or "PIW") with the probe inserted to 20 mm deep. According to this method, less PIW values with the probe inserted to 20 mm deep indicate that the particulate water absorbing agent in powder form has a lower internal friction coefficient and frictional force and higher fluidity.

Many conventionally known water absorbent resins and particulate water absorbing agents have low fluidity in a compacted state and do not even allow the 20-mm deep probe insertion distance (probe insertion distance, or "PID," in accordance with the present invention).

In contrast, the particulate water absorbing agent according to the present invention has a low PIL when the probe is inserted 20 mm. Specifically, the PIL is from not less than 0 g-weight×mm to not more than 75,000 g-weight×mm, preferably from not less than 0 g-weight×mm to not more than 55,000 g-weight×mm, more preferably from not less than 0 g-weight×mm to not more than 45,000 g-weight×mm, even more preferably from not less than 0 g-weight×mm to not more than 35,000 g-weight×mm, and still more preferably from not less than 0 g-weight×mm to not more than 25,000 g-weight×mm. If the PIW exceeds these ranges, the particulate water absorbing agent has a great internal friction coefficient, so that there is a possibility that troubles such as drop in the property and blocking in the production device or the transporter may occur.

In this manner, by using the foregoing evaluation method, a particulate water absorbing agent with a predetermined powder fluidity is selected, so that it is possible to surely provide the particulate water absorbing agent which has high fluidity. Further, the particulate water absorbing agent of the present invention has high fluidity (flowability, fluidity in a compacted state). This allows, for example, reduced transportation resistance in air flow transportation of the particulate water absorbing agent, in transportation using a paddle-type transporter, and in transportation using a screw-type transporter. Conventionally frequent clogging of production device and transportation devices, and halting of the devices due to overloading are all prevented. Further, the particulate water absorbing agent is useful in the facilitation of hoppers, powder storages, and like device which are used in, for example, a production process of an absorbent core based on the particulate water absorbing agent.

<Centrifuge Retention Capacity (CRC)>

The centrifuge retention capacity (CRC) represents an absorbency (CRC1) at which 0.90 wt % of sodium chloride aqueous solution is absorbed for 30 minutes without any pressure. This CRC1 is preferably 25 g/g or more, more preferably 28 g/g or more, still more preferably 30 g/g or more. In case where the absorbency is out of the ranges, there is a possibility that the particulate water absorbing agent does not exhibit a high property when used in a diaper.

Further, in the present invention, the surface cross-linking allows the absorbency (CRC1) to drop, preferably to drop by 95 to 50%, further by 90 to 60%, with respect to the product which has not been subjected to the surface cross-linking treatment. Note that, the drop in the absorbency is adjusted as required in accordance with a type, an amount, a reaction temperature, and a reaction time of the cross-linking agent.

<Carryover Factor of Five-Minute Absorbency>

As will be described in Examples, a carryover factor of the five-minute absorbency is a parameter indicative of a ratio (percentage) of a five-minute centrifuge retention capacity (CRC2) with respect to a 30-minute centrifuge retention capacity (CRC1), and is a parameter indicative of how the absorption rate is influenced in case where the water absorbent is reformed by the additive. Thus, this shows that: as the five-minute absorbency is higher, the absorption rate is higher and the absorbent property is superior. The particulate water absorbing agent obtained in the present invention is characterized by hardly dropping its absorption rate, and its carryover factor of the five-minute absorbency is 30% or more and 100% or less, preferably 40% or more and 100% or less, more preferably 50% or more and 100% or less, most preferably 55% or more and 100% or less. When the carryover factor of the five-minute absorbency is less than 30%, the absorption rate is too low, so that a trouble such as leakage of urine is more likely to occur in case where the particulate water absorbing agent is used in a sanitary material such as a diaper.

<Surface Tension>

As will be described in Examples, the surface tension is used to estimate how much a surface tension of absorbed liquid is to be dropped in case where the water absorbent resin or the particulate water absorbing agent is in contact with the absorbed liquid. In case where the surface tension greatly drops, when the particulate water absorbing agent is used in a sanitary material such as a diaper, a re-wet amount (an amount of returning urine which has been absorbed by a diaper) is large, which results in such disadvantage that the wearer feels uncomfortable. The particulate water absorbing agent obtained in the present invention is characterized by less dropping its surface tension. In case where the surface tension is measured by a measurement method described in Examples, under a measurement condition of 20° C., the surface tension is preferably 50 mN/m or more, more preferably 55 mN/m or more, still more preferably 60 mN/m or more, particularly preferably 65 mN/m or more, most preferably 68 mN/m or more.

<Loose Bulk Density (Bulk Specific Gravity)>

As will be described in Examples, the "loose bulk density" (unit: g/ml) is a value indicating a mass of the whole agglomerated particles as a mass for each unit capacity in case where a container having a certain capacity is filled with the agglomerated particles. That is, as the loose bulk density is higher, a mass of particles occupying each unit capacity is larger. Further, in case where the container is filled with the particles, there is a gap (space) between the particles, so that the loose bulk density becomes lower than a "vacuum density" (unit: $g/cm^3$) indicative of a mass for a particle volume with a difference corresponding to the space. For example, as to sodium polyacrylic acid, the vacuum density of the water absorbent resin is about 1.5 to 1.7 $g/cm^2$.

In the particulate water absorbing agent of the present invention, the loose bulk density preferably ranges from 0.45 to 0.85 g/ml, more preferably from 0.50 to 0.80 g/ml, still more preferably from 0.55 to 0.80 g/ml, particularly preferably from 0.70 to 0.80 g/ml.

By increasing the loose bulk density, it is possible to stabilize and increase an amount of the particulate water absorbing agent filled in the container for example. Therefore, it is possible to reduce cost of the container and it is possible to store a certain and large amount of the particulate water absorbing agent and it is possible to transport the particulate water absorbing agent with a storage tank such as a hopper. An absorbent core in which a particulate water absorbing agent and a fiber are used so that the particulate water absorbing agent is more used allows a thickness thereof to be thinned.

<Tapped Bulk Density>

A "tapped bulk density" (unit: g/ml) is a value indicating a mass of whole agglomerated particles for each unit capacity by measuring a container in which a certain mass of the agglomerated particles are filled and are hardened with the container tapped. By tapping, the particles are more densely filled, so that it is general that the tapped bulk density is higher than the loose bulk density. Further, as will be described in "Compressibility rate", a difference between the tapped bulk density and the loose bulk density greatly influences the fluidity of particles.

In the particulate water absorbing agent of the present invention, the tapped bulk density preferably ranges from 0.65 to 0.85 g/ml, more preferably from 0.68 to 0.80 g/ml, still more preferably from 0.70 to 0.80 g/ml.

<Compressibility Rate>

The "compressibility rate" (unit: %) is a value calculated from the loose bulk density and the tapped bulk density in accordance with the following equation.

Compressibility rate=$(P-A)/P \times 100$ where P represents the tapped bulk density and A represents the loose bulk density.

The particles whose compressibility rate is high are likely to form a bridge in a hopper outlet of the device. In this manner, the fluidity of such particles drops. Further, the bulk density is likely to vary due to the filling operation, so that it is difficult to stably provide the particulate water absorbing agent. This causes the property to deteriorate in manufacturing and practically using the absorbent.

The compressibility rate of the particulate water absorbing agent of the present invention preferably ranges from 0 to 18%, more preferably from 0 to 15%, still more preferably from 0 to 10%.

<Flow Rate>

The "flow rate" is a value indicative of powder fluidity. In the particulate water absorbing agent of the present invention, a friction resistance between particles is reduced. Thus, it is possible to increase the flow speed without dropping the water absorbent property. Particularly, although an amount of the surfactant used is extremely small, it is possible to obtain a great effect.

In the particulate water absorbing agent of the present invention, the flow rate is preferably ranges from 5 to 15 g/s, more preferably from 7 to 15 g/s, still more preferably from 10 to 15 g/s. When the flow rate is 5 g/s or more, it is easier to treat the powder. When the flow rate is less than 5 g/s, the powder hardly flows, so that it is hard to treat the particulate water absorbing agent. Thus, such arrangement is not preferable.

<Stirring Resistance>

A stirring resistance of the particulate water absorbing agent is evaluated by rotating a rotor of a rotating viscometer positioned in a container filled with the particulate water absorbing agent. In the particulate water absorbing agent of the present invention, a frictional resistance between the particles and the device is reduced, so that it is possible to reduce a load exerted to the device and damages of the particulate water absorbing agent resin at the time of surface cross-linking treatment, and it is possible to reduce a load exerted to the device and damages of the particulate water absorbing agent resin at the time of pneumatic transportation, thereby stabilizing a quality of the particulate water absorbing agent. Particularly, although an amount of the surfactant used is extremely small, it is possible to obtain a great effect.

In case where a measurement method described in Examples is adopted, the stirring resistance of the particulate water absorbing agent of the present invention is preferably 0.37 N·cm or less (lower limit is 0 N·cm), more preferably 0.30 N·cm or less, still more preferably 0.25 N·cm or less.

<Saline Flow Conductivity (SFC)>

A saline flow conductivity is a value indicative of liquid permeability of the particulate water absorbing agent in a swelling state. As the value is higher, the liquid permeability is higher.

In case where a measurement method described in Examples is adopted, the saline flow conductivity (SFC) of the particulate water absorbing agent resin of the present invention is preferably $20(10^{-7} \cdot cm^3 \cdot s \cdot g^{-1})$ or more, more preferably $30(10^{-7} \cdot cm^3 \cdot s \cdot g^{-1})$ or more, still more preferably $50(10^{-7} \cdot cm^3 \cdot s \cdot g^{-1})$ or more, particularly preferably $80(10^{-7} \cdot cm^3 \cdot s \cdot g^{-1})$ or more.

(IV) Absorbent Core and/or Absorbent Article

The particulate water absorbing agent according to the present invention is used for water absorbing purposes. It is widely used in the form of absorbent cores and absorbent articles, and preferably as sanitary materials to absorb urine, blood, and other body fluids. The absorbent core and absorbent article according to the present invention contains the particulate water absorbing agent according to the present invention.

The absorbent core here refers to an absorptive material prepared by molding the water absorbent resin and a hydrophilic fiber as main components. The absorbent core is formed, for example, into a film shape, a cylindrical shape, and a sheet shape, by using the particulate water absorbing agent resin and the hydrophilic fiber. The absorbent core contains the particulate water absorbing agent at an amount (core concentration) of preferably from 20 to 100 wt %, more preferably from 30 to 100 wt %, still more preferably 40 to 100 wt %, to the combined mass of the water absorbent and the hydrophilic fiber. The greater core concentration the particulate water absorbing agent according to the present invention has, the more distinct the effect of decreasing absorption characteristics of the particulate water absorbing agent when absorbent cores or absorbent articles are produced. Further, it is preferable that the absorbent core is thin (its thickness is 0.1 to 5 mm).

Further, the absorbent core contains: a particulate water absorbing agent including (i) a water absorbent resin having a cross-linking structure in its molecule which is obtained by polymerizing an unsaturated monomer and (ii) a solid lubricant; and a hydrophilic fiber.

Particularly, when the particulate water absorbing agent in which the macromolecule additive of the present invention has been added is used, it is possible to obtain the absorbent core, having a higher strength, in which the hydrophilic fiber and the particulate water absorbing agent are fixed and the particulate water absorbing agent hardly falls, by heating a molded mixture of the hydrophilic fiber and the particulate water absorbing agent up to a fusing point, a glass transition point, or a softening point of the macromolecule additive added to the particulate water absorbing agent.

In addition, the absorbent article is made up of the absorbent core, a front sheet permeable to liquid, and a back sheet impermeable to liquid. The absorbent article, including disposable diapers for adults and sanitary napkins, are produced in the following manner: First, the particulate water absorbing agent is blended or sandwiched with a fiber base material, for example, a hydrophilic fiber, to form an absorbent core (absorption core). The absorption core is then sandwiched between a liquid-permeable front sheet and a liquid-impermeable back sheet. Thereafter, an elasticity member, a diffusion layer, and/or adhesive tape is fitted if necessary. Under these conditions, the absorption core is compression molded to a density of 0.06 to 0.50 g/cc and a basic weight of 0.01 to 0.20 g/cm². The fiber base material used is, for example, crushed wood pulp or a like hydrophilic fiber, a cotton linter, a cross-linked cellulose fiber, rayon, cotton, wool, acetate, or vinylon. These fiber base materials are preferably aerated.

The absorbent article of the present invention exhibits a superior absorbent property. Specific examples of such absorbent article include sanitary material such as: an adult diaper which has been being remarkably developed recently; a child diaper; a sanitary napkin; an incontinence pad; and the like, but the present invention is not limited to them. When the absorbent article of the present invention is used, it is possible to reduce an amount of an absorbed aqueous liquid which returns from the particulate water absorbing agent contained in the absorbent article, so that an excellent dry condition is kept after absorbing water. As a result, it is possible to reduce loads of a user wearing the absorbent article and caregivers.

The particulate water absorbing agent of the present invention has excellent fluidity at the time of moisture absorption and excellent absorbent properties, so that the particulate water absorbing agent can be used as various kinds of absorbent articles. Specifically, it is possible to favorably use the particulate water absorbing agent as: a sanitary material (body fluid absorbent article), such as an adult disposable diaper, a child diaper, a sanitary napkin, and a so-called incontinence pad, a wound protective material, and a wound curing material, that has been greatly developed recently; an absorbent article for pet urine; an engineering material such as a building material, an engineering water retention material, a water stop material, a packing material, and a gelatinous pusule; a kitchen good such as a drip absorbent, a freshness-keeping material, and a cold insulator; various industrial products such as an oily water separating material, a dewfall inhibitor, and a coagulator; and an agriculture/horticulture product such as a water retention material for plants, soils, and the like. When the absorbent article including the particulate water absorbing agent of the present invention is used, it is possible to reduce an amount of an absorbed aqueous liquid which returns from the particulate water absorbing agent contained in the absorbent article, so that an excellent dry condition is kept after absorbing water. As a result, it is possible to reduce loads of a user wearing the absorbent article and caregivers.

Through the following examples and comparative examples, the present invention is described more specifically. However, the present invention is not limited to the following examples and the like, as long as the present invention is interpreted in light of a gist thereof. Note that, unless otherwise stated, "part(s)" means part(s) by weight.

Note that, properties of the particulate water absorbing agent were measured in the following measurement methods. Further, voltages and frequencies of all electric devices used in Examples were respectively 100V and 60 Hz. Further, the particulate water absorbing agent whose moisture content was adjusted to 6 wt % was used. Unless particularly specified, the measurement was performed at 25° C.±2° C. with a relative humidity of 50% RH. Further, 0.90 wt % of sodium chloride aqueous solution was used as physiological saline.

(1) Absorption Capacity (Centrifuge Retention Capacity in Five Minutes with Respect to 0.90 wt % of Sodium Chloride Aqueous Solution (CRC2), Centrifuge Retention Capacity in 30 Minutes with Respect to 0.90 wt % of Sodium Chloride Aqueous Solution (CRC1))

0.2 g of a particulate water absorbing agent resin or a water absorbent was evenly contained in a bag (60 mm×60 mm) made of a nonwoven fabric. Then, the bag was soaked in an extremely excessive amount (not less than 100 g for example) of 0.9 wt % sodium chloride aqueous solution (physiological saline) whose temperature had been adjusted to 25° C., and was withdrawn 5 or 30 minutes later. By using a centrifugal separator, the bag was drained for three minutes at 250 G, and a weight W2 (g) of the bag was measured.

Next, the same operation was performed without using the water absorbent and the water absorbent resin, and a weight W1 (g) was measured. Then, from the weights W1 and W2, an absorbency (g/g) was calculated according to the following (Equation 1).

Absorbency (g/g)=(weight $W2$(g)–weight $W1$(g))/ weight of water absorbent resin (g)　　(Equation 1)

A carryover factor (%) of a five-minute absorbency was calculated, by using thus obtained absorbencies (g/g) in 5 minutes and 30 minutes, in accordance with the following (Equation 2).

Carryover factor (%) of five-minute absorbency=absorbency-in-5-minute (g/g)/absorbency-in-30-minute(g/g)×100　　(Equation 2)

Note that, the absorbency in 30 minutes was regarded as a centrifuge retention capacity CRC1. Further, the absorbency in 5 minutes was regarded as a centrifuge retention capacity CRC2.

(2) Absorbency Against Pressure (Absorbency at Which 0.90 Mass % of Sodium Chloride Aqueous Solution Was Absorbed for 60 Minutes Under Pressure of 2.03 kPa (AAP1))]

By using a device of FIG. 1, the absorbency against pressure (AAP) was measured. There was prepared a load 208 adjusted so as to exert a pressure of 2.03 kPa (0.3 psi). On a bottom of a plastic supporting cylinder 204 having a 60 mm internal diameter, a metal gauze 202 of a stainless-steel 400 mesh (mesh size of 38 μm) was fusion-bonded. Then, 0.90 g (Wp2) of water absorbent or water absorbent resin was evenly dispersed on the mesh. Subsequently, the load 208 (at the time of 0.3 psi) is placed on the water absorbent resin or the water absorbent. Then, a weight Wa (g) of this measurement set was measured.

Inside a petri dish having a 150 mm diameter, a glass filter (product of Sougo Rikagaku Glass Seisakusho Co., Ltd.; diameter of fine pores: 100 μm to 120 μm) having a 90 mm diameter was placed. Thereafter, a 0.90 wt % of sodium chloride solution (20° C. to 25° C.) was added until it reaches a level of an upper surface of the glass filter.

Then, a piece of filter paper (product of Advantec Toyo Kaisha, Ltd.; product name: JIS P3801, No. 2; thickness: 0.26 mm; diameter of retained particles: 5 μm) whose diameter was 90 mm was placed thereon, so that an entire surface of the filter paper was wetted. An excess of the liquid was removed.

The measuring device set was placed on the wet filter paper, so that the liquid was absorbed under the load. One hour (60 minutes) later, the measuring device set was lifted, and a weight Wb (g) thereof was measured. From the weights Wa and Wb, an absorbency against pressure AAP1 (g/g) was calculated according to the following (Equation 3).

Absorbency against pressure $AAP1$ (g/g)=($Wb$ (g)–$Wa$ (g))/mass (0.9) g of water absorbent resin or water absorbent)　　(Equation 3)

Note that, although substantially the same value can be obtained at 2.03 kPa and 1.9 kPa, the measurement was performed at 2.03 kPa.

(3) Absorbency Against Pressure (Absorbency at Which 0.90 mass % of Sodium Chloride Aqueous Solution is Absorbed Under Pressure of 4.83 kPa (AAP2))]

Except that the 2.03 kPa load exerted to the water absorbent resin or the water absorbency was changed to a 4.83 kPa load (0.7 psi), the same operation as in the aforementioned calculation of AAP1 was performed, and an absorbency against pressure AAP2 (g/g) was calculated according to the following (Equation 4).

Absorbency against pressure $AAP2$ (g/g)=($Wb$ (g)–$Wa$ (g))/mass (0.9)g of a water absorbent resin or a water absorbent) (Equation 4)

(4) Weight (Mass) Average Particle Diameter

A water absorbent or a water absorbent resin was sieved by using a JIS standard sieve of 850 μm, 710 μm, 600 μm, 500 μm, 425 μm, 300 μm, 212 μm, 150 μm, 106 μm, 75 μm, or the like, and a percentage is plotted on logarithmic probability paper. Further, in accordance with an aperture corresponding to R=50%, a weight average particle diameter (D50) was found.

Further, as to the particle size distribution, a logarithmic standard deviation σζ represented by the following (Equation 5) as an index. Here, as σζ approaches to 0, the particle size distribution is narrower.

σζ=½$Ln$ ($X2/X1$) (Equation 5), where X1 represents a particle diameter when R=84.1 wt %, and X2 represents a particle diameter when R=15.9 wt %.

The sieving was performed as follows. Under a condition of a room temperature (20° C. to 25° C.) and 50% RH relative humidity, 10 g of the water absorbent resin powder or the water absorbent was put through a JIS standard sieve (The IIDA TESTING SIEVE; internal diameter: 80 mm), and was classified for 5 to 10 minutes by using a low-tap-type sieve shaking apparatus (ES-65 sieve shaking apparatus, product of Iida Seisakusho, Ltd.).

Note that, the weight average particle diameter (D50) is a particle diameter of a standard sieve, having a certain mesh size, which corresponds to 50 wt % of the whole particles (see U.S. Pat. No. 5,051,259 for example).

(5) Moisture Absorption Fluidity Index and Moisture Absorbency

Approximately 2 g of water absorbent resin or a water absorbent having passed through the JIS 20 mesh (mesh size of 850 μm) was evenly dispersed into an aluminum cup having a diameter of 52 mm, and a total weight (Bg) of the aluminum cup and the water absorbent resin or the particulate water absorbing agent was recorded. Thereafter, the resultant was left for one hour in a constant-temperature-and-moisture apparatus (PLATINOUS LUCIFFER PL-2G, product of TABAI ESPEC CORPORATION) at 25° C. and 90% RH relative humidity. One hour later, the water absorbent resin or the particulate water absorbing agent in the aluminum cup was softly moved onto a JIS standard sieve (The IIDA TESTING SIEVE; internal diameter: 80 mm) of JIS 8.6 mesh (mesh size of 2000 μm), and was classified for 5 seconds by using a low-tap-type sieve shaking apparatus (ES-65 sieve shaking apparatus, product of Iida Seisakusho, Ltd.; rotational frequency: 230 rpm; shock frequency: 130 rpm.), under a condition of a room temperature (20° C. to 25° C.) and 50% RH relative humidity. Then, a weight (D(g)) of the water absorbent resin or the particulate water absorbing agent which remained on the 2000 μmesh and a weight (E(g)) of the water absorbent resin or the particulate water absorbing agent which passed through the mesh were measured. In the present invention, the moisture-absorption-fluidity index is defined by the following (Equation 6), and the moisture absorbency is defined by the following (Equation 7), and calculation thereof was performed in accordance with the following (Equation 6) and (Equation 7).

Moisture-absorption-fluidity index (wt %)=(($E$(g))/($C$(g)–$A$(g)))×100 (Equation 6)

Moisture absorbency (%)={$C$(g)–$B$(g)}/($B$(g)–$A$(g))×100 (Equation 7)

(6) Quantity of Water Soluble Component (Extractable Polymer Content]

184.3 g of a 0.90 mass % of sodium chloride aqueous solution was measured and pored into a 250 ml plastic container having a cover. Into the aqueous solution, 1.00 g of a water absorbent resin or a particulate water absorbing agent was added, and the solution was stirred for 16 hours by using a stirring vane having a 40 mm length and a 8 mm diameter (for example, stirring vane A, product of Sougo Rikagaku Glass Seisakusho Co., Ltd.) and a magnetic stirrer so that a depth of its whirlpool was approximately 2 cm. In this way, a soluble component of the water absorbent or the water absorbent resin was extracted. The extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured, and used as a measurement solution.

Next, the physiological saline to which the water absorbent resin or the particulate water absorbing agent had not been added was titrated by using a 0.1N NaOH aqueous solution, until pH of the physiological saline reached 10. After that, the physiological saline was titrated by using a 0.1N HCl aqueous solution, until pH of the physiological saline reached 2.7. In this way, empty titration amounts ([bNaOH]ml and [bHCl] ml) were measured.

The same operation was performed with respect to the measurement solution, thereby measuring titration amounts ([NaOH]ml and [HCl]ml).

Thereafter, in accordance with the empty titration amounts and the titration amounts of the measurement solution, a quantity of a soluble component in the water absorbent resin or the particulate water absorbing agent was calculated. That is, for example, in case of a water absorbent resin or a particulate water absorbing agent including a known amount of acrylic acid and its sodium chloride, it was possible to calculate a quantity of a soluble component in the water absorbent resin or the particulate water absorbing agent, in accordance with the following (Equation 8), from an average molecular mass of the monomer and the titration amounts obtained by the foregoing operation.

Soluble amount (wt %)=0.1×(average molecular mass)×184.3×100×([HCl]–[$b$HCl])/1000/1.0/ 50.0 (Equation 8)

In case of using a water absorbent resin or a particulate water absorbing agent constituted of a component whose amount was unknown, the average molecular mass of the monomer was calculated from a neutralization ratio calculated in accordance with the following (Equation 9), and a soluble component in the water absorbent resin or the particulate water absorbing agent was calculated in accordance with the foregoing (Equation 8).

Neutralization ratio (mol %)=(1–([NaOH]–[$b$NaOH]) /([HCl]–[$b$HCl]))×100 (Equation 9)

Note that, in case of (i) a water absorbent resin or a particulate water absorbing agent obtained by using an unsaturated monomer containing no carboxyl group and (ii) a water absorbent resin or a particulate water absorbing agent whose properties cannot be measured by the foregoing method, a quantity of a water soluble component is measured in accordance with gravity measurement recited on column 23, lines 10 to 55 of U.S. Reissue Pat. No. Re37,021.

(7) Surface Tension 50 ml of physiological saline whose temperature had been adjusted to 20° C. was poured into a 100 ml beaker that had been sufficiently rinsed. First, a surface tension of the physiological saline was measured by using a tensiometer (K11 automatic tensiometer, product of KRUSS). In this measurement, the surface tension needs to be within a range of 71 to 75 mN/m. Next, a sufficiently rinsed fluorine rotor whose length was 25 mm and 0.5 g of the particulate water absorbing agent were put into the beaker containing the physiological saline whose temperature had been adjusted to 20° C. and surface tension had been measured, and were stirred for 4 minutes under a condition of 500 rpm. 4 minutes later, the stirring operation was stopped, and the particulate water absorbing agent containing water was precipitated. Thereafter, a surface tension of a supernatant liquid was measured by performing the same operation again. Note that, the present invention adopted a plate method using a platinum plate, and the plate was sufficiently rinsed with water before performing the measurement, and was thermally rinsed with a burner.

(8) Moisture Content and Solid Content Ratio 1.000 g of a water absorbent resin or a particulate water absorbing agent was placed in the aforementioned aluminum cup (diameter: 52 mm), and was heated for three hours in a windless oven at 180° C. Then, a percentage of a solid component and a percentage of a moisture content were calculated from a drying loss of the water absorbent resin or the particulate water absorbing agent.

Here, the solid content is the water absorbent resin or the particulate water absorbing agent from which a volatile component (mainly water) has been removed, that is, a pure resin component of the water absorbent resin or the particulate water absorbing agent resin, and a ratio of a mass of the solid content (quantity of the solid content) to a mass of the water absorbent resin or the particulate water absorbing agent having the volatile component is a solid content ratio (mass %).

(9) Flowability

The flowability was measured in accordance with a measurement method of Flowability (450. 2-02) defined by EDANA (European Disposables and Nonwovens Association).

100 g of the particulate water absorbing agent or the water absorbent resin was put into a hopper defined by EDANA, and a time taken for the particulate water absorbing agent or water absorbent resin to be entirely discharged was measured (a moment in which an inlet positioned at a lower portion of the hopper was opened was defined as 0 second). Note that, the measurement was performed at 25° C. with a relative humidity of 50% RH.

(10) Measurement of Insertion Distance (PID) and Insertion Work (PIW)

<Measurement Sample>

27 g to 30 g of a water absorbent resin or a particulate water absorbing agent was placed in a glass cylindrical sample tube (external diameter is 35 mm, internal diameter is 33 mm, height is 78 mm: for example, Screw tube No. 7 made by Maruemu Corporation., or the like), and was sufficiently shaken. Thereafter, on an iron plate, the resultant was tapped upward and downward for one minute (three times per second, vibration amplitude is 10 mm), thereby closely filling the cylindrical sample tube with water absorbent resin or the particulate water absorbing agent. Subsequently, by increasing or decreasing an amount of the water absorbent resin or the particulate water absorbing agent as required, adjustment was performed so that a height of the water absorbent resin or the particulate water absorbing agent closely filled in the cylindrical sample tube (hereinafter, such water absorbent resin or a particulate water absorbing agent is referred to as a particle layer) was 45 mm±1.5 mm. In case where the amount of the water absorbent resin or the particulate water absorbing agent was adjusted in this manner, the resultant was sufficiently shaken again. Thereafter, the resultant was tapped upward and downward for one minute (three times per second, vibration amplitude is 10 mm), thereby closely filling the sample tube with the water absorbent resin or the particulate water absorbing agent. Note that, the tapping was performed so that an upper surface of the particle layer was flat and horizontal after the tapping.

Further, in measuring PIW and PID, a value obtained by averaging values measured three times was adopted. Thus, the cylindrical sample tube in which the particle layer had been formed was covered with a lid and was sufficiently shaken each time of measurement, and the resultant was tapped upward and downward again on the iron plate for one minute as in the foregoing operation, thereby obtaining a measurement sample in which an upper surface of the particle layer was flat and horizontal.

<Measuring Device>

Figure 2:
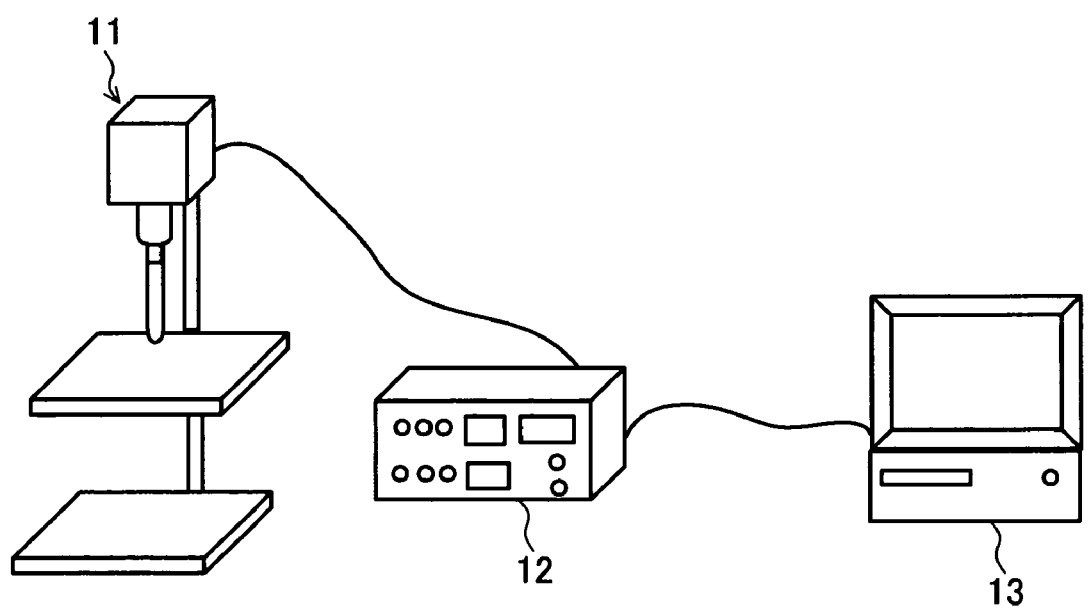
FIG. 2 is an oblique perspective view schematically showing an arrangement of a measurement device for measuring an insertion distance and an insertion work in a particulate water absorbing agent of the present invention.

Measurement of PIW and PID was performed by using a measuring device 10 (KES-G5 Handy Compression Tester: product of Kato-Tech.Co., Ltd, whose main office is located in Kyoto-shi, Minami-ku, Japan) shown in FIG. 2. The measuring device 10 includes: a compressor 11; a controller 12 for controlling the compressor 11; and a computer 13 for fetching data obtained from the compressor 11 and the controller 12, wherein the compressor 11, the controller 12, and the computer 13 are connected to each other via cables.

Figure 3:
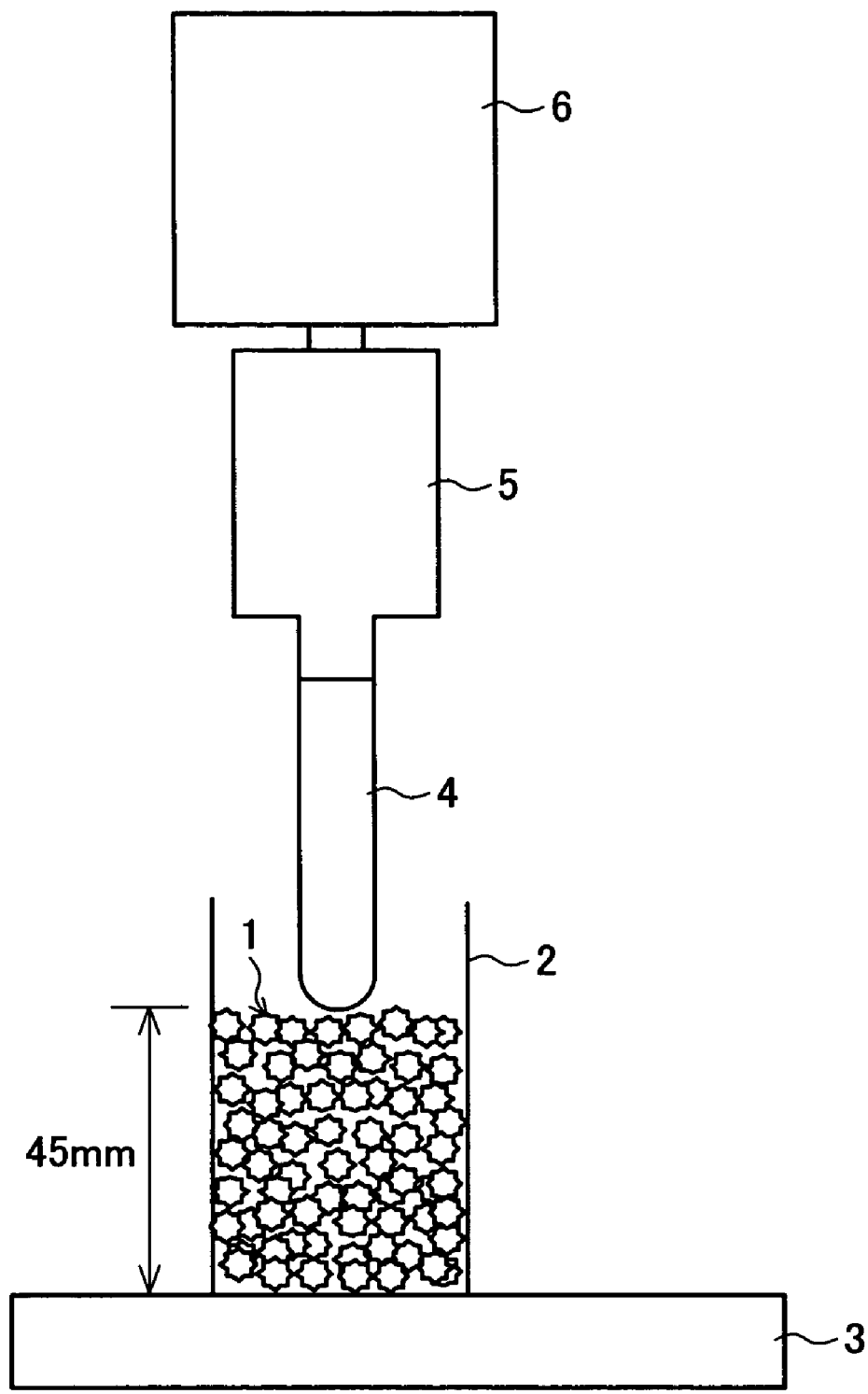
FIG. 3 is a front view showing an important portion of a compression device provided on the measurement device.

As shown in FIG. 3, the compressor 11 includes: a movable stage 3; an insertion probe (insertion member) 4; a movable load cell (force meter) 5; and a displacement distance detector 6.

Figure 4:
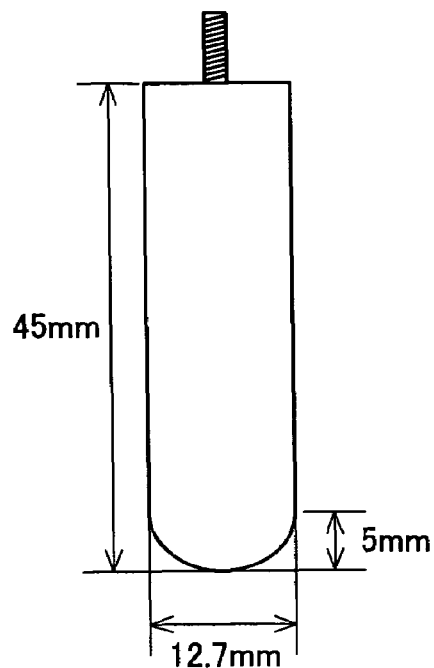
FIG. 4 is a front view showing an insertion probe (insertion member) provided on the measurement device.

The stage 3 is a table on which a measurement sample 2 filled with a particulate water absorbing agent or a water absorbent resin (hereinafter, a particle layer) 1 is placed, is movable forward and backward with respect to the insertion probe 4. Further, the insertion probe 4 is a metallic stick which is inserted into the particle layer 1 constituted of the particulate water absorbing agent or the water absorbent resin filled in the measurement sample 2. In the present example, as shown in FIG. 4, the insertion probe 4 has a diameter of 12.7 mm and a length of 40 mm, and is made of anodized aluminum whose end portion is rounded so as to have a spherical surface with a 5 mm radius. Note that, as to the insertion probe 4, its surface roughness standardized on the basis of JISB0601-1994 has a maximum height of usually 0 to 10 μm, preferably 0 to 1 μm, and a 10-point-average roughness is 0 to 10 μm, preferably 0 to 1 μm, and a central-line-average roughness is 0 to 5 μm, preferably 0 to 1 μm. As shown in FIG. 4, the insertion probe 4 is fixed to the load cell 5 (FIG. 3) with a screw, and integrally moves with the load cell 5.

Further, the load cell 5 applies various loads, whose upper limit is 10 kg, to the particle layer 1 in the measurement sample 2 via the insertion probe 4. As shown in FIG. 3, the load cell 5 is connected to the displacement distance detector 6, and is provided so as to be movable forward and backward with respect to the measurement sample 2. The displacement distance detector 6 detects a displacement distance which is a distance at which the load cell 5 moves.

Moreover, the controller 12 shown in FIG. 2 includes: an insertion speed adjuster for adjusting a speed at which the insertion probe 4 is inserted; a load adjuster for adjusting a load applied from the insertion probe 4 to the particle layer of the measurement sample 2; a displacement distance adjuster for adjusting a displacement distance of the load cell 5; a displacement distance display for displaying a displacement distance of the load cell 5; a load display for displaying a load applied to the particle layer of the measurement sample 2; and an integration indicator.

Further, the computer 13 shown in FIG. 2 fetches data, obtained from the compressor 11 and the controller 12, as digital data. The computer 13 stores (i) a displacement distance of the insertion probe 4 (that is, the load cell 5) which is in contact with an upper surface of the particle layer 1 of the measurement sample 2 and (ii) a load applied to the particle layer 1.

<Measuring Condition and Measuring Method>

The measuring device 10 was placed on a horizontal testing table with no vibration, and measurement of PID and PIW was performed as follows under a condition of a temperature of 25±1° C.) and 50±5% RH relative humidity.

That is, the measurement sample 2 was prepared in the aforementioned manner, and the measurement sample 2 was placed on the stage 3 of the compressor 11 (FIG. 2) of the measuring device 10 while giving least vibration thereto. Subsequently, the stage 3 was raised to and was fixed at such a position that an end portion of the insertion probe 4 shown in FIG. 3 touches the upper surface of the particle layer 1 in the measurement sample 2, and the position was defined as a starting point (0 mm).

Thereafter, the end portion of the insertion probe 4 was inserted into the particle layer 1 at an insertion speed of 1 mm per second. At the same time as commencement of the insertion of the insertion probe 4, the measurement was commenced so that data was read at intervals of 0.1 second, thereby measuring an insertion distance of the insertion probe 4 and a load which enabled insertion of the insertion probe 4. Note that, the insertion distance of the insertion probe 4 was within a range of from the starting point (0 mm) to 20 mm (within an error of 3%).

Figure 5:
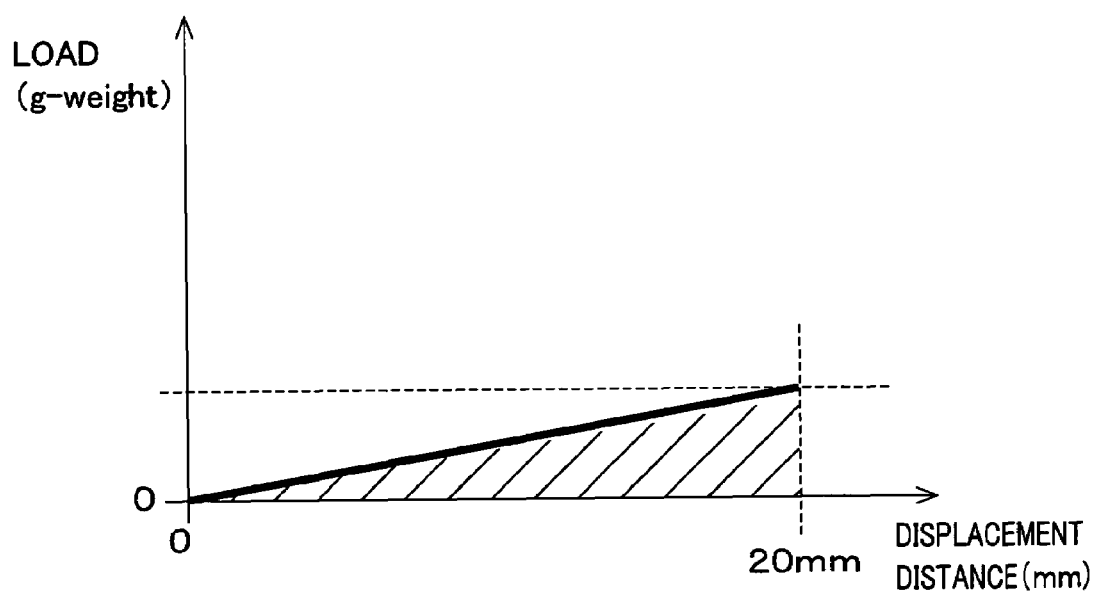
FIG. 5 is a graph showing an example of how a load required in inserting the insertion probe (insertion member) into a particle layer varies in each insertion distance of the insertion probe.

Further, as shown in FIG. 5, a graph was made so that the measured insertion distance (mm) is indicated by a horizontal axis and the measured load (g-weight or g f) was indicated by a vertical axis, and an area (shaded area of FIG. 5) surrounded by a curve constituted of values of the obtained load and the horizontal axis was integrated within a range of from 0 to 20 mm insertion distance, thereby obtaining an insertion work (PIW) at which the insertion probe 4 was inserted within 0 to 20 mm insertion distance.

Further, in case where the load reached the upper limit load of 10 kg by the time when the insertion distance reached 20 mm, an insertion distance at which the load reached the upper limit load of 10 kg was the PID value. In case where the insertion distance reached a maximum insertion distance of 20 mm without reaching the upper limit load of 10 kg, the PID value was 20 mm.

The foregoing operation was repeated three times so as to perform the measurement, and a value obtained by averaging thus three obtained values was regarded as a measurement value. As values of PIL and PIW determined in the foregoing manner are smaller, particles of the particulate water absorbing agent or the water absorbent resin of the particle layer 1 may be regarded as having more excellent sliding properties, and may be regarded as being easier to handle.

Note that, in case where the load had becomes 10,000 g weight before the insertion distance of the insertion probe 4 reaches 20 mm, the fluidity of the powder may be regarded as being extremely low. Thus, evaluation was performed in terms of merely an insertion distance (PID) of the insertion probe 4.

(11) Saline Flow Conductivity (SFC)

A saline flow conductivity (SFC) of 0.69 wt % physiological saline is a value indicative of a liquid permeation rate of the particulate water absorbing agent in a swelling state. A test was performed in accordance with a physiological saline flow conductivity (SFC) test recited in U.S. Patent No. 2004-0106745-A.

Figure 6:
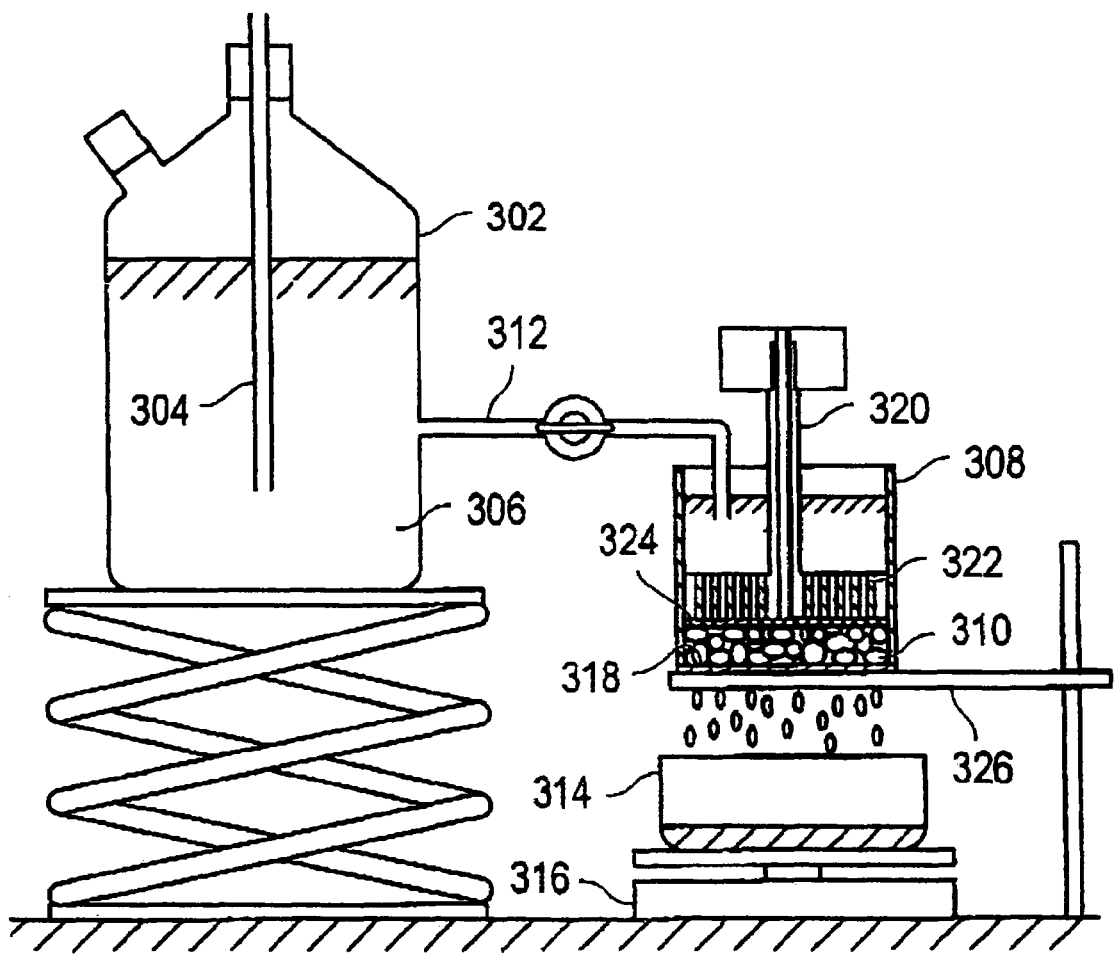
FIG. 6 is a cross sectional view schematically showing an arrangement of a device for measuring a saline flow conductivity in an Example of the present invention.

By using a device shown in FIG. 6, the particulate water absorbing agent (0.900 g) evenly contained in a cell 308 was swelled in a synthesized urine under a pressure of 0.3 psi (2.07 kPa) for 60 minutes), and a height of a gel layer of a gel 310 was recorded. Then, 0.69 wt % sodium chloride aqueous solution 306 was made to flow from a tank 302 and to pass through the swollen gel layer at a constant hydrostatic pressure.

In the device shown in FIG. 6, a glass tube 304 was inserted into the tank 302, and a lower end of the glass tube 304 was disposed so that 0.69 wt % sodium chloride aqueous solution 306 was positioned 5 cm higher than a bottom of the swelling gel 310 in the cell 308. 0.69 wt % sodium chloride aqueous solution 306 contained in the tank 302 was supplied to the cell 308 via an L-shaped tube 312 with a cock. A collecting container 314 for collecting liquid having passed through the gel layer was disposed under the cell 308, and the collecting container 314 was placed on an even balance 316. An inside diameter of the cell 308 was 6 cm, and No. 400 stainless metal gauze (38 μin mesh) 318 was placed on a bottom of a lower portion of the cell 308. A hole 322 which allowed liquid to pass through was provided on a lower portion of a piston 320, and a glass filter 324 having high permeability was provided on the bottom thereof so that the particulate water absorbing agent or the swelling gel did not enter into the hole 322. The cell 308 was placed on a table for the cell, and the table's surface which is in contact with the cell was positioned on the stainless metal gauze 326 which did not prevent the liquid from passing through.

The synthesized urine was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of ammonium dihydrogen phosphate, and 994.25 g of pure water.

Note that, the SFC test was performed at a room temperature (20 to 25° C.). By using a computer and a scale, an amount of liquid passing through the gel layer at intervals of 20 seconds was recorded for 10 minutes as a time function. A flow rate $Fs(t)$ of the solution passing through the swollen gel 310 (mainly between particles thereof) was determined in terms of g/s by dividing an increasing weight (g) by an increasing time (s). A time in which a constant hydrostatic pressure and a stable flow rate had been obtained was set as "ts", and only data obtained between "ts" and a ten-minute interval was used to calculate the flow rate, the flow rate calculated between "ts" and a ten-minute interval was used to calculate a value of $Fs$ ($t=0$), i.e., a first flow rate of the solution passing through the gel layer. $Fs$ ($t=0$) was calculated by extrapolating $t=0$ from a result obtained by approximating a function indicative of a relationship between $Fs$ (t) and t.

Further, the physiological saline flow conductivity (liquid permeation rate under pressure) was calculated in accordance with the following (Equation 10). Note that, a unit of the liquid permeation rate under pressure was ($10^{-7} \times cm^3 \times s \times g^{-1}$).

$$\text{Liquid Permeation Rate under Pressure} = \frac{Fs(t=0) \times L_0}{\rho \times A \times \Delta P} = \frac{Fs(t=0) \times L_0}{139506} \quad (10)$$

Here,

Fs (t=0): a flow rate represented by "g/s"

$L_0$: a height of the gel layer that is represented by "cm"

$\rho$: a density (1.003 g/cm$^3$) of NaCl solution

A: an area (28.27 cm$^2$) on the upper side of the gel layer of the cell 41

$\Delta P$: a hydrostatic pressure (4920 dyne/cm$^2$) exerted to the gel layer.

(12) Loose Bulk Density (Bulk Specific Gravity)

Figure 7A:
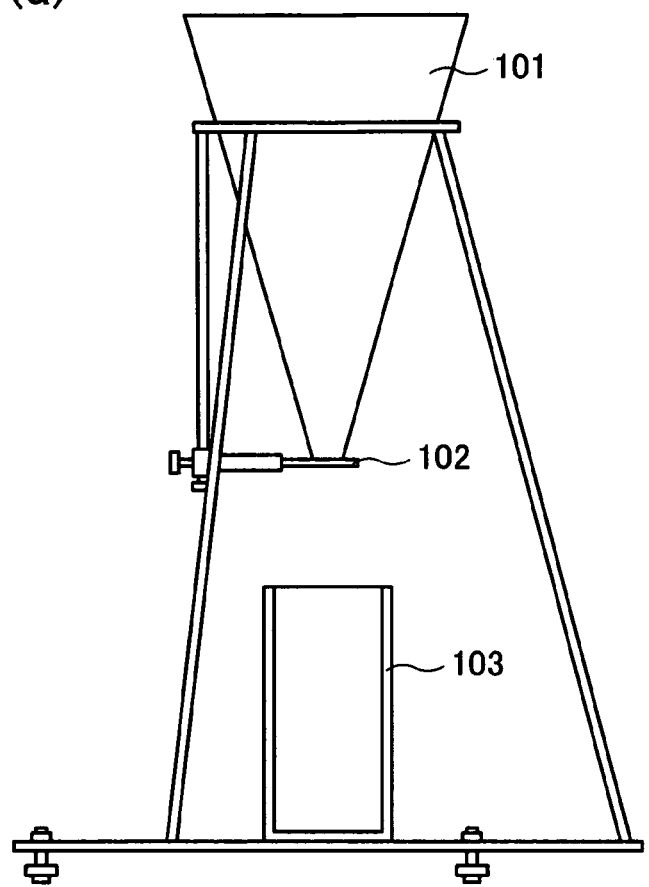
FIGS. 7(a) and 7(b) schematically show a device for measuring a loose bulk density and a flow rate in an Example of the present invention.
Figure 7B:
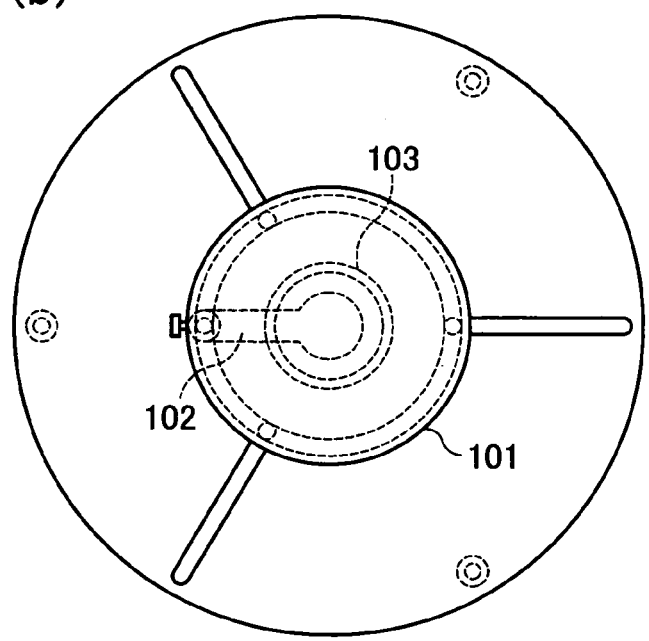

The loose bulk density was measured in accordance with JIS K3362. Specifically, the measurement was performed as follows by using a measuring device shown in FIG. 7.

(i) The measuring device was placed on a stable table, and a tripod screw was adjusted so as to keep the measuring device horizontal, and a dried funnel 101 was vertically placed on a stand, and its lower outlet was slightly sealed with a damper 102.

(ii) A cup 103, rinsed and dried in advance, whose mass was adjusted to 0.1 g, was placed under the funnel 101, and 100.0 g of sample classified in terms of property was softly put in the funnel 101.

(iii) The damper 102 was entirely opened quickly so that the sample in the funnel 101 was made to freely fall into the cup 103. When the sample was aggregated and adhered to the funnel 101, the sample was fragmented into pieces with a glass stick in advance. A portion swollen above the cup 103 was removed by a glass stick (its diameter was about 8 mm and its length was about 150 mm). Thereafter, a mass of the cup 103 containing the sample was adjusted to 0.1 g.

Further, the loose bulk density was calculated in accordance with the following equation.

$A=(W_2-W_1)/V$

A: loose bulk density (g/ml)

$W_2$: a mass (g) of the cup containing the sample $W_1$: a mass (g) of an empty cup V: a capacity (ml) of the cup Note that, the loose bulk density is often referred to merely as a bulk density or a bulk specific gravity, so that they are the same.

(13) Flow Rate

The flow rate was measured at the same time as the measurement of the loose bulk density. Specifically, in the measurement operation (iii) for the loose bulk density, a time since the damper 102 had been entirely opened until the whole sample completely fell was measured. This time was defined as t(s), and the flow rate was calculated in accordance with the following equation.

$Ve=100/t$

Ve: the flow rate (g/s)

(14) Tapped Bulk Density

The tapped bulk density was measured as follows.

(i) By using a spatula, approximately 100 g of a particulate water absorbing agent was put into a measuring cylinder, sufficiently rinsed and dried, whose mass was adjusted to 0.1 g (its capacity was 250 ml and its internal diameter was about 38 mm), and a mass of the measuring cylinder containing the sample was measured. In accordance with the difference therebetween, a mass m(g) of the sample was calculated.

(ii) The measuring cylinder containing the sample was tapped 100 times, on a flat test table, from a height of about 3 mm, so as to measure a volume of the sample with accuracy (so as to measure every ml).

(iii) Further, the tapping was repeated 100 times, and the volume of the sample was measured again. When a difference between the measured volumes is 1 ml or less, a smaller volume V (ml) was adopted, and the test was finished.

When the difference between the measured volumes was more than 1 ml, the tapping was further repeated 100 times, and the tapping was kept until a volume difference between two tapping operations sequentially performed did not exceed 1 ml.

When the volume difference is not more than 1 ml, a smaller volume V (ml) was adopted so as to finish the test. Then, the tapped bulk density was calculated in accordance with the following equation.

$P=m/V$

P: the tapped bulk density (g/ml)

(15) Compressibility Rate (%)

The compressibility rate was calculated from the loose bulk density A (g/ml) and the tapped bulk density P (g/ml) in accordance with the following equation.

$C=(P-A)/P \times 100$

C: the compressibility rate (%)

(16) Stirring Resistance

An SV2PSt-type rotor and an MV container were provided on an RV12-type viscometer (product of HAAKE), and a particulate water absorbing agent (about 80 g) whose amount was so large that a resistance measuring section of the rotor was completely hidden was put into the MV container by using a spatula, and then the rotor was rotated at 16 rpm. In one minute from beginning of the rotation, a torque T (N·cm) was measured. Thus measured value was regarded as the stirring resistance of the particulate water absorbing agent.

REFERENCE EXAMPLE 1

5.9 g of polyethyleneglycoldiacrylate (average added mole number of ethylene oxide: 8) were dissolved in a 5500 g of a sodium acrylate aqueous solution (monomer concentration: 38% by weight) having a 75 mol % neutralization ratio, so as to prepare a reaction solution. Then, the reaction solution was deaerated for 30 minutes in an atmosphere of nitrogen gas, and was fed to a reactor that had been prepared by placing a lid on a 10 L stainless-steel double-arm kneader equipped with two sigma vanes and a jacket. Inside the reactor was replaced with nitrogen gas while maintaining the temperature of the reaction solution at 30° C. Subsequently, 2.46 g of sodium persulfate and 0.10 g of L-ascorbic acid were added to the reaction solution, while the reaction solution was stirred. Approximately one minute later, polymerization was initiated. During the polymerization, the reaction solution was kept at 30° C. to 90° C. In 60 minutes after the polymerization was initiated, a water-containing gelled polymer was retrieved. Thus obtained water-containing gelled polymer had been fragmented so that its diameter was approximately 5 mm. The water-containing gelled polymer fragmented was spread out on a wire mesh of 50 mesh (mesh size is 300 μm), and was dried by hot air at 150° C. for 90 minutes. A dry polymer thus obtained was crushed by using a vibrating mill, and then classified and blended by using a wire mesh of 20 meshes (mesh size is 850 μm). Thus, a water absorbent resin (a) having a crushed indeterminate form was obtained. In 100 parts of thus obtained water absorbent resin (a), a surface cross-linking solvent including 0.03 parts of ethyleneglycol glycidyl ether, 0.5 parts of propyleneglycol, 0.3 parts of 1,4-butanediol, and three parts of water, was mixed. The mixture was then thermally processed at 200° C. for 45 minutes, thereby obtaining a water absorbent resin (A). As to thus obtained water absorbent resin (A), σξ was 0.35, D50 was 370 μm, a ratio of particles whose particle diameter was less than 150 μm was 2 wt %, and a quantity of soluble component was 17 wt %. As to the water absorbent resin (A), Table 1 shows measurement results of (i) absorbencies in 5 minutes and 30 minutes, (ii) a carryover factor of a five-minute absorbency, (iii) absorbencies under pressures of 2.03 kPa and 4.83 kPa, and (iv) a surface tension. Table 2 shows measurement results of a moisture-absorption fluidity index, a moisture absorbency, a flow rate, a PID, and a PIW.

REFERENCE EXAMPLE 2

14 g of acrylic acid, 6 g of stearyl acrylate, 0.1 g of 2,2'-azobisisobutyronitrile (AIBN) serving as an initiator, and 80 g of ethylalcohol serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 65° C., and a polymerization reaction thereof was carried out for two hours with the reaction solution stirred. Two hours later, the temperature was raised to 75° C., and was further reacted for an hour. Thereafter, the reaction solution was cooled down, thereby obtaining a macromolecule-additive-containing solution (B-1) containing 20 wt % of an acrylic acid-stearyl acrylate copolymer serving as a macromolecule additive.

Example 1

With respect to 100 parts of the water absorbent resin (A) obtained in Reference Example 1, 1.5 parts (0.3 parts as a macromolecule additive) of the macromolecule-additive-containing solution (B-1, 20 wt % of ethanol solution) were added, and they were mixed with each other, and the mixture was subjected to vacuum drying at 60° C. for three hours, thereby obtaining a particulate water absorbing agent (1). Further, with respect to 100 parts of the water absorbent resin (A) obtained in Reference Example 1, 5 parts (1 part as a macromolecule additive) of the macromolecule-additive-containing solution (B-1, 20 wt % of ethanol solution) were added, and they were mixed with each other, and the mixture was subjected to vacuum drying at 60° C. for three hours, thereby obtaining a particulate water absorbing agent (2).

Properties of thus obtained particulate water absorbing agents (1) and (2) are shown in Table 1, Table 2-1, and Table 2-2.

REFERENCE EXAMPLE 3

10 g of acrylic acid, 10 g of lauryl acrylate, 0.1 g of 2,2'-azobisisobutyronitrile (AIBN) serving as an initiator, and 80 g of ethylalcohol serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 65° C., and a polymerization reaction thereof was carried out for two hours with the reaction solution stirred. Two hours later, the temperature was raised to 75° C., and was further reacted for an hour. Thereafter, the reaction solution was cooled down, thereby obtaining a macromolecule-additive-containing solution (B-2) containing 20 wt % of an acrylic acid-lauryl acrylate copolymer serving as a macromolecule additive.

Example 2

With respect to 100 parts of the water absorbent resin (A) obtained in Reference Example 1, 5 parts (1 part as a macromolecule additive) of the macromolecule-additive-containing solution (B-2, 20 wt % of ethanol solution) were added, and they were mixed with each other, and the mixture was subjected to vacuum drying at 60° C. for three hours, thereby obtaining a particulate water absorbing agent (3). Properties of thus obtained particulate water absorbing agent (3) are shown in Table 1, Table 2-1, and Table 2-2.

Example 3

With respect to 100 parts of the water absorbent resin (A) obtained in Reference Example 1, 5.1 parts of a mixture solution of 5 parts (1 part as a macromolecule additive) of the macromolecule-additive-containing solution (B-2, 20 wt % of ethanol solution) and 0.1 parts of ethyleneglycol glycidyl ether were added, and they were mixed with each other, and the mixture was subjected to vacuum drying at 120° C. for 30 hours, thereby obtaining a particulate water absorbing agent (4). Properties of thus obtained particulate water absorbing agent (4) are shown in Table 1, Table 2-1, and Table 2-2.

REFERENCE EXAMPLE 4

Except that 14 g of 2-hydroxyethyl acrylate was used instead of acrylic acid as the monomer used, the same operation as that of Reference Example 2 was performed, thereby obtaining a macromolecule-additive containing solution (B-3) containing 20% of a hydroxyethyl acrylate-stearyl acrylate copolymer as a macromolecule additive.

Example 4

With respect to 100 parts of the water absorbent resin (A) obtained in Reference Example 1, 5 parts (1 part as a macromolecule additive) of the macromolecule-additive-containing solution (B-3, 20 wt % of ethanol solution) were added, and they were mixed with each other, and the mixture was subjected to vacuum drying at 60° C. for three hours, thereby obtaining a particulate water absorbing agent (5). Properties of thus obtained particulate water absorbing agent (5) are shown in Table 1, Table 2-1, and Table 2-2.

REFERENCE EXAMPLE 5

16 g of acrylic acid, 4 g of stearyl acrylate, 0.1 g of 2,2'-azobisisobutyronitrile (AIBN) serving as an initiator, and 80 g of acetic ether serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 70° C. In ten minutes after soaking the flask, polymer generated by polymerization was precipitated, so that the reaction solution became turbid. Twenty minutes later, the stirring operation was stopped and a reaction was carried out. Forty minutes later, the whole reaction system was solidified. In three hours after soaking the flask, the reaction solution was cooled down. Then, a solid product obtained by the reaction was subjected to vacuum drying at 60° C. for five hours. The dried solid product was an agglomeration of fine particles. By using a desk-top mill, the solid product was crushed into pieces. Thus obtained pieces were sieved by a sieve of 75 µm, thereby obtaining a macromolecule additive powder (B-4).

The particles were observed with a scanning electron microscope (SEM). As a result of the observation, it was found that the particles were an agglomeration, having a diameter of 5 to 50 µm, which was made up of particles having a diameter of 1 to 5 µm.

Example 5

With respect to 100 parts of the water absorbent resin (A) obtained in Reference Example 1, 1 part of the macromolecule additive powder (B-4) was added, and they were mixed with each other, thereby obtaining a particulate water absorbing agent (6). Properties of thus obtained particulate water absorbing agent (6) are shown in Table 1, Table 2-1, and Table 2-2.

REFERENCE EXAMPLE 6

14 g of acrylic acid, 6 g of lauryl acrylate, 0.1 g of 2,2'-azobisisobutyronitrile (AIBN) serving as an initiator, and 80 g of acetic ether serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 70° C. In ten minutes after soaking the flask, polymer generated by polymerization was precipitated, so that the reaction solution became turbid. Twenty minutes later, the stirring operation was stopped and a reaction was carried out. Forty minutes later, the whole reaction system was solidified. In three hours after soaking the flask, the reaction solution was cooled down. Then, a solid product obtained by the reaction was subjected to vacuum drying at 60° C. for five hours. The dried solid product was an agglomeration of fine particles. By using a desk-top mill, the solid product was crushed into pieces. Thus obtained pieces were sieved by a sieve of 75 µm, thereby obtaining a macromolecule additive powder (B-5).

The particles were observed with a scanning electron microscope (SEM). As a result of the observation, it was found that the particles were an agglomeration, having a diameter of 5 to 50 µm, which was made up of particles having a diameter of 1 to 5 µm.

Example 6

With respect to 100 parts of the water absorbent resin (A) obtained in Reference Example 1, 1 part of the macromolecule additive powder (B-5) was added, and they were mixed with each other, thereby obtaining a particulate water absorbing agent (7). Properties of thus obtained particulate water absorbing agent (7) are shown in Table 1, Table 2-1, and Table 2-2.

REFERENCE EXAMPLE 7

14 g of acrylic acid, 6 g of 2-ethyl-hexyl acrylate, 0.15 g of methylenebisacrylamide, 0.1 g of 2,2'-azobisisobutyronitrile (AIBN) serving as an initiator, and 80 g of acetic ether serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 70° C. In ten minutes after soaking the flask, polymer generated by polymerization was precipitated, so that the reaction solution became turbid. Twenty minutes later, the stirring operation was stopped and a reaction was carried out. Forty minutes later, the whole reaction system was solidified. In three hours after soaking the flask, the reaction solution was cooled down. Then, a solid product obtained by the reaction was subjected to vacuum drying at 60° C. for five hours. The dried solid product was an agglomeration of fine particles. By using a desk-top mill, the solid product was crushed into pieces. Thus obtained pieces were sieved by a sieve of 75 µm, thereby obtaining a macromolecule additive powder (B-6).

The particles were observed with a scanning electron microscope (SEM). As a result of the observation, it was found that the particles were an agglomeration, having a diameter of 5 to 50 µm, which was made up of particles having a diameter of 1 to 5 µm.

Example 7

With respect to 100 parts of the water absorbent resin (A) obtained in Reference Example 1, 1 part of the macromolecule additive powder (B-6) was added, and they were mixed with each other, thereby obtaining a particulate water absorbing agent (8). Properties of thus obtained particulate water absorbing agent (8) are shown in Table 1, Table 2-1, and Table 2-2.

REFERENCE EXAMPLE 8

10 g of acrylic acid, 5 g of stearyl acrylate, 5 g of undecylenoxypolyethyleneglycolmethacrylate (NK ECONOMER, ML-12G produced by SHIN-NAKAMURA CHEMICAL CO.LTD), 0.1 g of 2,2'-azobisisobutyronitrile (AIBN) serving as an initiator, and 80 g of ethylalcohol serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 65° C., and a polymerization reaction thereof was carried out for two hours with the reaction solution stirred. Two hours later, the temperature was raised to 75° C., and was further reacted for an hour. Thereafter, the reaction solution was cooled down, thereby obtaining a macromolecule-additive-containing solution (B-7) containing 20 wt % of an acrylic acid-undecylenoxypolyethyleneglycolmethacrylate copolymer serving as a macromolecule additive.

Example 8

With respect to 100 parts of the water absorbent resin (A) obtained in Reference Example 1, 5 parts (1 part as a macromolecule additive) of the macromolecule-additive-containing solution (B-7, 20 wt % of ethanol solution) were added, and they were mixed with each other, and the mixture was subjected to vacuum drying at 60° C. for three hours, thereby obtaining a particulate water absorbing agent (9). Properties of thus obtained particulate water absorbing agent (9) are shown in Table 1, Table 2-1, and Table 2-2.

Comparative Reference Example 1

10 g of acrylic acid, 10 g of butyl acrylate, 0.1 g of 2,2'-azobisisobutyronitrile (AIBN) serving as an initiator, and 80 g of ethylalcohol serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 65° C., and a polymerization reaction thereof was carried out for two hours with the reaction solution stirred. Two hours later, the temperature was raised to 75° C., and was further reacted for an hour. Thereafter, the reaction solution was cooled down, thereby obtaining a comparative macromolecule-additive-containing solution (C-1) containing 20 wt % of an acrylic acid-butyl acrylate copolymer serving as a comparative macromolecule additive whose lateral chain has merely a hydrocarbon group containing less than 7 carbons in its molecule.

Comparative Example 1

With respect to 100 parts of the water absorbent resin (A) obtained in Reference Example 1, 5 parts (1 part as a comparative macromolecule additive) of the comparative macromolecule-additive-containing solution (C-1, 20 wt % of ethylalcohol solution) were added, and they were mixed with each other, and the mixture was subjected to vacuum drying at 60° C. for three hours, thereby obtaining a comparative particulate water absorbing agent (CC-1). Properties of thus obtained comparative particulate water absorbing agent (CC-1) are shown in Table 1, Table 2-1, and Table 2-2.

Comparative Reference Example 2

10 g of dimethylaminoethyl acrylate hydrochloride, 10 g of butyl acrylate, 0.1 g of 2,2'-azobisisobutyronitrile (AIBN) serving as an initiator, and 80 g of isopropyl alcohol serving as a solvent were put into a 500 ml separable flask provided with a cooling tube, a stirring vane, and a motor for rotating the stirring vane, thereby preparing a reaction solution in which these components were completely solved. Next, the reaction solution was deaerated in a nitrogen gas atmosphere for 15 minutes. Subsequently, in a nitrogen airflow, the separable flask containing the reaction solution was soaked in a hot water bath whose temperature was 65° C., and a polymerization reaction thereof was carried out for two hours with the reaction solution stirred. Two hours later, the temperature was raised to 75° C., and was further reacted for an hour. Thereafter, the reaction solution was cooled down, thereby obtaining a comparative macromolecule-additive-containing solution (C-2) containing 20 wt % of a dimethylaminoethyl acrylate hydrochloride-butyl acrylate copolymer serving as a comparative macromolecule additive whose lateral chain has merely a hydrocarbon group containing less than 7 carbons in its molecule.

Comparative Example 2

With respect to 100 parts of the water absorbent resin (A) obtained in Reference Example 1, 5 parts (1 part as a comparative macromolecule additive) of the comparative macromolecule-additive-containing solution (C-2, 20 wt % of isopropyl alcohol solution) were added, and they were mixed with each other, and the mixture was subjected to vacuum drying at 60° C. for three hours, thereby obtaining a comparative particulate water absorbing agent (CC-2). Properties of thus obtained comparative particulate water absorbing agent (CC-2) are shown in Table 1, Table 2-1, and Table 2-2. Thus obtained product did not flow from the hopper, so that the flow rate could not be measured. The powder was inferior in the fluidity and had viscosity. Further, it was observed that a large amount of the powder adhered to the container.

Comparative Example 3

With respect to 100 parts of the water absorbent resin (CC-2) obtained in Comparative Example 2, 0.5 parts of hydrophilic silicon dioxide fine powder (Aerogil 200 (average particle diameter of primary particles is 12 nm: product of Nippon Aerogil, Ltd.) were further added as an additive, and they were mixed with each other, thereby obtaining a comparative particulate water absorbing agent (CC-3). Properties of thus obtained comparative particulate water absorbing agent (CC-3) are shown in Table 1, Table 2-1, and Table 2-2.

Comparative Example 4

With respect to 100 parts of the water absorbent resin (A) obtained in Reference Example 1, 1 part of cross-linking-type polyacrylic polymer fine powder (JUNLON PW-150 produced by NIHON JUNYAKU CO., LTD: particle diameter ranges from 5 to 50 μm according to SEM observation: aqueous solution viscosity is 95,000 cp per 1 wt %) was added as a macromolecule additive, and they were mixed with each other, thereby obtaining a comparative particulate water absorbing agent (CC-4). Properties of thus obtained comparative particulate water absorbing agent (CC-4) are shown in Table 1, Table 2-1, and Table 2-2.

Comparative Example 5

With respect to 100 parts of the water absorbent resin (A) obtained in Reference Example 1, 1 part of hydrophilic silicon dioxide fine powder (Aerogil 200 (average particle diameter of primary particles is 12 nm: product of Nippon Aerogil, Ltd.) was added as an additive, and they were mixed with each other, thereby obtaining a comparative particulate water absorbing agent (CC-5). Properties of thus obtained comparative particulate water absorbing agent (CC-5) are shown in Table 1, Table 2-1, and Table 2-2.

As to the particulate water absorbing agents (1) to (9) obtained in Examples 1 to 8 and the comparative particulate water absorbing agents (CC1) to (CC-5) obtained in Comparative Examples 1 to 5, Table 1 shows measurement results of (i) absorbencies in 5 minutes and 30 minutes, (ii) a carry-over factor of a five-minute absorbency, (iii) absorbencies under pressures of 2.03 kPa and 4.83 kPa, and (iv) a surface tension. Tables 2-1 and 2-2 show measurement results of a moisture-absorption fluidity index, a moisture absorbency, a flow rate, a PID, a PIW, a loose bulk density, a tapped bulk density, and a compressibility rate.

TABLE 1

|  |  | GV | | | AAP1 | AAP2 | Surface |
| --- | --- | --- | --- | --- | --- | --- | --- |
|  |  | 5 min (g/g) | 30 min (g/g) | Carryover factor (%) | 2.03 Kpa (g/g) | 4.83 Kpa (g/g) | tension (mN/m) |
| Reference Example1 | (A) | 25 | 34 | 74 | 31 | 23 | 73 |
| Example1 | (1) | 24 | 34 | 71 | 31 | 23 | 73 |
| Example1 | (2) | 23 | 34 | 68 | 30 | 22 | 74 |
| Example2 | (3) | 24 | 34 | 71 | 31 | 21 | 64 |
| Example3 | (4) | 21 | 32 | 66 | 28 | 21 | 66 |
| Example4 | (5) | 24 | 34 | 71 | 31 | 22 | 75 |
| Example5 | (6) | 24 | 34 | 71 | 31 | 22 | 72 |
| Example6 | (7) | 24 | 34 | 71 | 29 | 21 | 66 |
| Example7 | (8) | 24 | 34 | 71 | 29 | 21 | 55 |
| Example8 | (9) | 24 | 34 | 71 | 29 | 22 | 69 |
| Comparative Example1 | (CC-1) | 24 | 34 | 71 | 25 | 12 | 44 |
| Comparative Example2 | (CC-2) | 24 | 34 | 71 | 30 | 21 | 33 |
| Comparative Example3 | (CC-3) | 24 | 34 | 71 | 26 | 16 | 35 |
| Comparative Example4 | (CC-4) | 24 | 34 | 71 | 24 | 11 | 73 |
| Comparative Example5 | (CC-5) | 24 | 34 | 71 | 26 | 13 | 73 |

TABLE 2-1

|  |  | Flow rate (sec) | PID (mm) | PIW (g wt × mm) | Moisture absorbency (wt %) | Moisture-absorption fluidity index (wt %) |
| --- | --- | --- | --- | --- | --- | --- |
| Reference Example1 | (A) | 10 | 8 | — | 12 | 1 |
| Example1 | (1) | 11 | 20 | 14300 | 10 | 99 |
| Example1 | (2) | 11 | 20 | 9100 | 8 | 100 |
| Example2 | (3) | 11 | 20 | 39200 | 10 | 95 |
| Example3 | (4) | 11 | 20 | 34700 | 10 | 100 |
| Example4 | (5) | 12 | 20 | 19500 | 9 | 100 |
| Example5 | (6) | 12 | 20 | 12200 | 10 | 100 |
| Example6 | (7) | 12 | 20 | 45300 | 10 | 96 |
| Example7 | (8) | 12 | 20 | 47500 | 10 | 95 |
| Example8 | (9) | 11 | 20 | 11400 | 9 | 100 |
| Comparative Example1 | (CC-1) | 12 | 9 | — | 11 | 2 |
| Comparative Example2 | (CC-2) | No flow | 20 | 9800 | 10 | 60 |
| Comparative Example3 | (CC-3) | 15 | 10 | — | 10 | 100 |
| Comparative Example4 | (CC-4) | 11 | 7 | — | 12 | 2 |
| Comparative Example5 | (CC-5) | 12 | 7 | — | 12 | 100 |

TABLE 2-2

|  |  | Loose bulk density (g/ml) | Tapped bulk density (g/ml) | Compressibility rate (%) | D50 (μm) | σζ | 850/150 (%) |
|---|---|---|---|---|---|---|---|
| Reference Example1 | (A) | 0.65 | 0.82 | 21 | 370 | 0.35 | 98.0 |
| Example1 | (1) | 0.69 | 0.81 | 15 | 370 | 0.36 | 98.0 |
| Example1 | (2) | 0.70 | 0.80 | 13 | 380 | 0.37 | 98.5 |
| Example2 | (3) | 0.68 | 0.77 | 12 | 380 | 0.37 | 98.5 |
| Example3 | (4) | 0.68 | 0.78 | 13 | 385 | 0.38 | 98.5 |
| Example4 | (5) | 0.70 | 0.81 | 14 | 375 | 0.37 | 98.5 |
| Example5 | (6) | 0.72 | 0.82 | 12 | 360 | 0.34 | 97.0 |
| Example6 | (7) | 0.71 | 0.82 | 13 | 375 | 0.35 | 97.0 |
| Example7 | (8) | 0.71 | 0.81 | 12 | 375 | 0.35 | 97.0 |
| Example8 | (9) | 0.72 | 0.81 | 11 | 375 | 0.37 | 98.5 |
| Comparative Example1 | (CC-1) | 0.66 | 0.82 | 19 | 375 | 0.35 | 97.0 |
| Comparative Example2 | (CC-2) | 0.65 | 0.82 | 21 | 400 | 0.40 | 99.0 |
| Comparative Example3 | (CC-3) | 0.63 | 0.79 | 20 | 370 | 0.35 | 98.0 |
| Comparative Example4 | (CC-4) | 0.68 | 0.84 | 19 | 370 | 0.35 | 97.0 |
| Comparative example5 | (CC-5) | 0.62 | 0.77 | 19 | 370 | 0.35 | 98.0 |

Synthesis Example 1

Synthesis of Water Absorbent Resin 48.5 wt % of caustic soda aqueous solution, acrylic acid, 30 wt % of polyethyleneglycol diacrylate (number average molecular mass is 523) aqueous solution (I), a solution (II) in which 0.98 weight parts of 2-hydroxymethyl-2-methylpropiophenon and 1.08 weight parts of diethylene triamine 5 acetic acid 3 sodium were dissolved in 97.9 weight parts of 20 wt % acrylic aqueous solution, and water, were sequentially supplied to a mixer so that: flow of the caustic soda aqueous solution was 4.95 g/second, flow of the acrylic acid was 6.12 g/second, flow of the polyethyleneglycol diacrylate aqueous solution (I) was 0.0672 g/second, flow of the solution (II) was 0.0758 g/second, and flow of the water was 5.23 g/second, thereby mixing these components. At this time, a temperature of the monomer aqueous solution was 95° C. Further, 3 wt % sodium persulfate aqueous solution was added so that its flow was 0.234 g/second. Thereafter, thus obtained resultant was sequentially supplied on an endless belt, kept at about 100° C., whose active length (from a monomer inlet to an end of the belt) moving at 1.7 m/minute was 3.2 mm so that a thickness of the resultant was 4.9 mm. The monomer aqueous solution supplied on the belt was quickly polymerized, and was swollen while emitting moisture vapor, and constricted in about one minute after initiation of the polymerization. The water-containing polymer that had constricted was collected at the end of the belt, and was led to a meat chopper, and was sequentially fragmented. The water containing polymer that had been fragmented was dried for 40 minutes by a hot air drier whose temperature had been adjusted to 180° C. Thereafter, thus dried resultant was crushed by a roll mill. Next, the crushed product was classified by a JIS standard sieve (850 μm in mesh) and a JIS standard sieve (150 μin mesh), thereby obtaining a water absorbent resin (base polymer) which passed through the sieve of 850 μm and did not pass through the sieve of 150 μm.

Example 9

With respect to 100 parts of the water absorbent resin powder obtained in Synthesis Example 1, a surface cross-linking agent obtained by mixing 0.34 weight parts of 1,4-butanediol, 0.56 weight parts of propyleneglycol, 3.0 weight parts of water, and 0.0010 weight parts of polyoxyethylene (20) sorbitan monostearate (product of Kao Corporation) was mixed. Thereafter, thus obtained mixture was heated at 210° C. for 30 minutes, thereby obtaining a particulate water absorbing agent (10) whose surface was cross-linked. Properties of thus obtained particulate water absorbing agent (10) are shown in Table 3.

Example 10

Except that an amount of the polyoxyethylene (20) sorbitan monostearate was 0.0015 weight parts, the same operation as that of Example 9 was carried out, thereby obtaining a particulate water absorbing agent (11). Properties of the particulate water absorbing agent are shown in Table 3.

Example 11

Except that an amount of the polyoxyethylene (20) sorbitan monostearate was 0.0020 weight parts, the same operation as that of Example 9 was carried out, thereby obtaining a particulate water absorbing agent (12). Properties of the particulate water absorbing agent are shown in Table 3.

Example 12

Except that an amount of the polyoxyethylene (20) sorbitan monostearate was 0.0050 weight parts, the same operation as that of Example 9 was carried out, thereby obtaining a particulate water absorbing agent (13). Properties of the particulate water absorbing agent are shown in Table 3.

Example 13

Except that an amount of the polyoxyethylene (20) sorbitan monostearate was 0.010 weight parts, the same operation as that of Example 9 was carried out, thereby obtaining a particulate water absorbing agent (14). Properties of the particulate water absorbing agent are shown in Table 3.

Comparative Example 6

With respect to 100 parts of the water absorbent resin powder obtained in Synthesis Example 1, a surface cross-linking agent obtained by mixing 0.34 weight parts of 1,4-butanediol, 0.56 weight parts of propyleneglycol, and 3.0 weight parts of water was mixed. Thereafter, thus obtained mixture was heated at 210° C. for 30 minutes, thereby obtaining a comparative particulate water absorbing agent (CC-6) whose surface was cross-linked. Properties of thus obtained comparative particulate water absorbing agent (CC-6) are shown in Table 3.

Comparative Example 7

Except that an amount of the polyoxyethylene (20) sorbitan monostearate was 0.015 weight parts, the same operation as that of Example 9 was carried out, thereby obtaining a comparative particulate water absorbing agent (CC-7). Properties of the particulate water absorbing agent are shown in Table 3.

TABLE 3

|  | Examples | | | | | Comparative examples | |
| --- | --- | --- | --- | --- | --- | --- | --- |
|  | 9 | 10 | 11 | 12 | 13 | 6 | 7 |
| Particulate water absorbing agent | (10) | (11) | (12) | (13) | (14) | (CC-6) | (CC-7) |
| Amount of surfactant (weight parts) | 0.0010 | 0.0015 | 0.0020 | 0.0050 | 0.010 | — | 0.015 |
| Surface tension(mN/m) | 72.5 | 73.0 | 71.0 | 61.4 | 58.4 | 72.5 | 52.7 |
| CRC1(g/g)) | 30 | 30 | 31 | 31 | 31 | 30 | 31 |
| AAP2(g/g) | 26 | 25 | 25 | 25 | 24 | 25 | 24 |
| SFC ($10^{-7} * cm^3 * s * g^{-1}$) | 43 | 45 | 42 | 42 | 39 | 45 | 39 |
| Weight average particle diameter(μm) | 430 | 440 | 420 | 420 | 420 | 430 | 430 |
| Logarithmic standard deviation | 0.37 | 0.35 | 0.38 | 0.38 | 0.36 | 0.37 | 0.37 |
| Loose bulk density (g/ml) | 0.60 | 0.64 | 0.67 | 0.67 | 0.68 | 0.59 | 0.68 |
| Flow rate (g/s) | 8.7 | 9.0 | 8.7 | 8.8 | 8.9 | 7.6 | 9.0 |
| Tapped bulk density (g/ml) | 0.73 | 0.72 | 0.73 | 0.72 | 0.73 | 0.73 | 0.73 |
| Compressibility rate (%) | 17 | 11 | 8 | 6 | 7 | 20 | 6 |
| Stirring Resistance (N * cm) | 0.36 | 0.35 | 0.23 | 0.21 | 0.20 | 0.39 | 0.20 |
| PIW(g wt × mm) | 37400 | 24200 | 7900 | 8500 | 7800 | — | 7400 |
| PID(mm) | 20 | 20 | 20 | 20 | 20 | 9 | 20 |
| 850/150 μm(%) | 100 | 100 | 100 | 100 | 100 | 100 | 100 |

Synthesis Example 2

Synthesis of Water Absorbent Resin

In a stainless-steel double-arm kneader equipped with two sigma vanes and a jacket, 0.10 mol % of polyethyleneglycoldiacrylate were dissolved in a sodium acrylate aqueous solution having a 71.3 mol % neutralization ratio, so as to prepare a reaction solution. Next, the reaction solution was deaerated for 30 minutes in an atmosphere of nitrogen gas. Subsequently, 10 wt % of sodium persulfate aqueous solution and 0.1 wt % of L-ascorbic acid aqueous solution were added to the reaction solution, while the reaction solution was stirred. Approximately one minute later, polymerization was initiated. While crushing the generated gel, the polymerization was carried out at 20 to 95%. In 20 minutes after the polymerization was initiated, a water-containing gelled polymer was retrieved. Thus obtained water-containing gelled polymer had been fragmented so that its diameter was approximately 5 mm.

The water-containing gelled polymer fragmented was dried by hot air at 170° C. for 50 minutes. A dry polymer thus obtained was crushed by using a roll mill, and then classified by using a JIS standard sieve (mesh size is 850 μm) and a JIS standard sieve (mesh size is 150 μm), thereby obtaining base polymer powder which passed through the sieve of 850 μm and did not pass through the sieve of 150 μm.

In 100 parts of thus obtained base polymer powder, a surface cross-linking solvent including 0.5 weight parts of 1,4-butanediol, 1.0 weight part of propyleneglycol, and three parts of water, was mixed. The mixture was then thermally processed at 210° C. for approximately 30 minutes, thereby obtaining a water absorbent resin whose surface had been cross-linked.

Example 14

100 g of the water absorbent resin obtained in Synthesis Example 2 and 0.6 mg of zinc stearate were put into a 500 ml plastic container, and these components were mixed by shaking the plastic container, thereby obtaining a particulate water absorbing agent (15). A loose bulk density of thus obtained particulate water absorbing agent (15) was measured in accordance with JIS K3362. Also water absorbent properties (CRC2, AAP1, SFC) of the particulate water absorbing agent were measured. Results thereof are shown in Table 4.

Example 15

Except that an amount of the zinc stearate was 0.15 mg, the same operation as that of Example 14 was carried out, thereby obtaining a particulate water absorbing agent (16). Further, as in Example 14, a loose bulk density and water absorbent properties (CRC2, AAP1, SFC) of thus obtained particulate water absorbing agent (16) were measured. Results thereof are shown in Table 4.

Comparative Example 8

With respect to 100 g of the water absorbent resin obtained in Synthesis Example 2, the same operation was that of Example 14 was carried out without adding the zinc stearate, thereby obtaining a comparative particulate water absorbing agent (CC-8). Further, as in Example 14, water absorbent properties (CRC2, AAP1, SFC) of thus obtained comparative particulate water absorbing agent (CC-8) were measured. Results thereof are shown in Table 4.

Example 16

100 g of the water absorbent resin obtained in Synthesis Example 2 and 1 mg of amide erucate were put into a stainless-steel beaker, and were left for 5 minutes in a convection dryer whose temperature was 150° C. Then, the beaker was retrieved and its temperature was measured by inserting a thermometer thereinto. As a result of the measurement, the temperature was approximately 75° C. After the measurement, the resultant was softly shaken so as to be mixed. The mixed resultant was cooled to a room temperature, thereby obtaining a particulate water absorbing agent (17). A loose bulk density of thus obtained particulate water absorbing agent (17) was measured in accordance with JIS K3362. Also water absorbent properties (CRC2, AAP1, SFC) of the particulate water absorbing agent were measured. Results thereof are shown in Table 4.

Comparative Example 9

With respect to 100 g of the water absorbent resin obtained in Synthesis Example 2, the same operation was that of Example 16 was carried out without adding the amide erucate, thereby obtaining a comparative particulate water absorbing agent (CC-9). Further, as in Example 16, water absorbent properties (CRC2, AAP1, SFC) of thus obtained comparative particulate water absorbing agent (CC-9) were measured. Results thereof are shown in Table 4.

Note that, as to the particulate water absorbing agents obtained in Examples 14 to 16 and Comparative Examples 8 and 9, a PID, a PIW, and a surface tension were measured. Results of the measurement are shown in Table 4.

TABLE 4

|  | Examples | | | Comparative examples | |
|---|---|---|---|---|---|
|  | 14 | 15 | 16 | 8 | 9 |
| Particulate water absorbing agent | (15) | (16) | (17) | (cc-8) | (cc-9) |
| Water absorbent resin Amount (g) | 100 | 100 | 100 | 100 | 100 |
| Powder lubricant |  |  |  |  |  |
| Type | Zinc stearate | Zinc stearate | Amide erucate | — | — |
| Amount (mg) | 0.6 | 1.5 | 1.0 | — | — |
| Loose bulk density (bulk specific gravity) (g/ml) | 0.70 | 0.72 | 0.70 | 0.67 | 0.66 |
| Flow rate (g/s) | — | — | 11.4 | — | 10.2 |
| Absorbency (CRC1)(g/g) | 30 | 30 | 31 | 30 | 31 |
| Absorbency against pressures(AAP2)(g/g) | 25 | 26 | 25 | 25 | 25 |
| Saline flow conductivity (SFC) ($10^{-7} * cm^3 * s * g^{-1}$) | 42 | 39 | 40 | 40 | 43 |
| PIW(g wt × mm) | 22400 | 8100 | 1350 | — | — |
| PID(mm) | 20 | 20 | 20 | 7 | 7 |
| Surface tension(mN/m) | 73 | 73 | 72 | 74 | 73 |
| Tapped bulk density(g/ml) | 0.82 | 0.83 | 0.83 | 0.83 | 0.82 |

TABLE 4-continued

|  | Examples | | | Comparative examples | |
| --- | --- | --- | --- | --- | --- |
|  | 14 | 15 | 16 | 8 | 9 |
| Compressibility rate(%) | 15 | 12 | 16 | 19 | 20 |
| 850/150 μm(%) | 100 | 100 | 100 | 100 | 100 |

Example 17

<Fabrication of Water Absorbent Article>

A water absorbent article for evaluation was fabricated as follows.

First, 50 weight parts of the particulate water absorbing agent and 50 weight parts of crushed wood pulp were mixed in a drying manner using a mixer. Next, the obtained mixture was deposited, in an airy-formation manner, on a wire screen which was 400 mesh (38 μm in mesh), using a batch type airy formation device, so as to form the mixture of 120 mm×400 mm. Further, this web was pressed at a pressure of 2 kg/cm² (196.14 kPa) for 60 seconds, thereby obtaining a water absorbent body whose scale was approximately 500 g/m². Next, a back sheet (liquid-impermeable sheet), made of liquid-impermeable polypropylene, which has a so-called leg gather, the absorbent core, and a top sheet (liquid-permeable sheet) made of liquid-permeable polypropylene were made to adhere to each other in this order using double face tapes, and two so-called tape fasteners were made to adhere to this adhesive material, thereby obtaining a water absorbent article (that is, a disposable diaper).

<Performance Evaluation of Water Absorbent Article>

The water absorbent article was placed on a horizontal test table so that its top sheet was positioned upward. Then, four corners of the water absorbent article were fixed with adhesive tapes with it extended so that there was no wrinkle. Next, a 20 mesh metal gauze (140 mm×400 mm) which was 850 μm in mesh was placed thereon, and an acrylic board (140 mm×400 mm) whose central portion had a cylinder having a diameter of 70 mm and a height of 50 mm was further provided so that liquid could be poured from the central portion. Note that, a mass of the acrylic board used was 1.5 kg. Subsequently, two weights each of which was 4.25 kg were placed on the acrylic board so that each of the weights was positioned in each of both sides of the cylinder. A total mass of the acrylic board and the weights was 10 kg, and a load exerted to the absorbent core was 2.06 kPa. Under such condition, 75 ml of 0.9 wt % sodium chloride aqueous solution (physiological saline) was poured from the cylinder at once, and a time taken for liquid to disappear from the cylinder was measured. This time was defined as a liquid pouring time. After leaving the liquid for an hour, the same operation was repeated, thereby poring the liquid four times. At this time, liquid pouring times in first to fourth pouring operations were measured. In an hour after the fourth pouring operation, the weight, the acrylic board, and the metal gauze were quickly removed. Subsequently, (i) thirty paper towels (140 mm×400 mm) whose mass was known, (ii) a flat acrylic board, and (iii) two weights each of which was 10 kg, were placed thereon. One minute later, the weights were removed, and a mass of the paper towels was measured. Based on change in the mass of the paper towels, a re-wet amount was measured.

It is considered that: as the liquid pouring times of the first to fourth pouring operations are shorter, the water absorbent article is superior. Further, it is considered that: as a re-wet amount is smaller, the water absorbent performance is higher.

Comparative Example 10

As to the comparative particulate water absorbing agent (CC-1) obtained in Comparative Example 1, the same operation as that of Example 17 was carried out, thereby obtaining a water absorbent article. A performance evaluation thereof was carried out.

Comparative Example 11

As to the comparative particulate water absorbing agent (CC-5) obtained in Comparative Example 5, the same operation as that of Example 17 was carried out, thereby obtaining a water absorbent article. A performance evaluation thereof was carried out.

As to the water absorbent articles obtained in Example 17, Comparative Examples 10 and 11, performance evaluations thereof were carried out.

TABLE 5

| Absorbent | Example 17 | Comparative example 10 | Comparative example 11 |
| --- | --- | --- | --- |
|  | Particulate water absorbing agent (1) | Comparative particulate water absorbing agent (CC-1) | Comparative particulate water absorbing agent (CC-5) |
| First liquid pouring time(sec) | 4 | 4 | 4 |
| Second liquid pouring time(sec) | 17 | 16 | 16 |
| Third liquid pouring time(sec) | 20 | 23 | 21 |
| Fourth liquid pouring time(sec) | 22 | 27 | 22 |
| Re-wet amount(g) | 12 | 18 | 16 |

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A particulate water absorbing agent comprising a water absorbent resin, having a cross-linking structure, whose surface has been cross-linked by adding a surface treatment agent, wherein:

(i) a mass average particle diameter (D50) ranges from 200 to 600 μm and 95 to 100 wt % of a particulate water absorbing agent whose particle diameter ranges from less than 850 μm to not less than 150 μm is contained with respect to 100 wt % of whole the particulate water absorbing agent, and (ii) a logarithmic standard deviation (σζ) of particle size distribution ranges from 0.25 to 0.45, and (iii) a compressibility rate defined by a following equation ranges from 0 to 18%, and (iv) a surface tension of a supernatant liquid obtained in 4 minutes after dispersing 0.5 g of the particulate water absorbing agent in 50 ml of physiological saline whose temperature is 20° C. is 55 mN/m or more, the compressibility rate $(\%)=(P-A)/P \times 100$ where P represents a tapped bulk density of the particulate water absorbing agent and A represents a loose bulk density of the particulate water absorbing agent.

2. The particulate water absorbing agent as set forth in claim 1, wherein an insertion work indicative of a work in case of inserting an insertion member down to a 20 mm depth of a particle layer of the particulate water absorbing agent is 0 g weight×mm or more and 75,000 g weight×mm or less.

3. The particulate water absorbing agent as set forth in claim 1, wherein the water absorbent resin has at least one shape selected from a group of an indefinite-shape crushed particle, a granulated indefinite-shape crushed particle, a granulated spherical particle, and a granulated elliptical particle, or has a shape obtained by mixing the indefinite-shape crushed particle, the granulated indefinite-shape crushed particle, the granulated spherical particle, and the granulated elliptical particle with each other.

4. An absorbent article, comprising the particulate water absorbing agent as set forth in claim 1.

* * * * *